US009884117B2

(12) United States Patent
Brige et al.

(10) Patent No.: US 9,884,117 B2
(45) Date of Patent: Feb. 6, 2018

(54) STABLE FORMULATIONS OF POLYPEPTIDES AND USES THEREOF

(75) Inventors: Ann Brige, Ertvelde (BE); Christine Labeur, Bruges (BE); Marc Jozef Lauwereys, Haaltert (BE)

(73) Assignee: Ablynx N.V., Zwijnaarde (BE)

( * ) Notice: Subject to any disclaimer, the term of this patent is extended or adjusted under 35 U.S.C. 154(b) by 92 days.

(21) Appl. No.: 13/393,679

(22) PCT Filed: Sep. 3, 2010

(86) PCT No.: PCT/EP2010/062972
§ 371 (c)(1),
(2), (4) Date: Apr. 30, 2012

(87) PCT Pub. No.: WO2011/026945
PCT Pub. Date: Mar. 10, 2011

(65) Prior Publication Data
US 2012/0201812 A1 Aug. 9, 2012

Related U.S. Application Data

(60) Provisional application No. 61/284,502, filed on Dec. 18, 2009, provisional application No. 61/275,816, filed on Sep. 3, 2009.

(51) Int. Cl.
*C07K 16/00* (2006.01)
*C07K 16/24* (2006.01)
*A61K 39/00* (2006.01)
*A61K 39/395* (2006.01)
*A61K 9/19* (2006.01)
*A61K 9/00* (2006.01)
*A61K 47/02* (2006.01)
*A61K 47/14* (2017.01)
*A61K 47/26* (2006.01)

(52) U.S. Cl.
CPC ...... *A61K 39/39591* (2013.01); *A61K 9/0019* (2013.01); *A61K 47/02* (2013.01); *A61K 47/14* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,171,586 B1 | 1/2001 | Lam et al. | |
| 7,807,162 B2 | 10/2010 | Silence | |
| 8,188,233 B2 | 5/2012 | Condra | |
| 8,623,361 B2 * | 1/2014 | Beirnaert et al. | 424/136.1 |
| 8,703,131 B2 | 4/2014 | Beirnaert | |
| 2003/0113316 A1 | 6/2003 | Kaisheva et al. | |
| 2003/0138417 A1 * | 7/2003 | Kaisheva et al. | 424/130.1 |
| 2003/0181527 A1 * | 9/2003 | Andersson et al. | 514/645 |
| 2003/0202972 A1 * | 10/2003 | Andya et al. | 424/131.1 |
| 2006/0088523 A1 * | 4/2006 | Andya et al. | 424/133.1 |
| 2006/0115470 A1 | 6/2006 | Silence et al. | |
| 2006/0149041 A1 | 7/2006 | Silence | |
| 2007/0086979 A1 | 4/2007 | Chevrier et al. | |
| 2007/0172479 A1 | 7/2007 | Warne et al. | |
| 2008/0292640 A1 * | 11/2008 | Solinger et al. | 424/158.1 |
| 2009/0226530 A1 | 9/2009 | Lassner et al. | |
| 2009/0280129 A1 | 11/2009 | Liu et al. | |
| 2010/0137213 A1 | 6/2010 | Fernandez et al. | |
| 2011/0311515 A1 * | 12/2011 | Bouche et al. | 424/130.1 |
| 2012/0034212 A1 * | 2/2012 | Bowen et al. | 424/133.1 |
| 2012/0093839 A1 | 4/2012 | Brige et al. | |
| 2012/0244158 A1 * | 9/2012 | Brige et al. | 424/135.1 |
| 2014/0178383 A1 | 6/2014 | Brige et al. | |

FOREIGN PATENT DOCUMENTS

| | | |
|---|---|---|
| WO | WO 2002/30463 A2 | 4/2002 |
| WO | WO 2004/041863 A2 | 5/2004 |
| WO | WO 2004/062551 A2 | 7/2004 |
| WO | WO 2005/044858 A1 | 5/2005 |
| WO | WO 2005/072772 A1 | 8/2005 |
| WO | WO 2006/020935 A2 | 2/2006 |
| WO | WO 2006/040153 A2 | 4/2006 |
| WO | WO 2006/074947 A2 | 7/2006 |
| WO | WO 2006/122825 A2 | 11/2006 |
| WO | WO 2007/002261 A2 | 1/2007 |
| WO | WO 2007/042289 A2 | 4/2007 |
| WO | WO 2007/0086797 A1 | 8/2007 |

(Continued)

OTHER PUBLICATIONS

Cleland et al., The development of stable protein formulations: a close look at protein aggregation, deamidation, and oxidation. Crit Rev Ther Drug Carrier Syst. 1993;10(4):307-77.
Barthelemy et al., Comprehensive analysis of the factors contributing to the stability and solubility of autonomous human VH domains. J Biol Chem. Feb. 8, 2008;283(6):3639-54. Epub Nov. 28, 2007.
Bork, Powers and pitfalls in sequence analysis: the 70% hurdle. Genome Res. Apr. 2000;10(4):398-400.
Bowie et al., Deciphering the message in protein sequences: tolerance to amino acid substitutions. Science. Mar. 16, 1990;247(4948):1306-10.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Dottorini et al., Crystal structure of a human VH: requirements for maintaining a monomeric fragment. Biochemistry. Jan. 27, 2004;43(3):622-8. Epub Dec. 25, 2003.

(Continued)

*Primary Examiner* — Joanne Hama
*Assistant Examiner* — Regina M Deberry
(74) *Attorney, Agent, or Firm* — Wolf, Greenfield & Sacks, P.C.

(57) ABSTRACT

Stable formulations are provided that contain immunoglobulin single variable domains at a high concentration. The formulations are useful as pharmaceutical formulation and suitable for subcutaneous administration. The formulations can be transported and stored under various stress conditions. The invention further relates to containers and pharmaceutical units comprising such formulations and to methods for preparing and prophylactic and therapeutic uses of the formulations and pharmaceutical units of the invention.

22 Claims, 52 Drawing Sheets

(56) References Cited

FOREIGN PATENT DOCUMENTS

Figure 1:
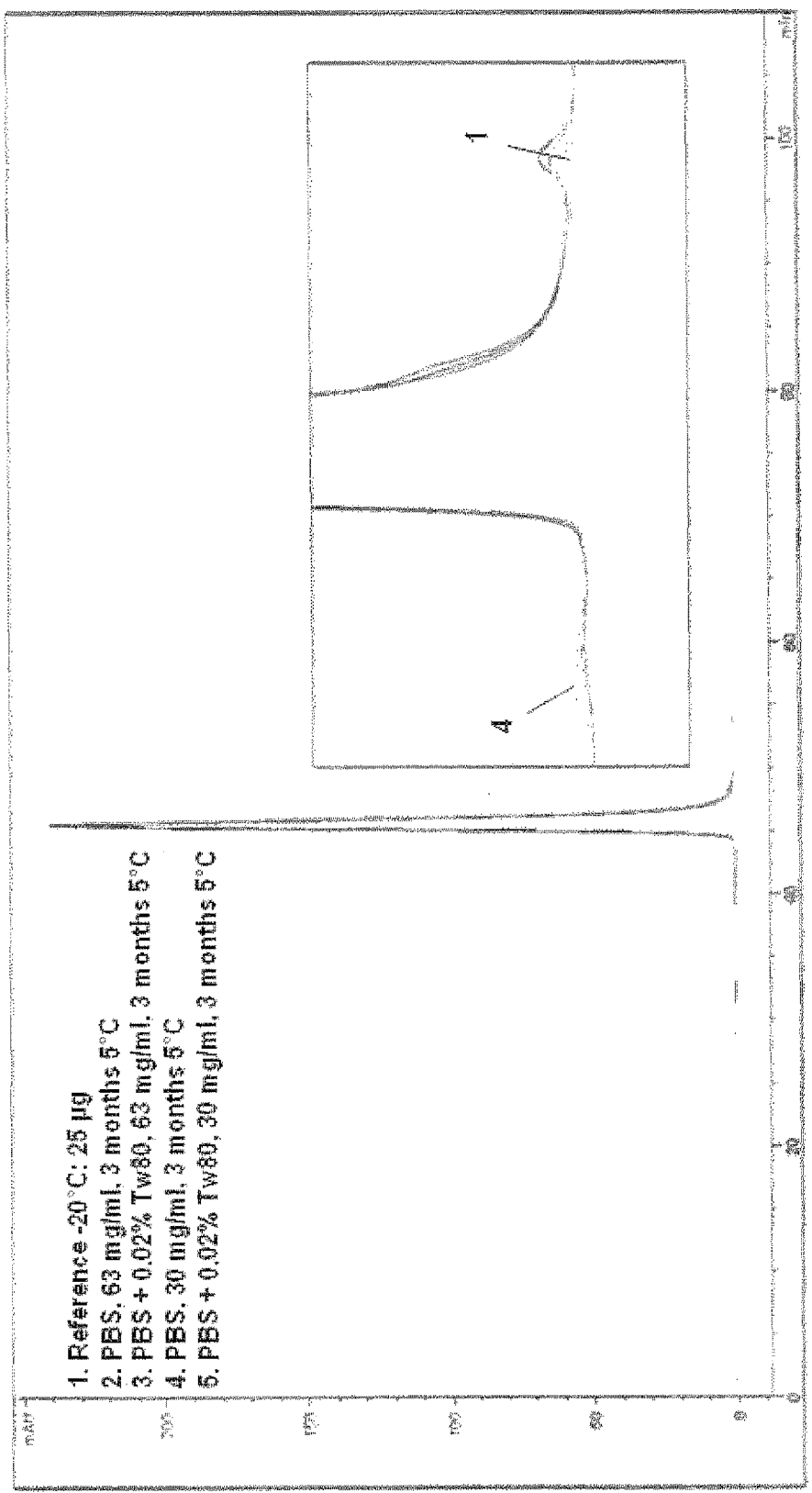
Figure 1:
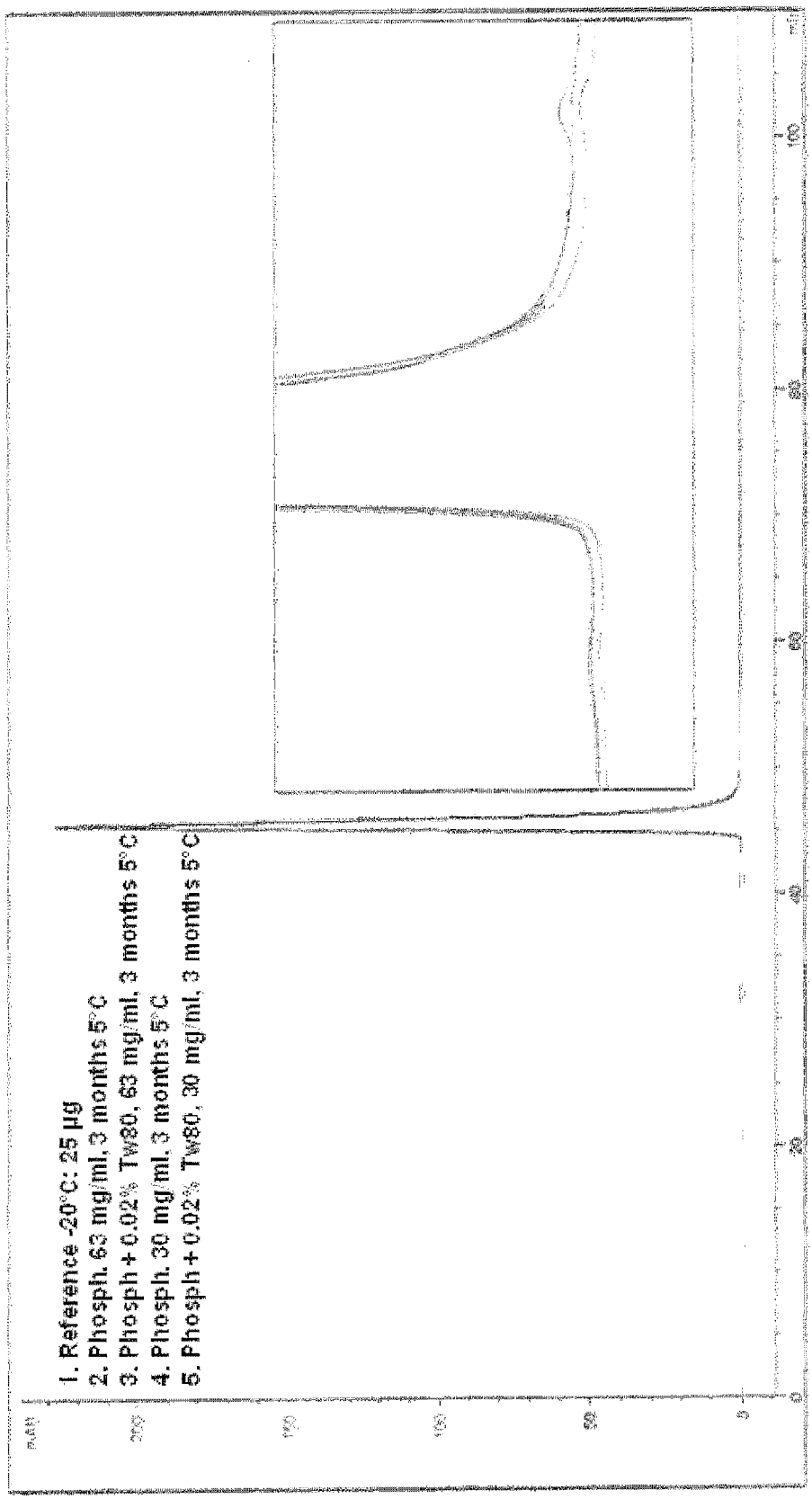
Figure 1:
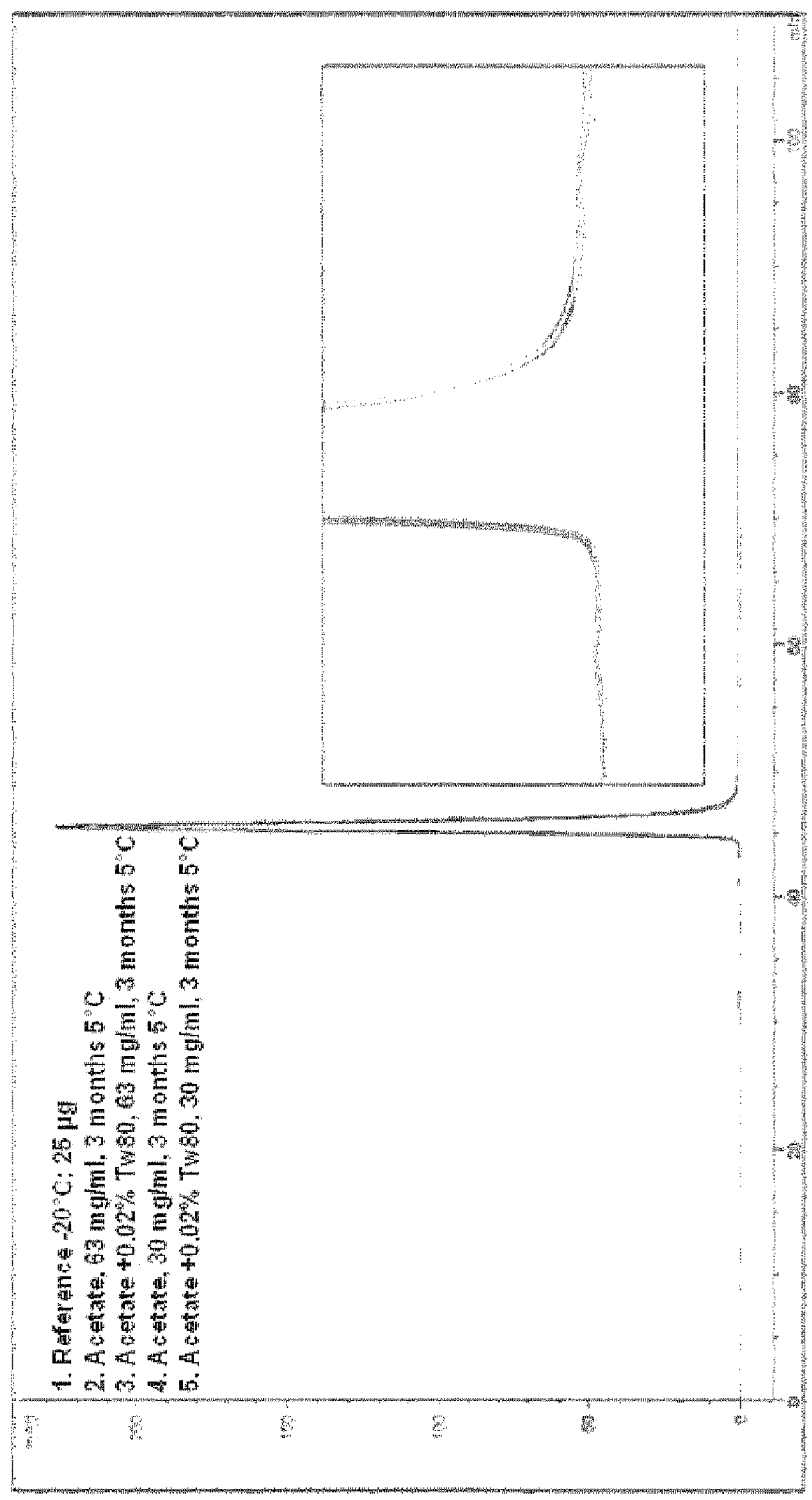

| | | | |
|---|---|---|---|
| WO | WO 2007/092772 A2 | 8/2007 |
| WO | WO 2007/104529 A2 | 9/2007 |
| WO | WO 2008/020079 A1 | 2/2008 |
| WO | WO 2008/039761 A2 | 4/2008 |
| WO | WO 2008/049897 A1 | 5/2008 |
| WO | WO 2008/070721 A2 | 6/2008 |
| WO | WO 2008/071447 A2 | 6/2008 |
| WO | WO 2008/071685 A1 | 6/2008 |
| WO | WO 2008/074839 A2 | 6/2008 |
| WO | WO 2008/074840 A2 | 6/2008 |
| WO | WO 2008/074867 A2 | 6/2008 |
| WO | WO 2008/074868 A1 | 6/2008 |
| WO | WO 2008/077945 A2 | 7/2008 |
| WO | WO 2008/079290 A2 | 7/2008 |
| WO | WO 2008/101985 A2 | 8/2008 |
| WO | WO 2008/142164 A2 | 11/2008 |
| WO | WO 2008/142165 A1 | 11/2008 |
| WO | WO 2009/068625 A2 | 6/2009 |
| WO | WO 2009/068627 A2 | 6/2009 |
| WO | WO 2009/095235 A1 | 8/2009 |
| WO | WO 2009/099641 A2 | 8/2009 |
| WO | WO 2009/109635 A2 | 9/2009 |
| WO | WO 2009/115614 A2 | 9/2009 |
| WO | WO 2010/060768 A1 | 6/2010 |
| WO | WO 2010/077422 A2 | 7/2010 |

OTHER PUBLICATIONS

Lazar et al., Transforming growth factor alpha: mutation of aspartic acid 47 and leucine 48 results in different biological activities. Mol Cell Biol. Mar. 1988;8(3):1247-52.

Riechmann et al., Single domain antibodies: comparison of camel VH and camelised human VH domains. J Immunol Methods. Dec. 10, 1999;231(1-2):25-38.

Sepúlveda et al., Binders based on dimerised immunoglobulin VH domains. J Mol Biol. Oct. 17, 2003;333(2):355-65.

Spinelli et al., Domain swapping of a llama VHH domain builds a crystal-wide beta-sheet structure. FEBS Lett. Apr. 23, 2004;564(1-2):35-40. Epub Mar. 29, 2004.

U.S. Appl. No. 13/964,469, filed Aug. 12, 2013, Brige et al.

PCT/EP2010/052600, Jun. 30, 2010, International Search Report and Written Opinion.

PCT/EP23010/052600, Sep. 15, 2011, International Preliminary Report on Patentability.

PCT/EP2010/062975, Nov. 2, 2010, International Search Report and Written Opinion.

PCT/EP2010/062975, Mar. 15, 2012, International Preliminary Report on Patentability.

[No Author Listed] Glycine (aminozuur). Wikipedia. Last accessed at http://nl.wikipedia.org/wiki/glycine_(aminozuur) on Oct. 30, 2009.

[No Author Listed] Koolhydraat. Wikipedia. Last accessed at http://nl.wikipedia.org/wiki/koolhydraat on Oct. 30, 2009.

[No Author Listed] Mannitol, a polypol (or sugar alcohol). Polyols Information Source. Last accessed at http://www.polyol.org/fap/fap_mannitol.html on Oct. 30, 2009.

[No Author Listed] Mannitol. Wikipedia. Last accessed at http://nl.wikipedia.org/wiki/mannitol on Oct. 30, 2009.

[No Author Listed] Polyol. Wikipedia. Last accessed at http://nl.wikipedia.org/wiki/polyol on Oct. 30, 2009.

[No Author Listed] Sacharose. Wikipedia. Last accessed at http://nl.wikipedia.org/wiki/sucrose on Oct. 30, 2009.

[No Author Listed] Scientific Discussion. EMEA 2005. 29 pages.

Chang et al., Practical approaches to protein formulation development. Amgen, Inc. 2002. 1-25.

Katayama et al., Effect of buffer species on the thermally induced aggregation of interferon-tau. J Pharm Sci. Jun. 2006;95(6):1212-26.

Labeur, Development of a high concentraiton Nanobody® formulation. Ablynx. Presentation. Sep. 9, 2009.

Jorgensen et al., Recent trends in stabilising peptides and proteins in pharmaceutical formulation—considerations in the choice of excipients. Expert Opin Drug Deliv. Nov. 2009;6(11):1219-30. doi:10.1517/17425240903199143.

Trevino et al., Amino acid contribution to protein solubility: Asp, Glu, and Ser contribute more favorably than the other hydrophilic amino acids in RNase Sa. J Mol Biol. Feb. 16, 2007;366(2):449-60. Epub Oct. 13, 2006.

Trevino et al., Measuring and increasing protein solubility. J Pharm Sci. Oct. 2008;97(10):4155-66. doi: 10.1002/jps.21327.

U.S. Appl. No. 15/042,207, filed Feb. 12, 2016, Brige et al.

* cited by examiner

Figure 11:
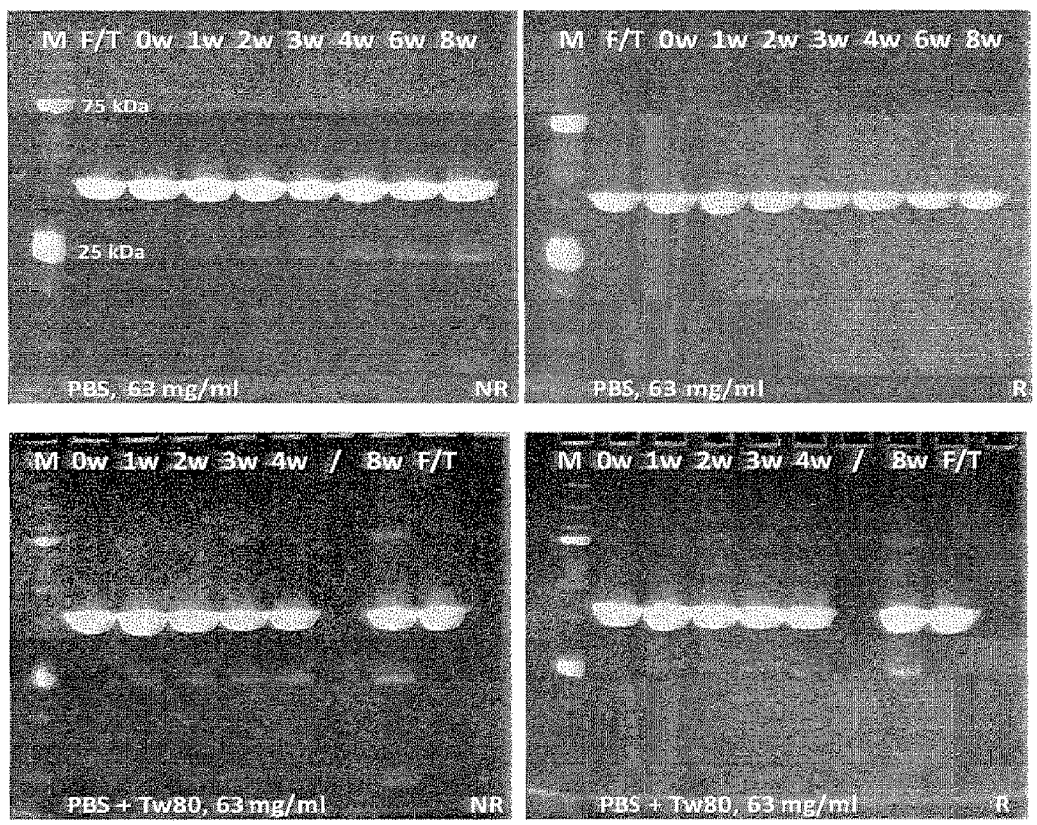

Figure 11: continued
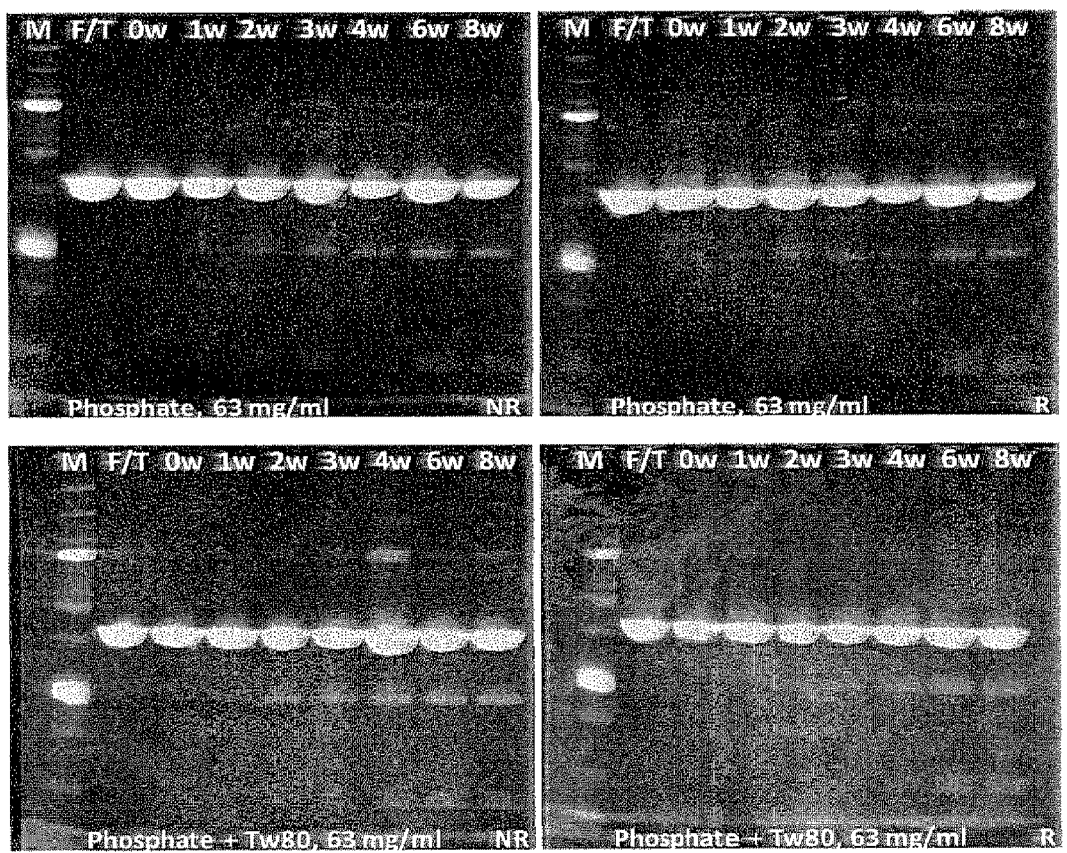

Figure 11: continued
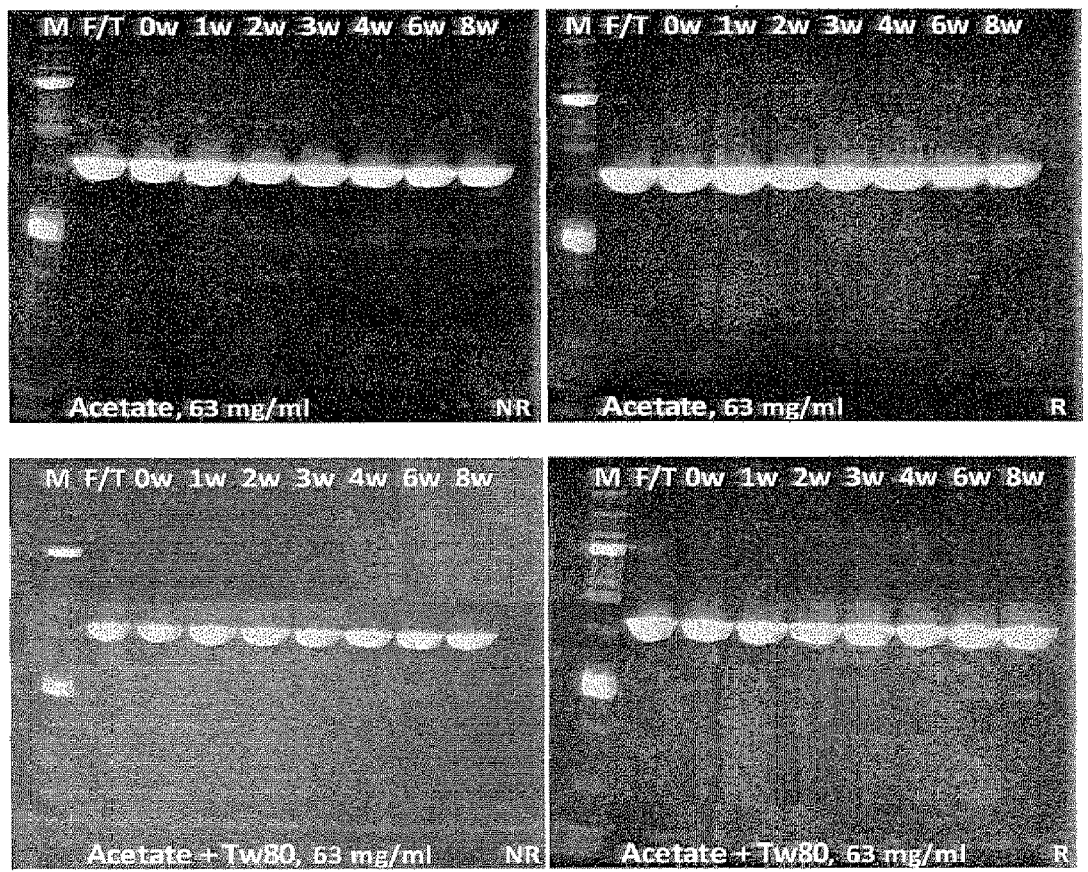

Samples:
1. RANKL008a diluted to 5 mg/ml without Tween-80
2. RANKL008a diluted to 5 mg/ml with 0.01% Tween-80
3. RANKL008a undiluted without Tween-80
4. RANKL008a undiluted with 0.01% Tween-80

| Diluted/undiluted | Without Tween-80 | 0.01% Tween-80 |
|---|---|---|
| Diluted to 5 mg/ml | Opaque (sample 1) | Clear (sample 2) |
| | More foam (sample 1) | Foam (sample 2) |
| Undiluted | Clear (sample 3) | Clear (sample 4) |
| | More foam (sample 3) | Foam (sample 4) |

STABLE FORMULATIONS OF POLYPEPTIDES AND USES THEREOF

RELATED APPLICATIONS

This application is a national stage filing under 35 U.S.C. § 371 of international application PCT/EP2010/062972, filed Sep. 3, 2010, which claims the benefit under 35 U.S.C. § 119(e) of U.S. provisional application Ser. No. 61/275,816, filed Sep. 3, 2009 and U.S. provisional application Ser. No. 61/284,502, filed Dec. 18, 2009, the disclosures of which are incorporated by reference herein in their entireties.

FIELD OF THE INVENTION

The present invention relates to formulations of single variable domains. More specifically the present invention provides formulations that contain single variable domains at a high concentration and that still can be transported and/or stored for longer periods of time. The formulations of the invention with the high concentration of single variable domains are suitable for subcutaneous administration.

The invention further relates to containers and pharmaceutical units comprising such formulations and to prophylactic and therapeutic uses of the formulations and pharmaceutical units of the invention.

Other aspects, embodiments, advantages and applications of the invention will become clear from the further description herein.

BACKGROUND ART

Proteins, such as therapeutic antibodies, are often transported and/or stored for later use. It is important that such proteins preserve the stability and biological activity of the protein under various conditions such as different temperature regimens and mechanical stress.

Certain prior liquid antibody preparations have shown short shelf lives and loss of biological activity of the antibodies resulting from chemical and/or physical instabilities during the transportation and storage. Chemical instability may be caused by deamidation, racemization, hydrolysis, oxidation, beta elimination or disulfide exchange, and physical instability may be caused by antibody denaturation, aggregation, precipitation or adsorption. Among those, aggregation, deamidation and oxidation are known to be the most common causes of the antibody degradation (Cleland et al., 1993, Critical Reviews in Therapeutic Drug Carrier Systems 10: 307-377).

Nanobodies (as further described herein) are characterized by formation of the antigen binding site by a single variable domain, which does not require interaction with a further domain (e.g. in the form of VH/VL interaction) for antigen recognition. Nanobodies against RANKL that can inhibit osteoclast formation and that could be candidates for further drug development are described in WO 08/142,164. The OPG/RANKL/RANK system has recently been discovered as pivotal regulatory factors in the pathogenesis of bone diseases and disorders like e.g. osteoporosis.

Up to now, most of the single variable domains have been administered intravenously. Intravenous (and intramuscular) injections, however, are generally performed by the physician or by the medical professional staff. Therefore, the patient is expected to visit a surgery or a hospital regularly in order to receive treatment. Besides the discomfort created, the time taken up by this type of application often leads to unsatisfactory compliance by the patient, particularly when the treatment extends over several months. Subcutaneous injection renders the possibility to the patient to self-administer the drug and consequently improve patients' cooperation and compliance. These advantages are even more evident in the case of a long-term therapy, such as the treatment of bone diseases and disorders. Another advantage of the subcutaneous administration lies in a substantially lower complication rate due to possible side effects, such as abscess formation and nerve lesions.

The volume of pharmaceutical formulation that can be administered to a patient subcutaneously, however, is more restricted. Therefore, in order to be able to administer a sufficient dose of active substance to the patient, for subcutaneous administration, a higher concentration of drug substance in the pharmaceutical formulation is required so that the required biological effect can still be obtained. Formulation at high protein concentration however comes with a number of challenges and risks, the biggest risk being the formation of aggregates. Understanding the physico-chemical behavior of the single variable domain at high protein concentration is therefore of key importance before defining the final formulation of the pharmaceutical compound.

SUMMARY OF THE INVENTION

The present invention provides formulations of single variable domains (also referred to as "formulation(s) of the invention") that are suitable for subcutaneous administration to a subject. The formulations of the invention comprise the single variable domain at concentrations of 30 mg/ml or higher (such as e.g. 40 mg/ml, 50 mg/ml, 60 mg/ml, 65 mg/ml, 70 mg/ml, 80 mg/ml, 90 mg/ml or even 100 mg/ml or higher) and still exhibit good stability, low to undetectable levels of aggregation, low to undetectable levels of single variable domain fragmentation/degradation, and very little to no loss of the biological activities of the single variable domains, even during transportation and/or long periods of storage.

The present invention provides stability data for formulations with polypeptides comprising one or more single variable domains (also referred to as "polypeptides of the invention") at a protein concentration that is sufficiently high to be compatible with subcutaneous administration. The invention further shows that such formulations can be transported and have a long shelf-life by applying mechanical stress conditions and by storage at various stress conditions such as in lyophilized form, at 2-8° C., in a frozen state at −20±5° C. or below −64° C. (such as e.g. at −80° C.) and at elevated temperature.

The polypeptide comprising one or more single variable domains for use in the formulation of the invention may be therapeutic or prophylactic, and may be useful in the treatment and/or management of one or more diseases. In one specific aspect, the polypeptide has three single variable domains. In another specific aspect, the polypeptide is useful in diseases and/or disorders associated with bone loss. Preferably, the polypeptide is directed against and/or specifically binds RANKL and/or HSA. More preferably, the polypeptide is directed against and/or specifically binds RANKL and HSA. In another specific aspect, the polypeptide comprises at least a single variable domain against RANKL. In another aspect, the polypeptide comprises at least a single variable domain against HSA. In yet another aspect, polypeptide comprises at least a single variable domain against RANKL and at least a single variable domain against HSA. Preferably, the single variable domain(s) used in the polypeptide of the invention are selected from WO 08/142,164. A preferred polypeptide of the invention is a trivalent polypeptide comprising two single variable domains against RANKL and one single variable domain against HSA, of which SEQ ID NO: 1 is a particularly preferred example.

The formulations of the present invention comprise such a polypeptide of the invention at high concentration (such as at least 30 mg/ml, at least 40 mg/ml, at least 50 mg/ml, preferably at least 50 mg/ml, at least 65 mg/ml or at least 70 mg/ml, more preferably at least 80 mg/ml or at least 90 mg/ml, most preferably at least 100 mg/ml or more) and still exhibit stability under one or more of the following stress conditions:

multiple (up to 10) freeze/thaw cycles;
storage at a temperature of −20±5° C. up to at least 3 months (preferably at least 6 months, at least 9 months, at least 1 year, 1.5 year or even 2 years or more);
storage at a temperature of 2-8° C. up to at least 3 months (preferably at least 6 months, at least 9 months, at least 11 months, at least 1 year, 1.5 year or even 2 years or more);
storage at a temperature of 25±5° C. up to at least 6 weeks;
storage at a temperature of 37±5° C. up to at least 2 weeks (preferably at least 4 weeks, more preferably at least 6 weeks, most preferably at least 8 weeks or more); and/or
mechanical stress.

Mechanical stress as used in the present invention can be any form of external force applied on the formulation that may affect the stability of the polypeptide present in the formulation. Without being limiting, the mechanical stress applied to the solution can be shear stress, stir stress, shake stress, rotation stress, etc. Preferably the formulation of the invention is stable under one or more of the following forms of mechanical stress:

shaking the formulation during 10 s to 1 min;
pushing the formulation through a needle (25 G, preferably 26 G, more preferably 27 G, even more preferably 28 G, most preferably 29 G or more) with a syringe (the syringe used can be any commercially available syringe, such as e.g. a 1 ml, 2 ml, 3 ml, 4 ml, 5 ml, 10 ml up to 50 ml syringe);
rotating far two days at 10 rpm; and/or
stirring for 1 hour at room temperature and/or 2 days at 4° C. at least 10 rpm (such as 50 rpm, 100 rpm or more).

Preferably, the formulations of the present invention are stable under more than one (such as two, three, four, five, six, seven or eight) of the above stress conditions, most preferably under all of the above stress conditions.

Accordingly, the polypeptide of the invention present in the formulation of the invention at high concentration (such as at least 30 mg/ml, at least 40 mg/ml, at least 50 mg/ml, preferably at least 60 mg/ml, at least 65 mg/ml or at least 70 mg/ml, more preferably at least 80 mg/ml or at least 90 mg/ml, most preferably at least 100 mg/ml or more):

is stable after multiple (up to 10) freeze/thaw cycles, said stability as determined by OD320/OD280 measurement, SE-HPLC, IEX-HPLC, RP-HPLC, potency assay (such as Biacore or ELISA) and/or SDS-PAGE;
is stable during storage at a temperature of −20±5° C. up to at least 3 months (preferably at least 6 months, at least 9 months, at least 1 year, 1.5 year or even 2 years or more), said stability as determined by OD320/OD280 measurement, SE-HPLC, IEX-HPLC, RP-HPLC, potency assay (such as Biacore or ELISA) and/or SDS-PAGE;
is stable during storage at a temperature of 2-8° C. up to at least 3 months (preferably at least 6 months, at least 9 months, at least 11 months, at least 1 year, 1.5 year or even 2 years or more), said stability as determined by OD320/OD280 measurement, SE-HPLC, IEX-HPLC, RP-HPLC, potency assay (such as Biacore or ELISA) and/or SDS-PAGE;
is stable during storage at a temperature of 25±5° C. up to at least 6 weeks, said stability as determined by OD320/OD280 measurement, SE-HPLC, IEX-HPLC, RP-HPLC, potency assay (such as Biacore or ELISA) and/or SOS-PAGE;
is stable during storage at a temperature of 37±5° C. up to at least 2 weeks (preferably at least 4 weeks, more preferably at least 6 weeks, most preferably at least 8 weeks or more), said stability as determined by OD320/OD280 measurement, SE-HPLC, IEX-HPLC, RP-HPLC, potency assay (such as Biacore or ELISA) and/or SDS-PAGE;
is stable when shaking the formulation during 10 s to 1 min;
is stable when pushing the formulation through a needle (25 G, preferably 26 G, more preferably 27 G, even more preferably 28 G, most preferably 29 G or more) with a syringe (the syringe used can be any commercially available syringe, such as e.g. a 1 ml, 2 ml, 3 ml, 4 ml, 5 ml, 10 ml, 20 ml, 30 ml, 40 ml up to 50 ml syringe);
is stable when rotating for two days at 10 rpm; and/or
is stable when stirring for 1 hour at room temperature and/or 2 days at 4° C. at least 10 rpm (such as 50 rpm, 100 rpm or more).

In another aspect, the polypeptide present in the formulation of the invention has a biphasic melting temperature profile wherein one Tm1 is at least 60° C. or more, preferably at least 61° C. or more, more preferably at least 62° C. or more and Tm2 is at least 65° C. or more, preferably at least 66° C. or more, more preferably at least 67° C. or more, as measured by the thermal shift assay and/or differential scanning calorimetry (DSC).

The stability of the formulations of the present invention can be demonstrated by the fact that less than 10% of the polypeptides forms pyroglutamate at the N-terminal glutamic acid (e.g. as assessed by RP-HPLC) and/or less than 25% of the polypeptides forms dimers (e.g. as assessed by SE-HPLC) during storage under one or more of the above stress conditions. Preferably less than 10% of the polypeptides forms pyroglutamate at the N-terminal glutamic acid (e.g. as assessed by RP-HPLC) and less than 25% of the polypeptides forms dimers (e.g. as assessed by SE-HPLC) during storage under one or more of the above stress conditions. More preferably less than 15% of the polypeptides forms dimers (e.g. as assessed by SE-HPLC) during storage under one or more of the above stress conditions.

In a specific aspect, less than 10% of the polypeptides present in the formulation of the invention forms pyroglutamate at the N-terminal glutamic acid (e.g. as assessed by RP-HPLC) during storage at a temperature of 37±5° C. for up to at least 2 weeks (preferably at least 4 weeks, more preferably at least 6 weeks, most preferably at least 8 weeks or more). In another specific aspect, less than 25% of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). In a specific aspect, less than 10% of the polypeptides present in the formulation of the invention forms pyroglutamate at the N-terminal glutamic acid (e.g. as assessed by RP-HPLC) during storage at a temperature of 37±5° C. for up to at least 2 weeks (preferably at least 4 weeks, more preferably at least 6 weeks, most preferably at least 8 weeks or more) and less than 25% of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably less than 15% of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more).

Apart from this and/or in addition, the stability of the formulations of the present invention can be demonstrated by the fact that it shows only low to undetectable levels of aggregation (e.g. as assessed by SE-HPLC, subvisible particle counting, analytical ultracentrifugation, dynamic light scattering, OD320/OD280 ratio measurement and/or elastic light scattering) even during storage under one or more of the above stress conditions. In a specific aspect, the formulations of the present invention show only low to undetectable levels of aggregation (e.g. as assessed by SE-HPLC, subvisible particle counting, analytical ultracentrifugation, dynamic light scattering, OD320/OD280 ratio measurement and/or elastic light scattering) at a temperature of 37±5° C. for up to at least 2 weeks (preferably at least 4 weeks, more preferably at least 6 weeks, most preferably at least 8 weeks or more).

Apart from this and/or in addition, the stability of the formulations of the present invention can be demonstrated by the fact that it shows only low to undetectable levels of fragmentation and/or degradation of the polypeptides (e.g. as assessed by SDS-PAGE, SE-HPLC, RP-HPLC and/or IEX-HPLC) even during storage under one or more of the above stress conditions. In a specific aspect, the formulations of the present invention show only low to undetectable levels of fragmentation and/or degradation of the polypeptides (e.g. as assessed by SDS-PAGE, SE-HPLC, RP-HPLC and/or IEX-HPLC) at a temperature of 37±5° C. for up to at least 2 weeks (preferably at least 4 weeks, more preferably at least 6 weeks, most preferably at least 8 weeks or more).

Apart from this and/or in addition, the stability of the formulations of the present invention can be demonstrated by the fact that it shows very little to no loss of the biological activities (e.g. as assessed by ELISA and/or Biacore) even during storage under one or more of the above stress conditions. In a specific aspect, the formulations of the present invention show very little to no loss of the biological activities (e.g. as assessed by ELISA and/or Biacore) at a temperature of 37±5° C. for up to at least 2 weeks (preferably at least 4 weeks, more preferably at least 6 weeks, most preferably at least 8 weeks or more).

More specifically, in the formulations of the present invention at least 80% (preferably at least 90%, more preferably at least 95%) of the polypeptides preferably retains its binding activity to RANKL (e.g. as assessed by ELISA and/or Biacore) after storage under one or more of the above stress conditions compared to the binding activity prior to storage.

Furthermore, in the formulations of the present invention at least 80% (preferably at least 90%, more preferably at least 95%) of the polypeptides preferably retains its binding activity (e.g. as assessed by ELISA and/or Biacore) to HSA after storage under one or more of the above stress conditions compared to the binding activity prior to storage. In a preferred aspect, at least 80% (preferably at least 90%, more preferably at least 95%) of the polypeptides present in the formulation of the invention retains its binding activity (e.g. as assessed by ELISA and/or Biacore) to RANKL and HSA after storage under one or more of the above stress conditions compared to the binding activity prior to storage.

In a specific aspect, at least 80% (preferably at least 90%, more preferably at least 95%) of the polypeptides retains its binding activity (e.g. as assessed by ELISA and/or Biacore) to RANKL after storage at 37±5° C. for up to at least 2 weeks (preferably at least 4 weeks, more preferably at least 6 weeks, most preferably at least 8 weeks or more) compared to the binding activity prior to storage. In another specific aspect, at least 80% (preferably at least 90%, more preferably at least 95%) of the polypeptides retains its binding activity (e.g. as assessed by ELISA and/or Biacore) to HSA after storage at 37±5° C. for up to at least 2 weeks (preferably at least 4 weeks, more preferably at least 6 weeks, most preferably at least 8 weeks or more) compared to the binding activity prior to storage. Preferably, at least 80% (preferably at least 90%, more preferably at least 95%) of the polypeptides retains its binding activity (e.g. as assessed by ELISA and/or Biacore) to RANKL and HSA after storage at 37±5° C. for up to at least 2 weeks (preferably at least 4 weeks, more preferably at least 6 weeks, most preferably at least 8 weeks or more) compared to the binding activity prior to storage.

Accordingly the present invention provides stable formulations of polypeptides comprising one or more single variable domains (preferably comprising three single variable domains, more preferably comprising two single variable domains that bind RANKL and one single variable domain that binds HSA, such as e.g. SEQ ID NO: 1) at high concentration (as defined herein), wherein less than 10% of the polypeptides forms pyroglutamate at the N-terminal glutamic acid (e.g. as assessed by RP-HPLC) during storage at a temperature of 37±5° C. up to at least 2 weeks (preferably at least 4 weeks, more preferably at least 6 weeks, most preferably at least 8 weeks or more);

less than 25% of the polypeptides forms dimers (e.g. as assessed by SE-HPLC) during storage at a temperature of 37±5° C. up to at least 2 weeks (preferably at least 4 weeks, more preferably at least 6 weeks, most preferably at least 8 weeks or more);

at least 80% of the polypeptides retain their binding activity (e.g. as assessed by ELBA and/or Biacore) to at least one of their (preferably to all of their) targets after storage at 37±5° C. up to 2 weeks (preferably at least 4 weeks, more preferably at least 6 weeks, most preferably at least 8 weeks or more) compared to the binding activity prior to storage; and/or the polypeptide is stable under mechanical stress.

In a specific aspect of the invention, such formulations are homogeneous. In another aspect, the formulations of the invention are sterile. In addition to the polypeptide of the invention at high concentration (as defined above), the formulations of the present invention comprise at least an aqueous carrier (e.g. distilled water, MilliQ water or WFI) and a buffer. Preferably the pH of the formulation of the invention is in the range of 5.5 to 7.0, most preferably the pH is 7.0. Preferred buffers for use in the formulation of the invention are phosphate buffers or acetate buffers. The buffer is preferably at a concentration of about 10 to 20 mM. In a specific aspect, the formulation of the invention comprises a phosphate buffer (such as disodium hydrogen phosphate/ $Na_2HPO_4$) pH 7.0 at a concentration of 10 mM. In another specific aspect, the formulation of the invention comprises an acetate buffer pH 5.5 at a concentration of 10 mM.

Accordingly, the present invention provides stable formulations of polypeptides comprising one or more single variable domains, said formulations comprising an aqueous carrier, the polypeptide at a concentration from about 30450 mg/ml, such as at least 30 mg/ml, at least 40 mg/ml, at least 50 mg/ml or at least 60 mg/ml, preferably at least 65 mg/ml or at least 70 mg/ml, more preferably at least 80 mg/ml or at least 90 mg/ml, even more preferably at least 100 mg/ml or more and a buffer such as a phosphate or acetate buffer at a concentration of about 10-20 mM and with a pH ranging from 5.5 to 7.0. Of course, it is evident that the same buffer solution can also contain lower concentrations of the polypeptide of the invention such as e.g. from 1 to 10 mg/ml or from 1 to 20 mg/ml such as 1 mg/ml, 2 mg/ml, 5 mg/ml, 10 mg/ml, 15 mg/ml or 20 mg/ml, which concentrations may for example be useful in other forms of administration, such as other forms of parenteral administration (such as e.g. intravenous, intramuscular, intracranial, etc.).

Preferably the formulation of the invention is isotonic or slightly hypotonic and/or has an osmolality of about 290±60 mOsm/kg, such as about 240 or higher, 250 or higher or 260 or higher. Accordingly, the formulation of the invention may further comprise a salt such as e.g. NaCl at a concentration in the range from about 0 mM to about 200 mM, preferably 100 mM to 150 mM, such as around 115 mM.

In another specific aspect, the formulations of the invention comprise surfactants (e.g., Tween20 or Tween80) at a concentration in the range of about 0% to about 0.1% (v:v), such as e.g. 0.01% (v:v).

Accordingly, a preferred formulation of the invention may comprise:

30-150 mg/ml of SEQ ID NO: 1;
10-20 mM disodium hydrogen phosphate ($Na_2HPO_4$);
100-150 mM Sodium chloride (NaCl);
0-0.1% Tween80 (v:v), such as e.g. 0.01% Tween80 (v:v).

An example and preferred formulation of the invention comprises 65 mg/ml of SEQ ID NO: 1, 10 mM disodium hydrogen phosphate ($Na_2HPO_4$), 115 mM Sodium chloride (NaCl) and 0.01% Tween80 (v:v).

In a preferred aspect, the formulation of the invention is a pharmaceutical formulation.

The present invention further provides methods for preparing the stable formulations of the invention. The methods of the invention may comprise the steps of concentrating a polypeptide comprising one or more single variable domains and exchanging it with the preferred buffer.

The invention also relates to the lyophilization and spray drying of the formulations of the invention and to the lyophilized and spray dried formulation obtained as such.

Also provided are containers, kits and pharmaceutical unit dosages comprising the formulations of the invention for use by, e.g., a healthcare professional. In specific embodiments, the kits or pharmaceutical unit dosages comprising the stable formulations of the invention are formulated for parenteral administration (e.g., intradermally, intramuscularly, intraperitoneally, intravenously and subcutaneously) of the polypeptide of the invention to a human subject. Preferably the kits and/or pharmaceutical unit dosages are formulated for subcutaneous administration of the polypeptide of the invention to a human subject.

The formulations, containers, pharmaceutical unit dosages and/or kits can be used in prophylaxis and/or therapy. In a specific aspect, the formulations, containers, pharmaceutical unit dosages and/or kits are used for the prevention and/or treatment of bone diseases and/or disorders such as osteoporosis, cancer-related bone diseases, and/or bone loss associated with autoimmunity and/or viral infection.

FIGURE LEGENDS

FIG. 1. Overlay of the A280 nm SE-HPLC profiles of RANKL008a P#110708 after 3 months at 5° C. in PBS (A), Phosphate buffer (B) and Acetate buffer (C). Inset, 214 nm zoom on the main peak and the side peaks.

Figure 2:
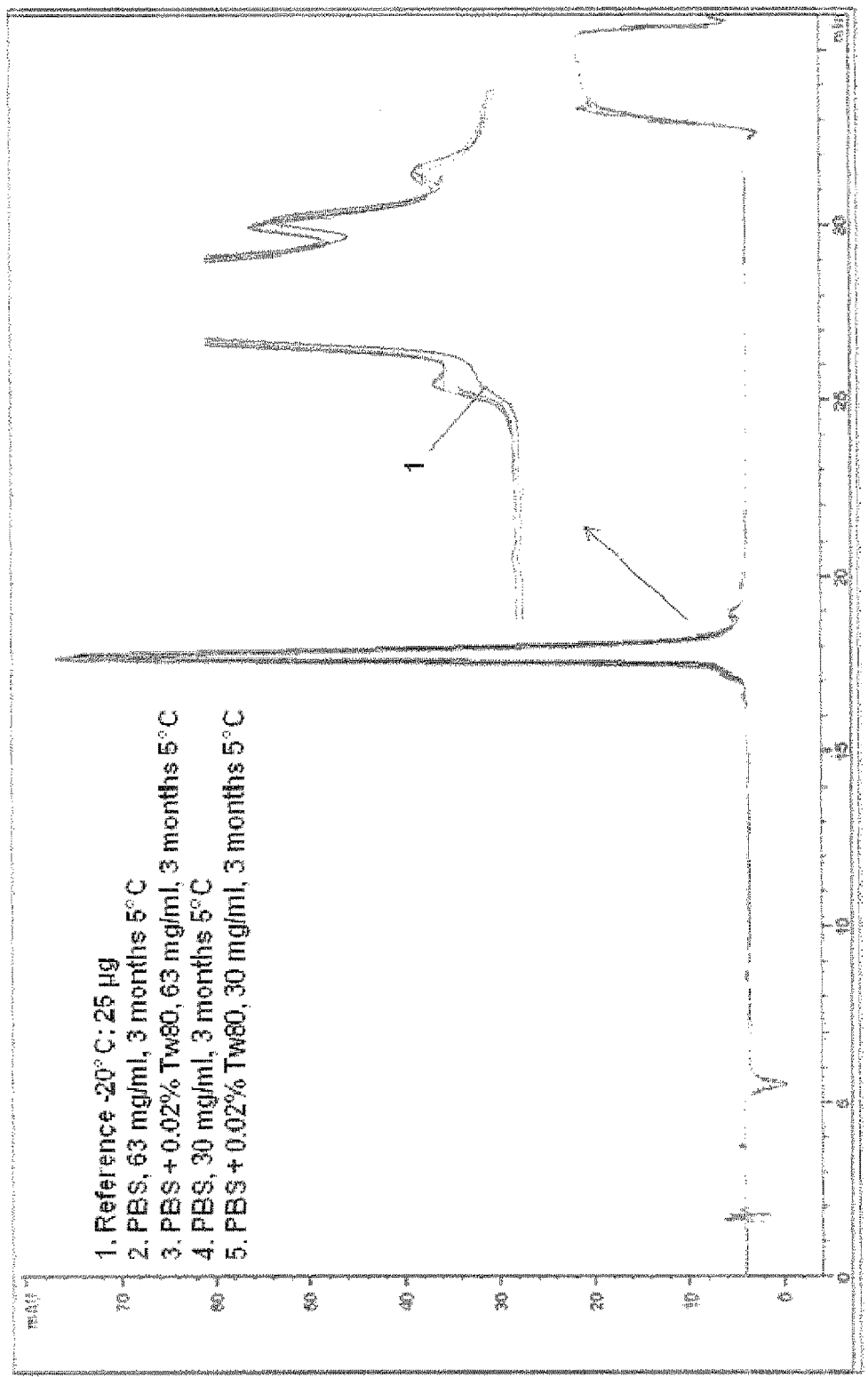
Figure 2:
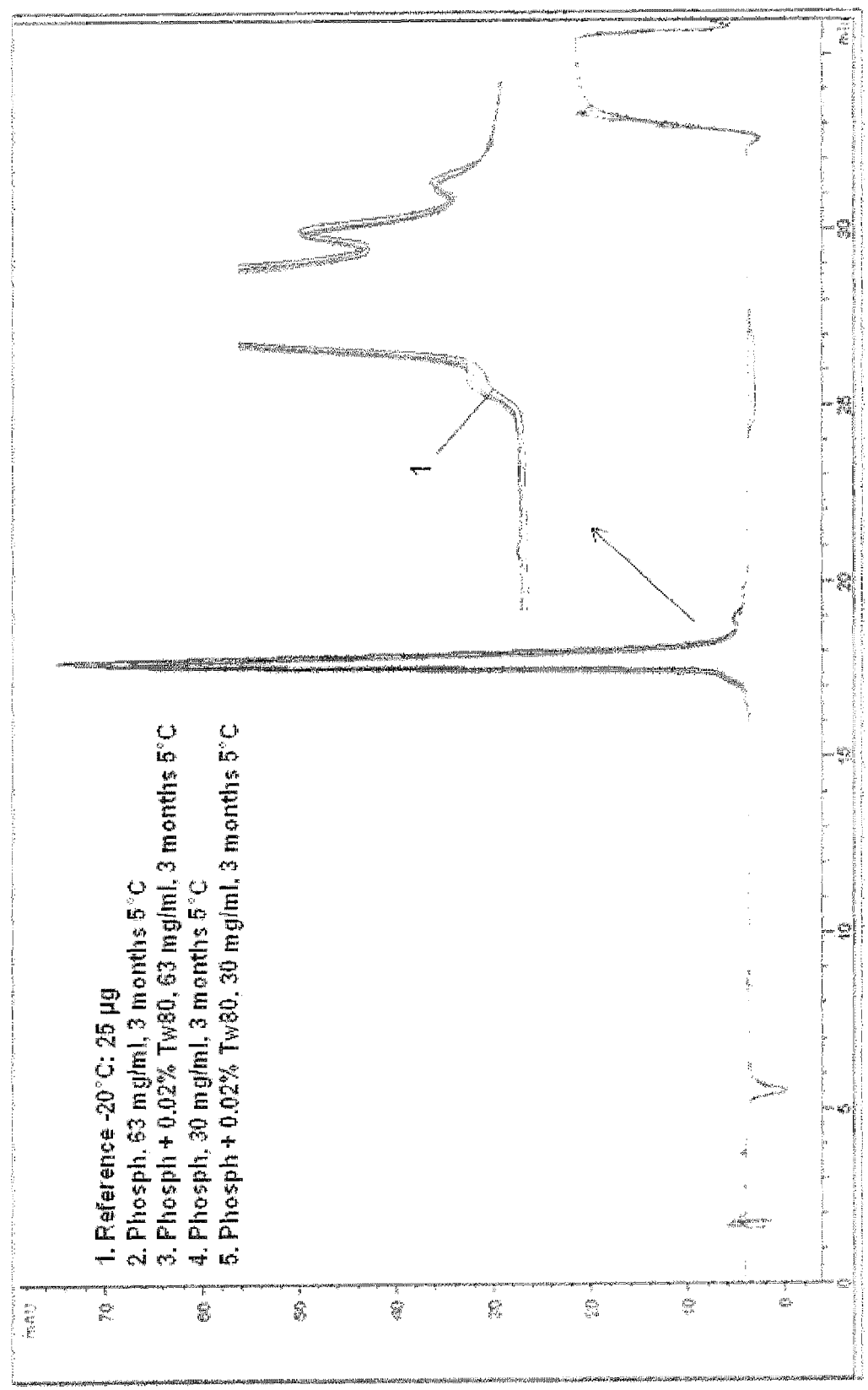
Figure 2:
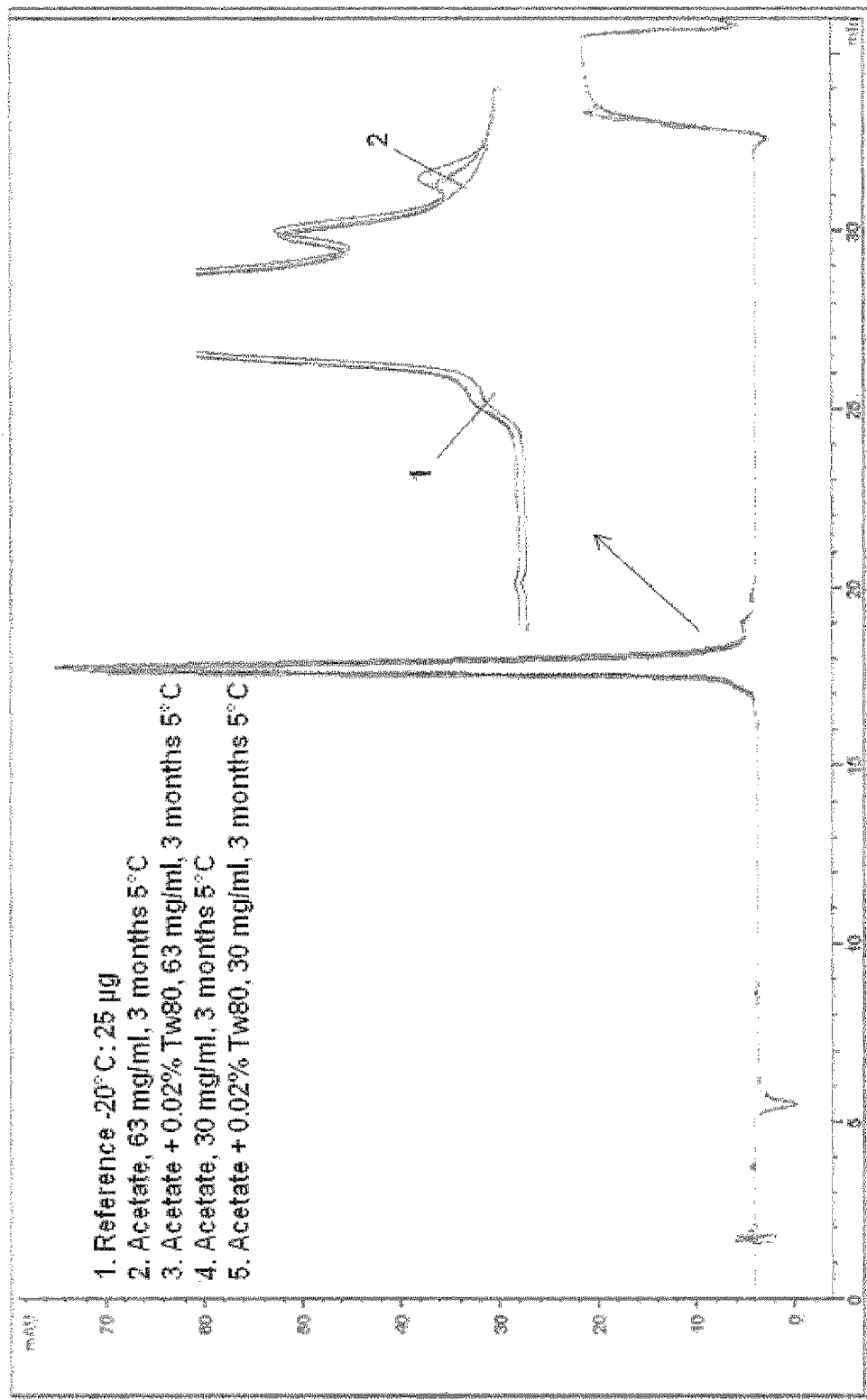

FIG. 2. Overlay of the A280 nm RP-HPLC profiles of RANKL008a P#110708 after 3 months at 5° C. in PBS (A), Phosphate buffer (B) and Acetate buffer (C). Inset, zoom on the main peak and the side peaks.

Figure 3:
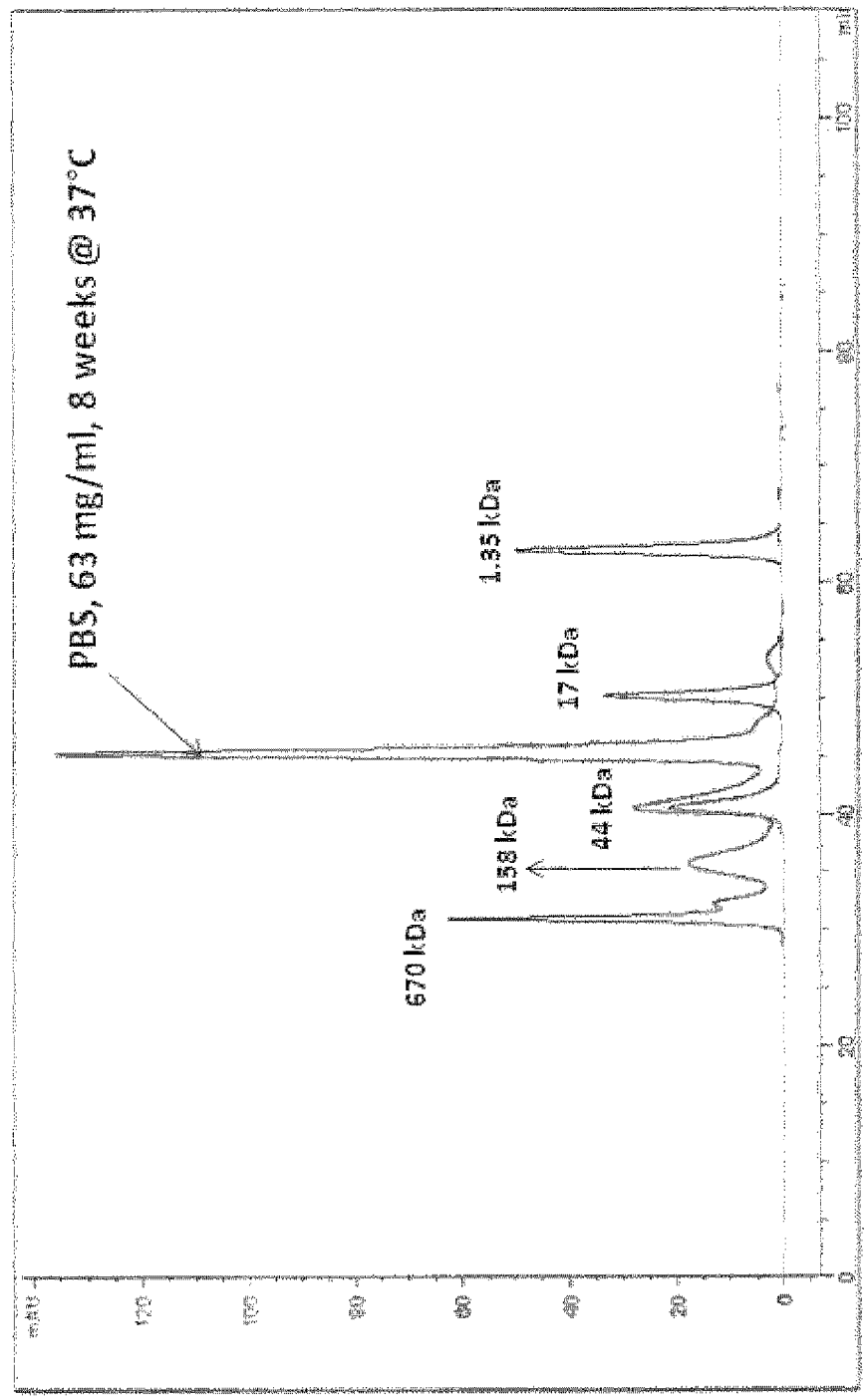

FIG. 3. Overlay of the SE-HPLC profiles of the gel filtration marker and RANKL008a (63 mg/ml) after 8 weeks at 37° C. in PBS (as described in Example 4.1).

Figure 4:
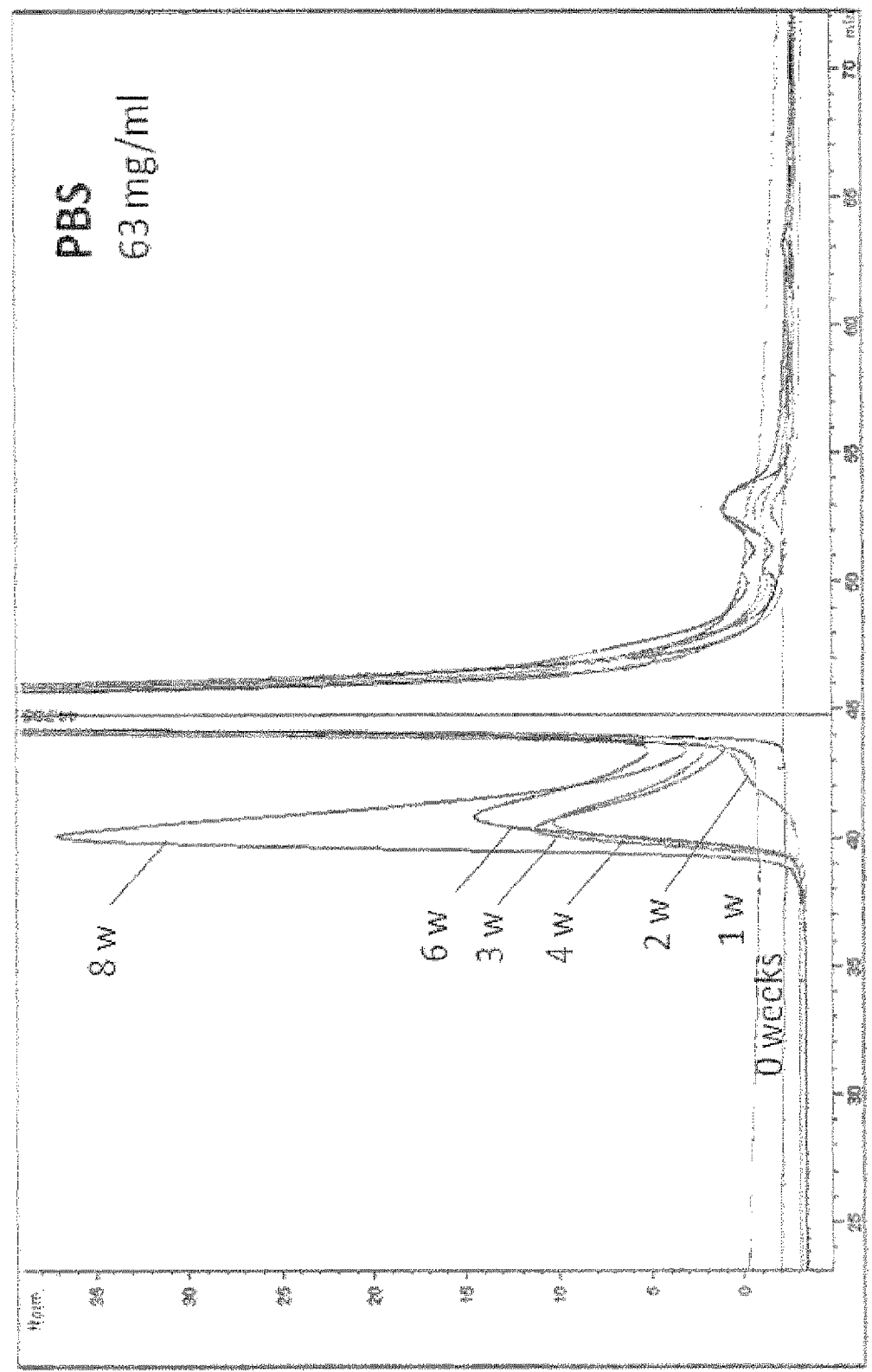

FIG. 4. Overlay and zoom of the A280 nm SE-HPLC chromatograms of RANKL008a incubated up to 8 weeks at 37° C. in PBS buffer. Time-dependent increase in the surface area of the prepeak (w=weeks).

Figure 5:
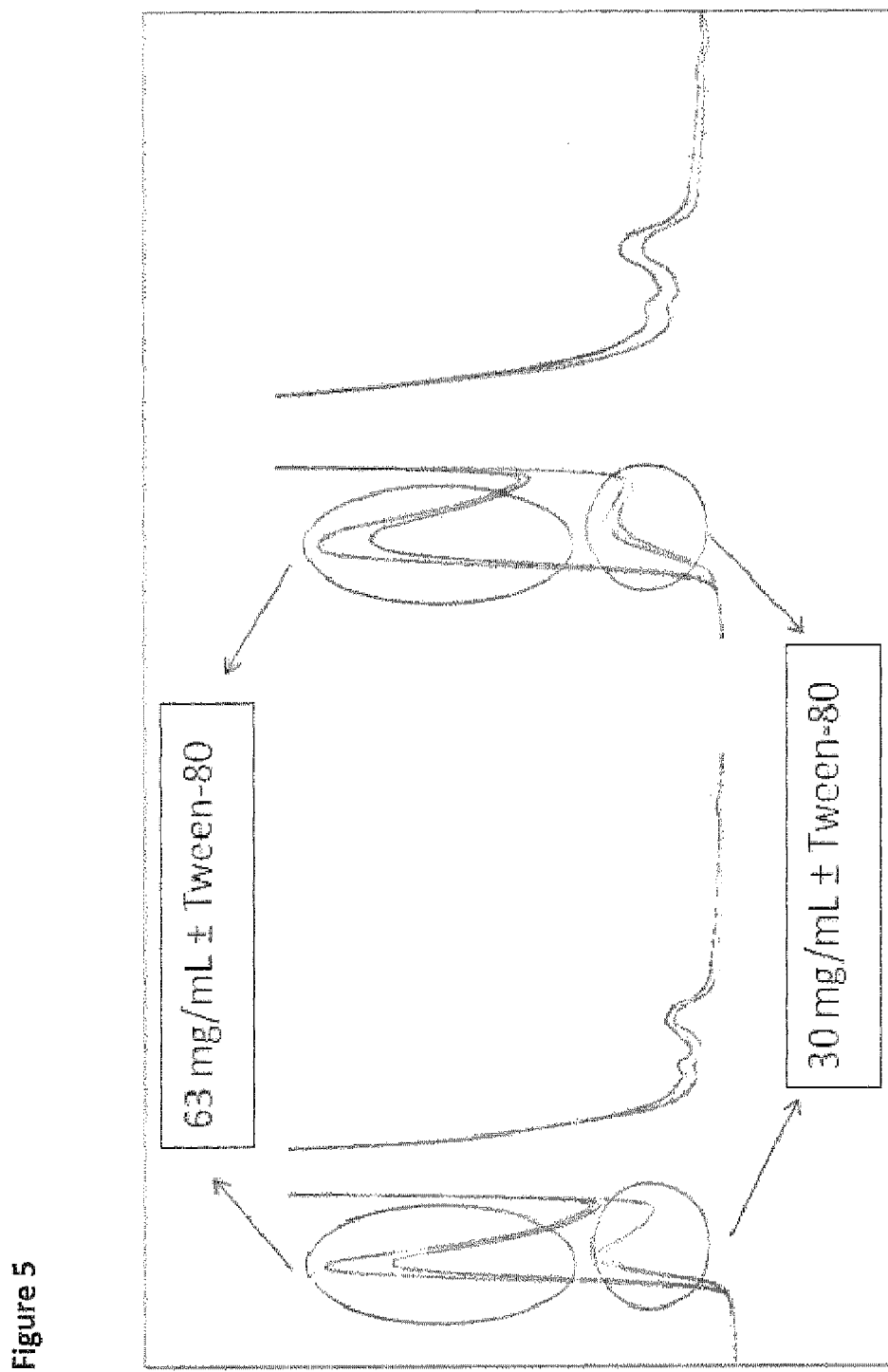

FIG. 5. Overlay and zoom of the A280 nm SE-HPLC chromatograms of RANKL008a (30 mg/ml and 63 mg/ml) incubated 6 weeks in PBS buffer (with and without Tween80) at 37° C. The formation of dimers is concentration-dependent.

Figure 6:
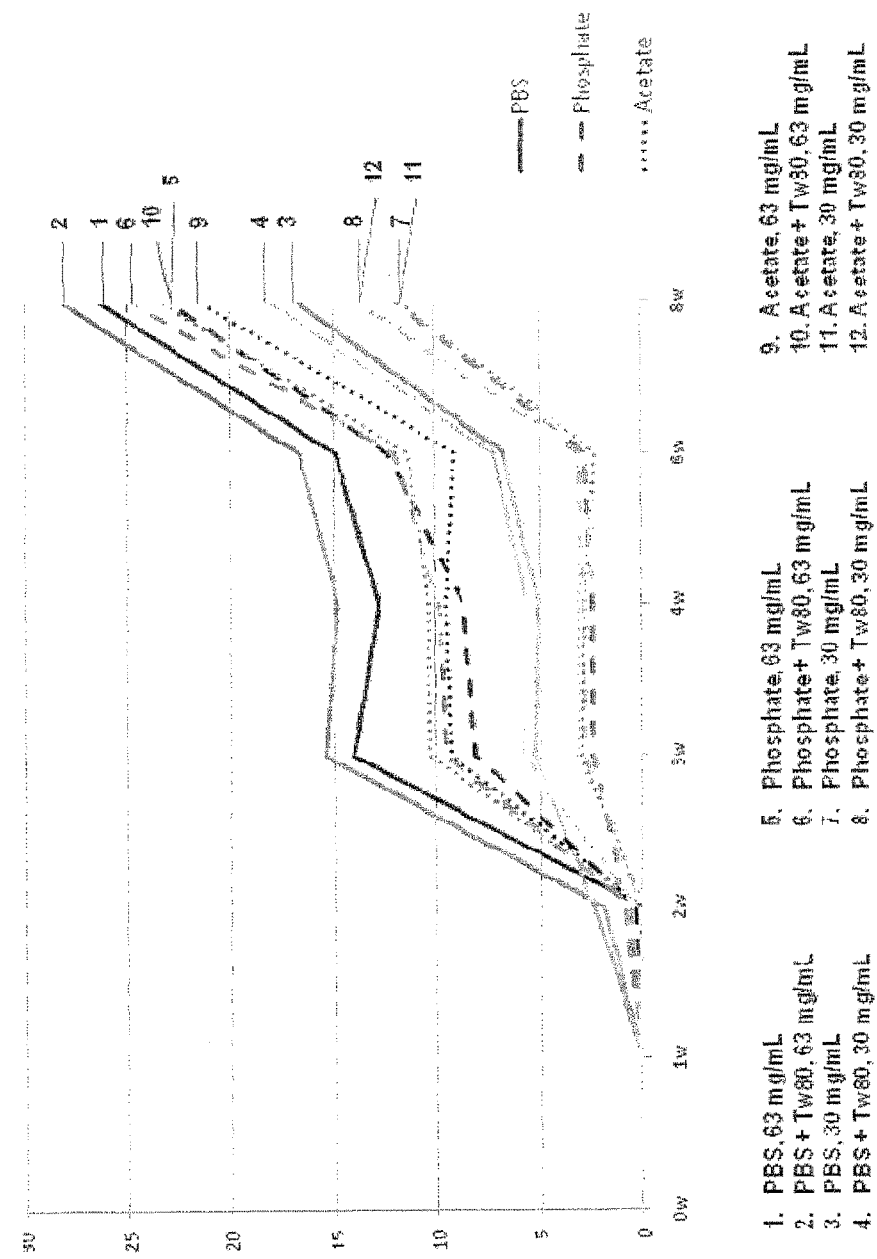

FIG. 6. Graph illustrating the time- and concentration-dependent increase in the formation of dimers as observed during SE-HPLC analysis of the stability samples stored at 37° C.

Figure 7:
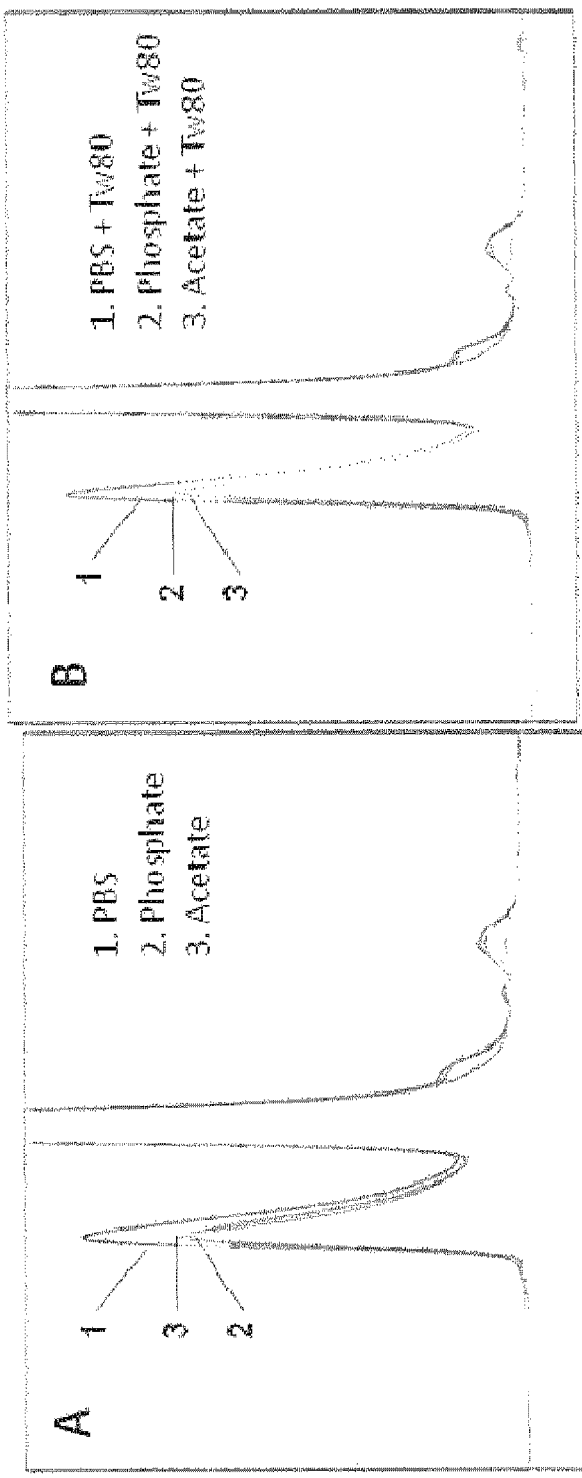

FIG. 7. Overlay and zoom of the A280 nm SE-HPLC chromatograms of RANKL008a incubated at 37° C. The data for the 63 mg/ml samples stored for 8 weeks are given in buffers without Tween80 (A) and buffers with 0.02% Tween80 (v:v) (B).

Figure 8:
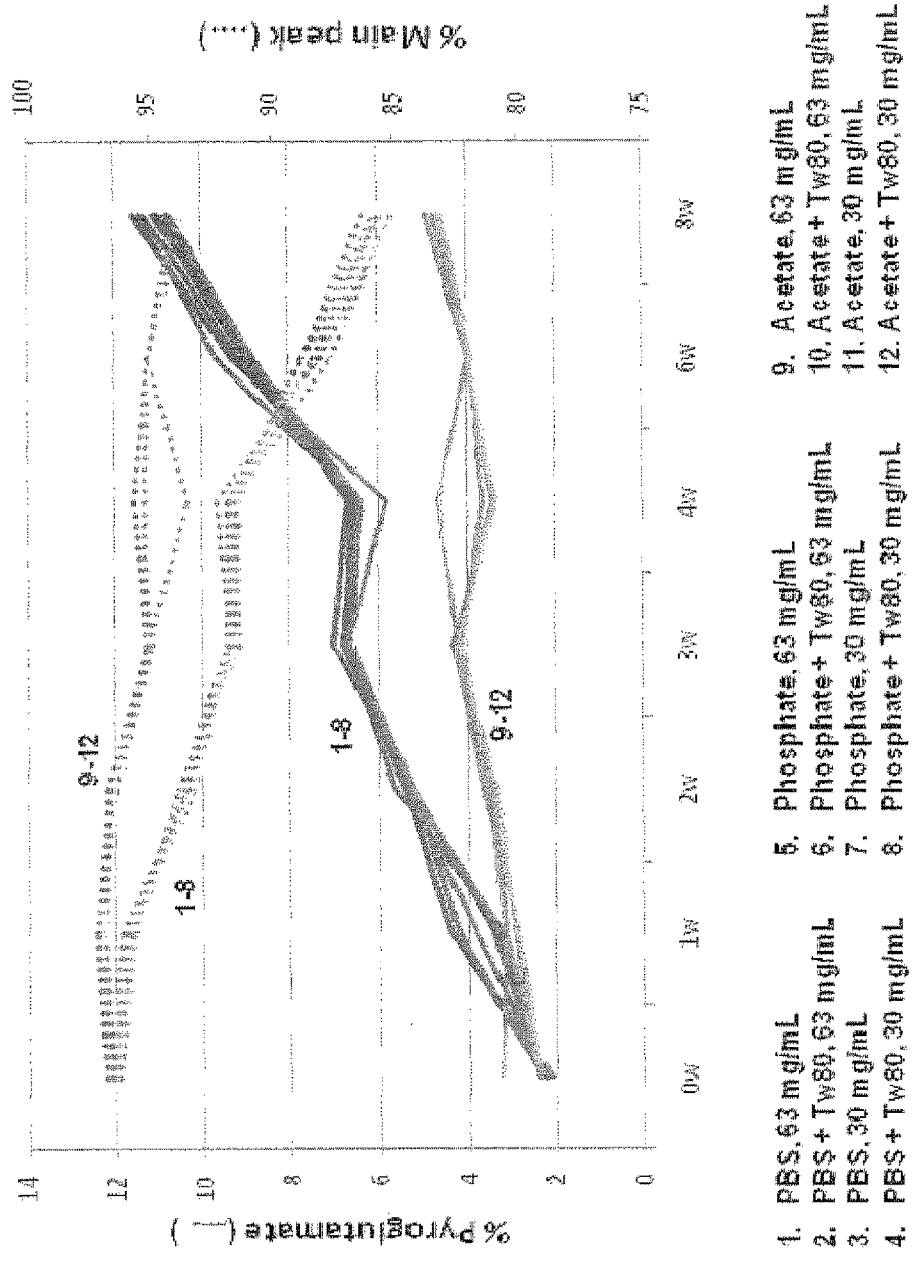

FIG. 8. Time-dependent increase in the pyroglutamate peak surface area (solid line) and the decrease of the main peak surface area (dotted line) for the different RANKL008a samples stored up to 8 weeks at 37° C. Values are represented as % of the total integrated surface area. Note that pyroglutamate is formed much slower in acetate than in PBS and phosphate.

Figure 9:
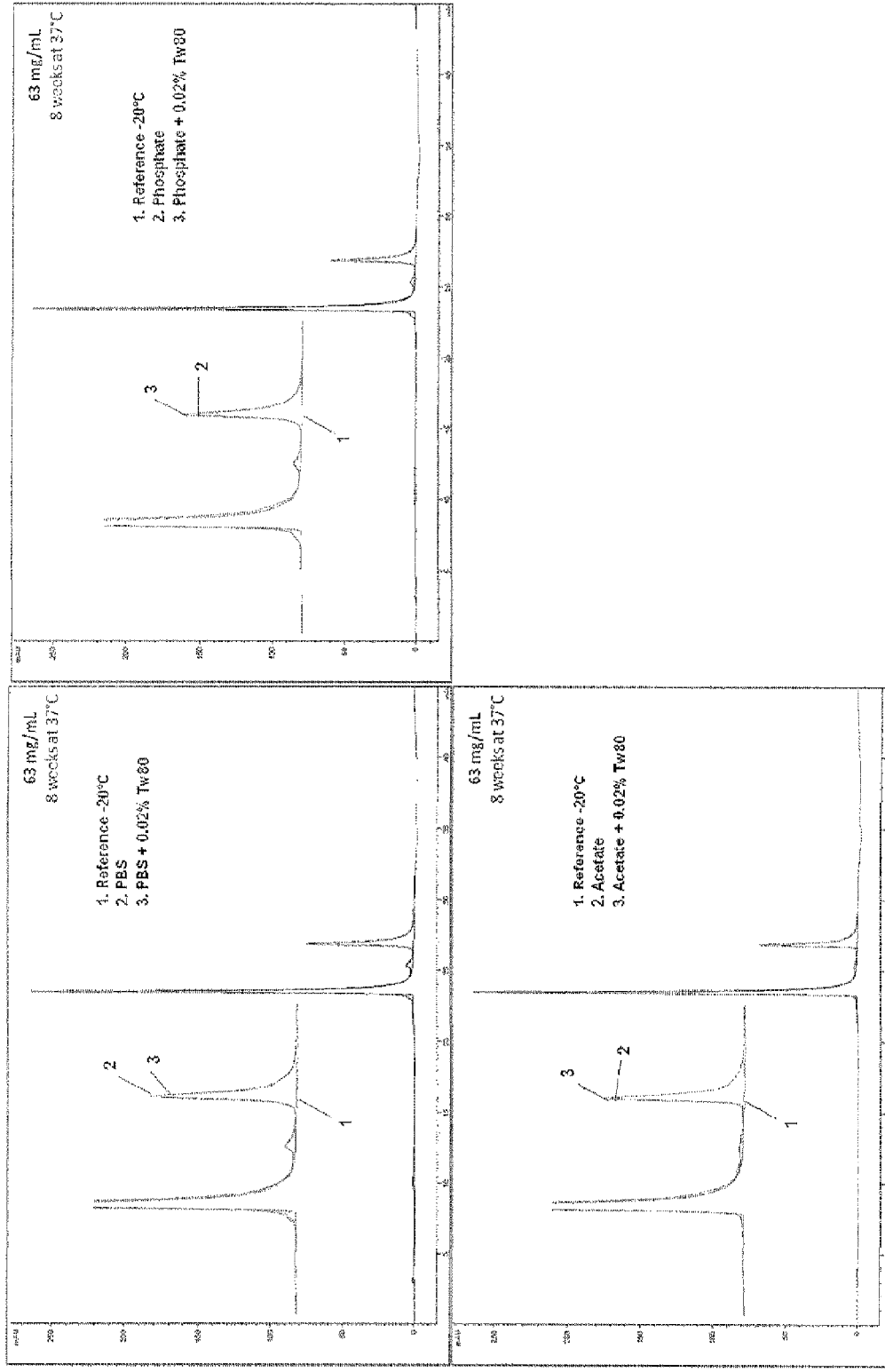
Figure 9:
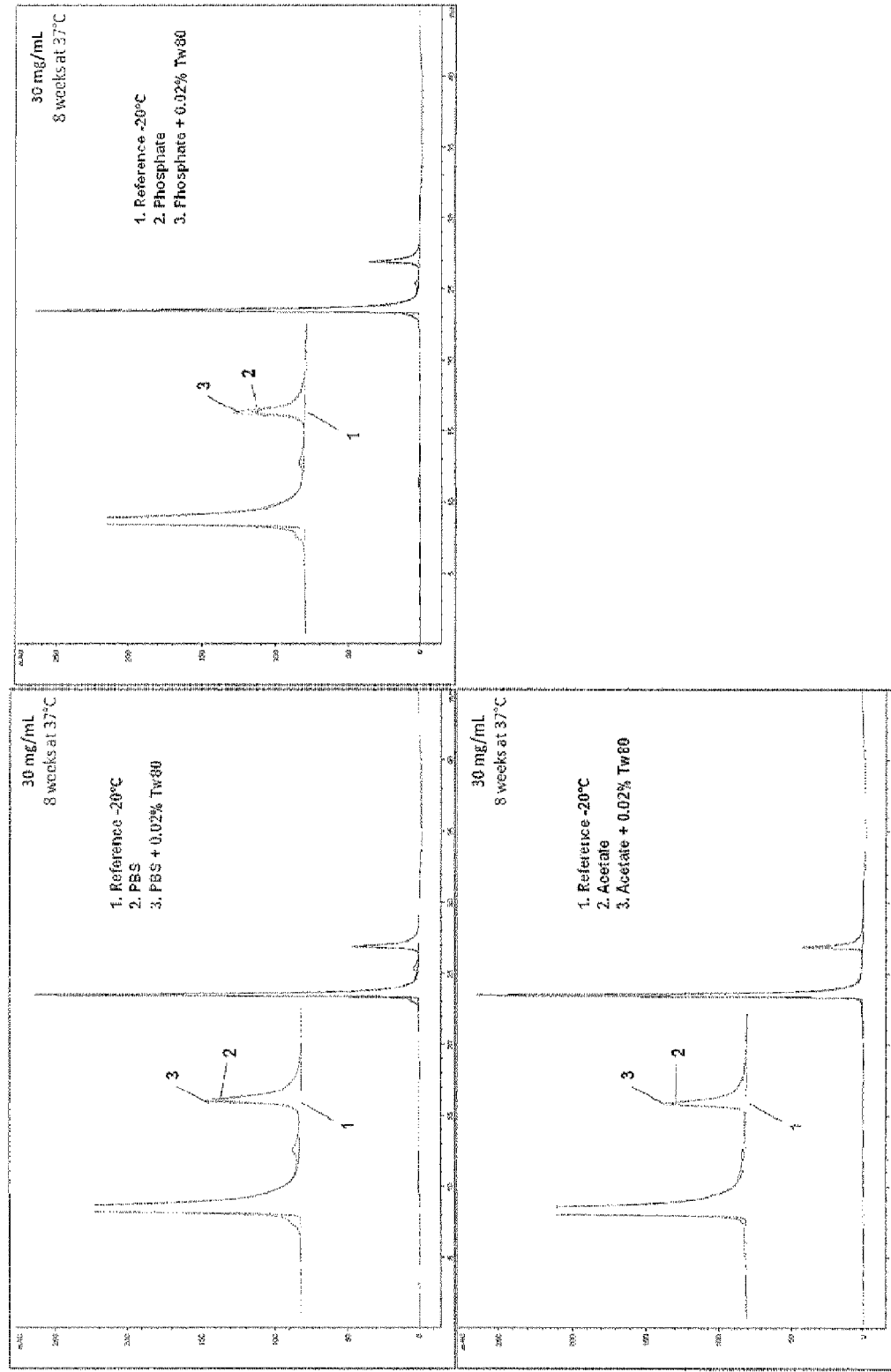

FIG. 9. Overlay of the IEX-HPLC chromatograms of RANKL008a incubated for 8 weeks at 37° C. at 63 mg/ml (A) or 30 mg/ml (B). The surface area of the post-peak was lowest in acetate buffer and somewhat higher at higher protein concentration.

Figure 10:
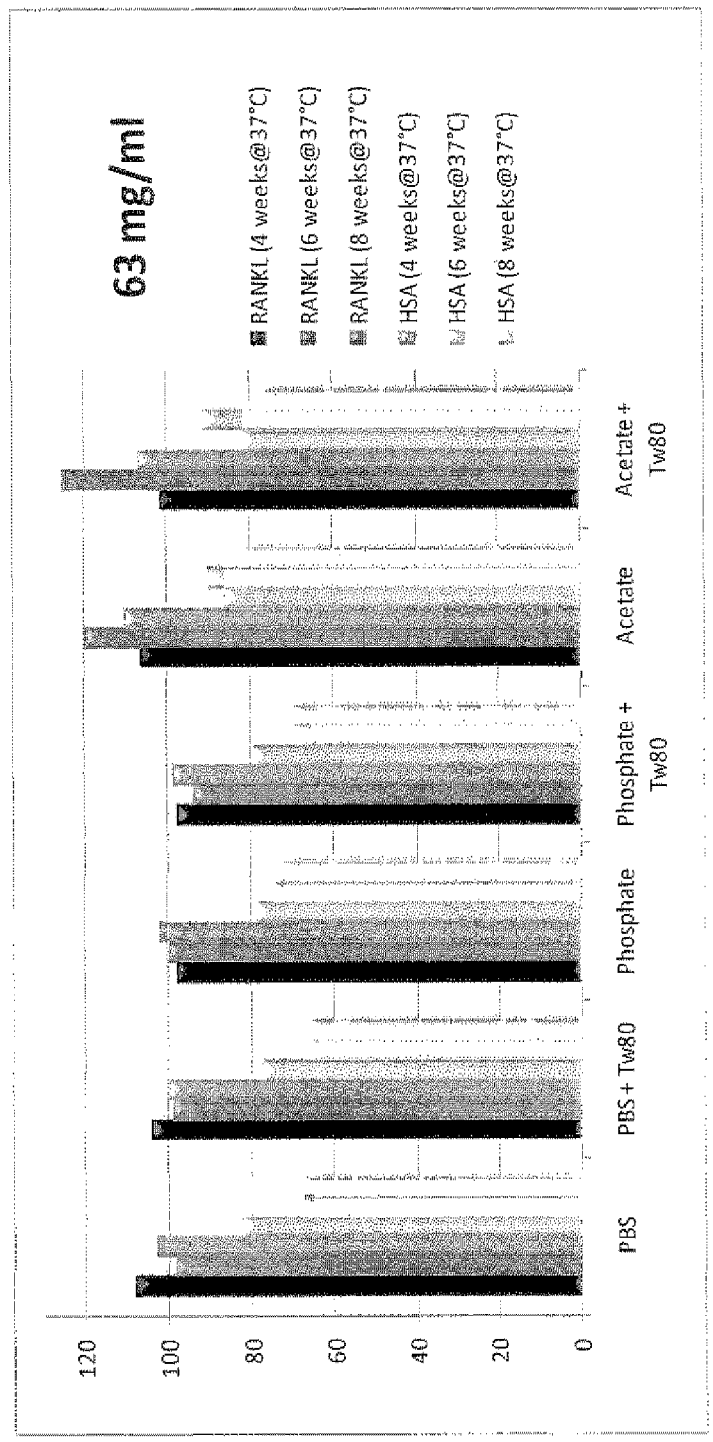
Figure 10:
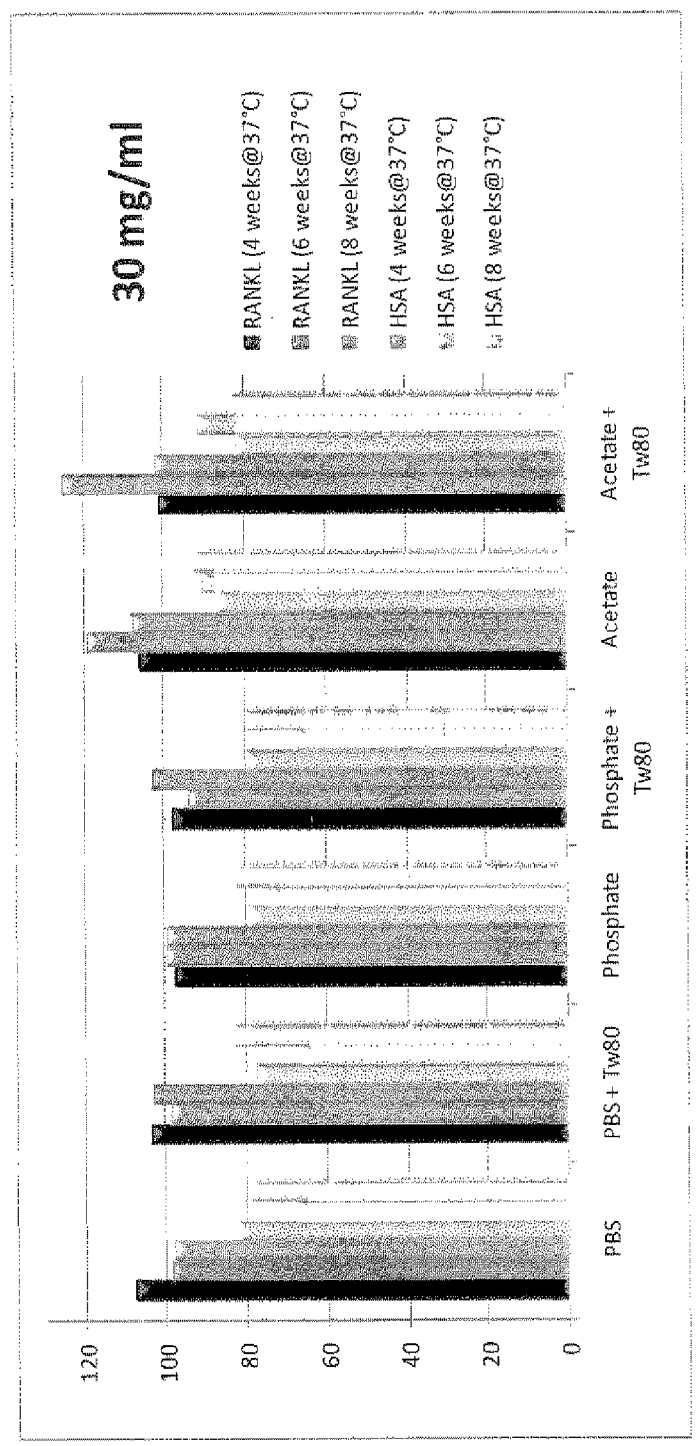

FIG. 10. Biacore analysis of the stressed RANKL008a samples at 63 mg/ml (A) and 30 mg/ml (B). The % activity is shown in relation to the unstressed samples (0 weeks). The apparent increase in activity for some samples is most likely due to evaporation of the sample during incubation at 37° C.

FIG. 11. SDS-PAGE analysis and Krypton IR staining of the different stressed RANKL008a samples. Lane 1: MW marker (Bio-Rad #161-0374), lanes 2-9: RANKL008a subjected to one freeze/thaw cycle (F/T) and stored for 0-8 weeks (w) at 37° C. Buffer conditions are indicated on the graphs. R: reducing conditions, NR: non-reducing conditions.

Figure 12:
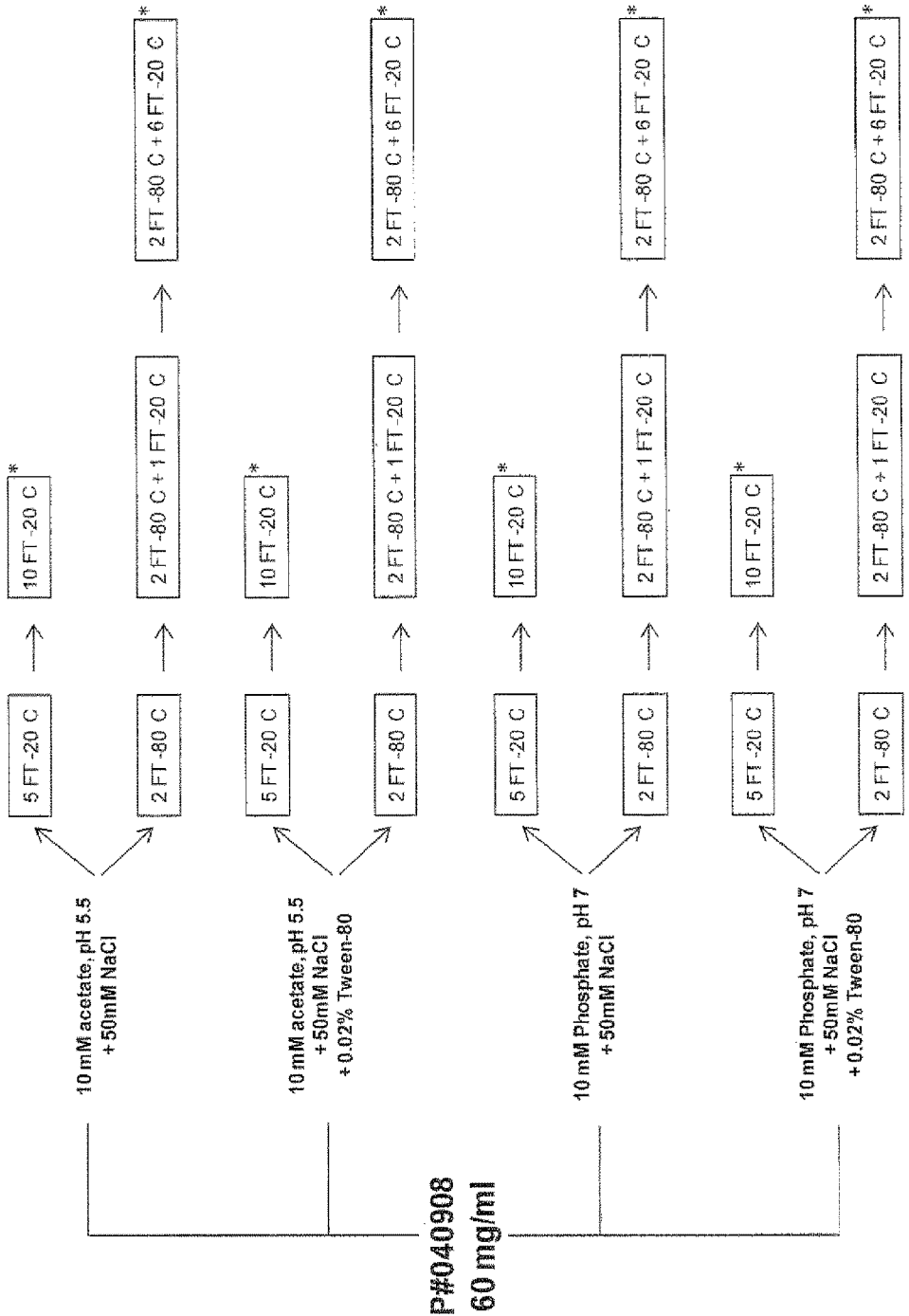

FIG. 12. Schematic overview of the freeze/thaw studies that were performed with RANKL008a at 60 mg/ml. The Nanobody was formulated in four different buffers and subjected to two different freeze/thaw strategies, with the first freeze/thaw cycles (FT) at either −20° C. or −80° C. Each box represents the stage at which analysis by RP-HPLC, SE-HPLC and IEX-HPLC were performed. Biacore analysis and the potency assay were performed on the end samples indicated with *.

Figure 13:
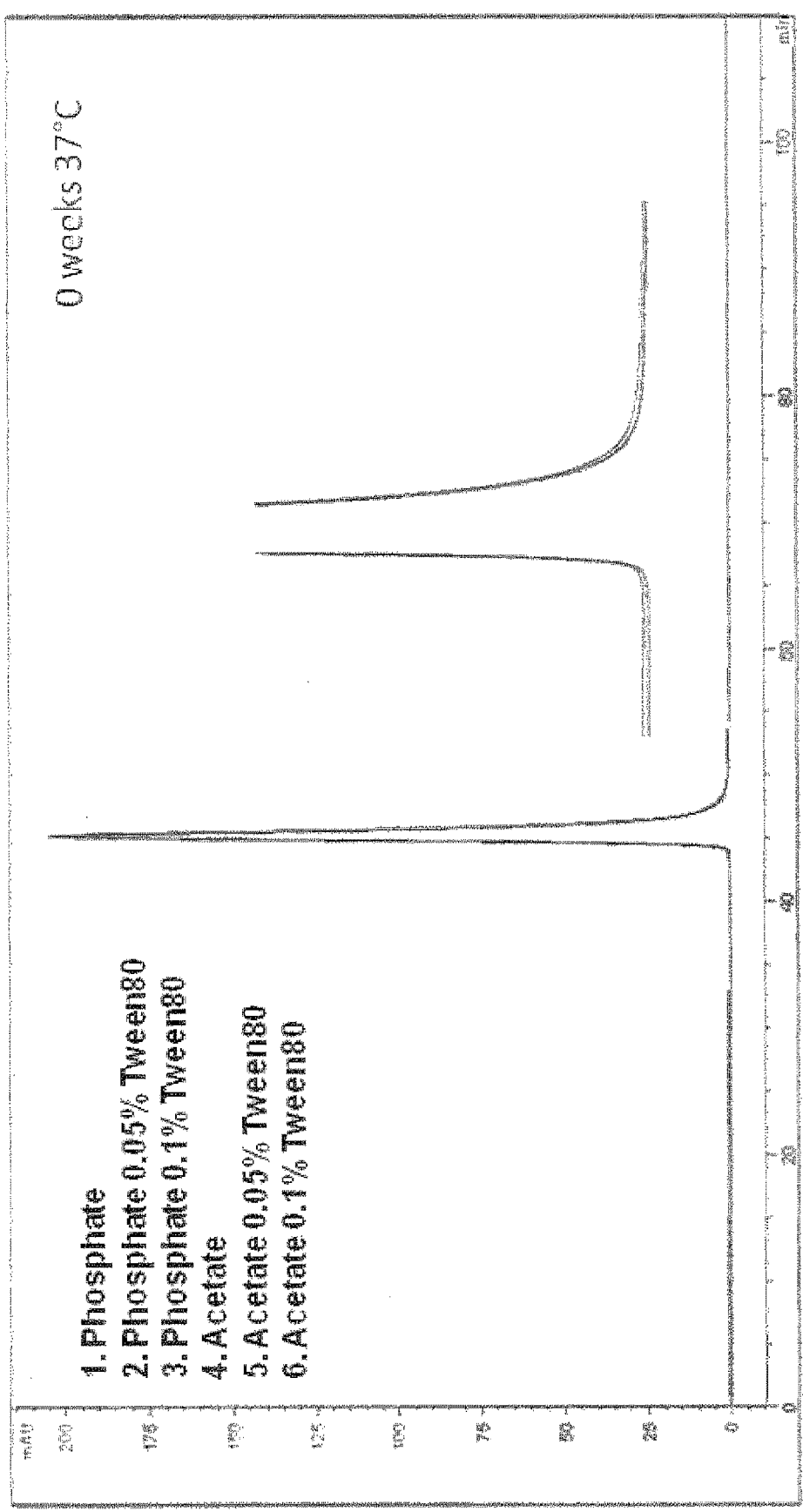
Figure 13:
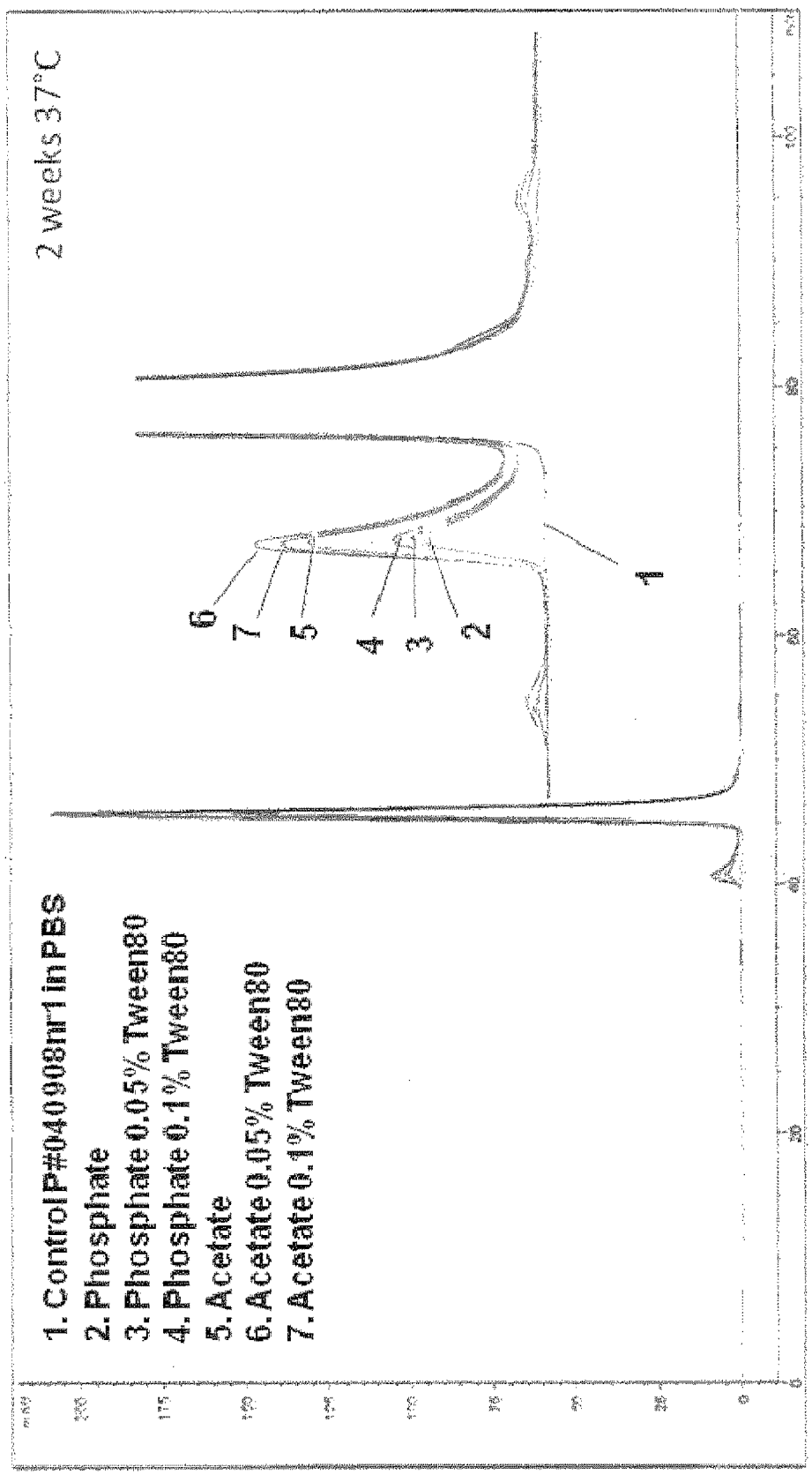
Figure 13:
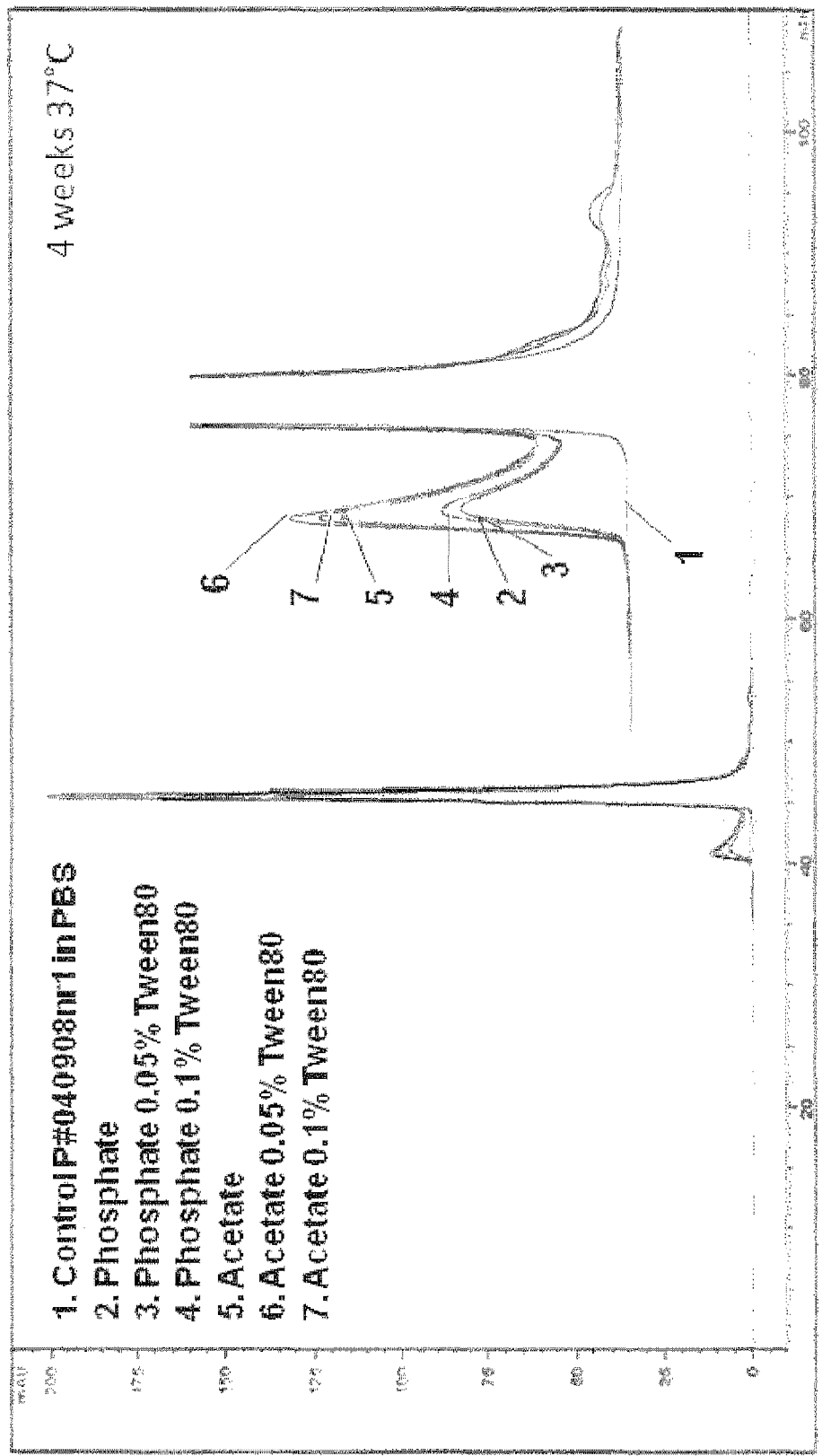

FIG. 13. Overlay of the SE-HPLC chromatograms of lyophilized RANKL008a, (A) directly after reconstitution (0 weeks at 37° C.) and after storage for (B) 2 and (C) 4 weeks at 37° C.

Figure 14:
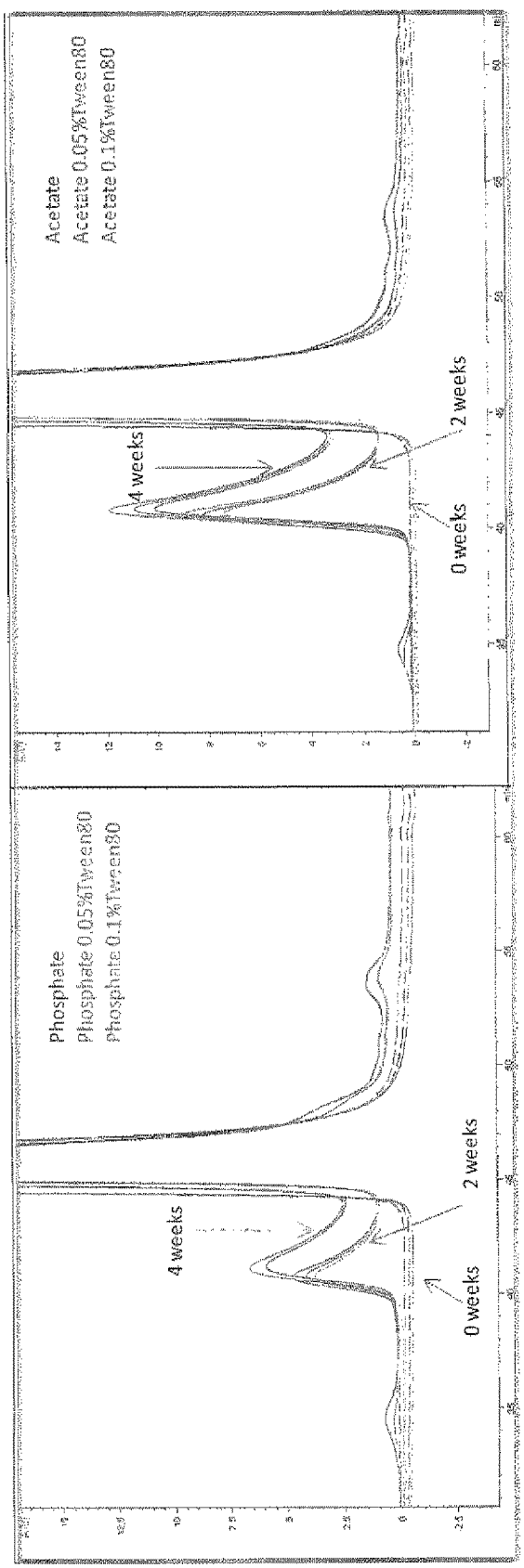

FIG. 14. Overlay of the SE-HPLC chromatograms of lyophilized RANKL008a stored at 37° C. This figure demonstrates the time-dependent formation of dimers in stressed, lyophilized samples of RANKL008a formulated in acetate buffer or phosphate buffer. No apparent effect of the addition of Tween80 can be seen.

Figure 15:
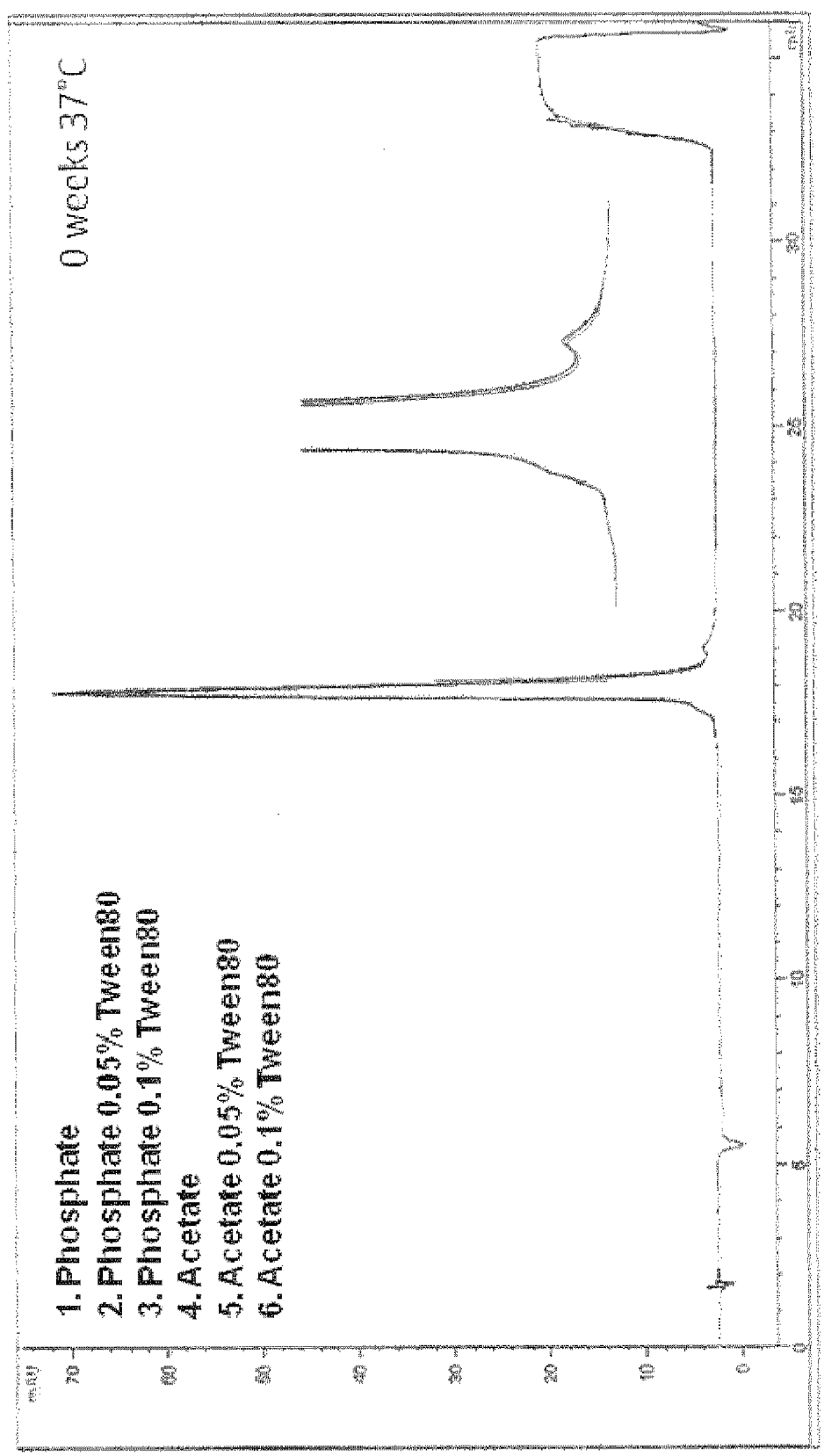
Figure 15:
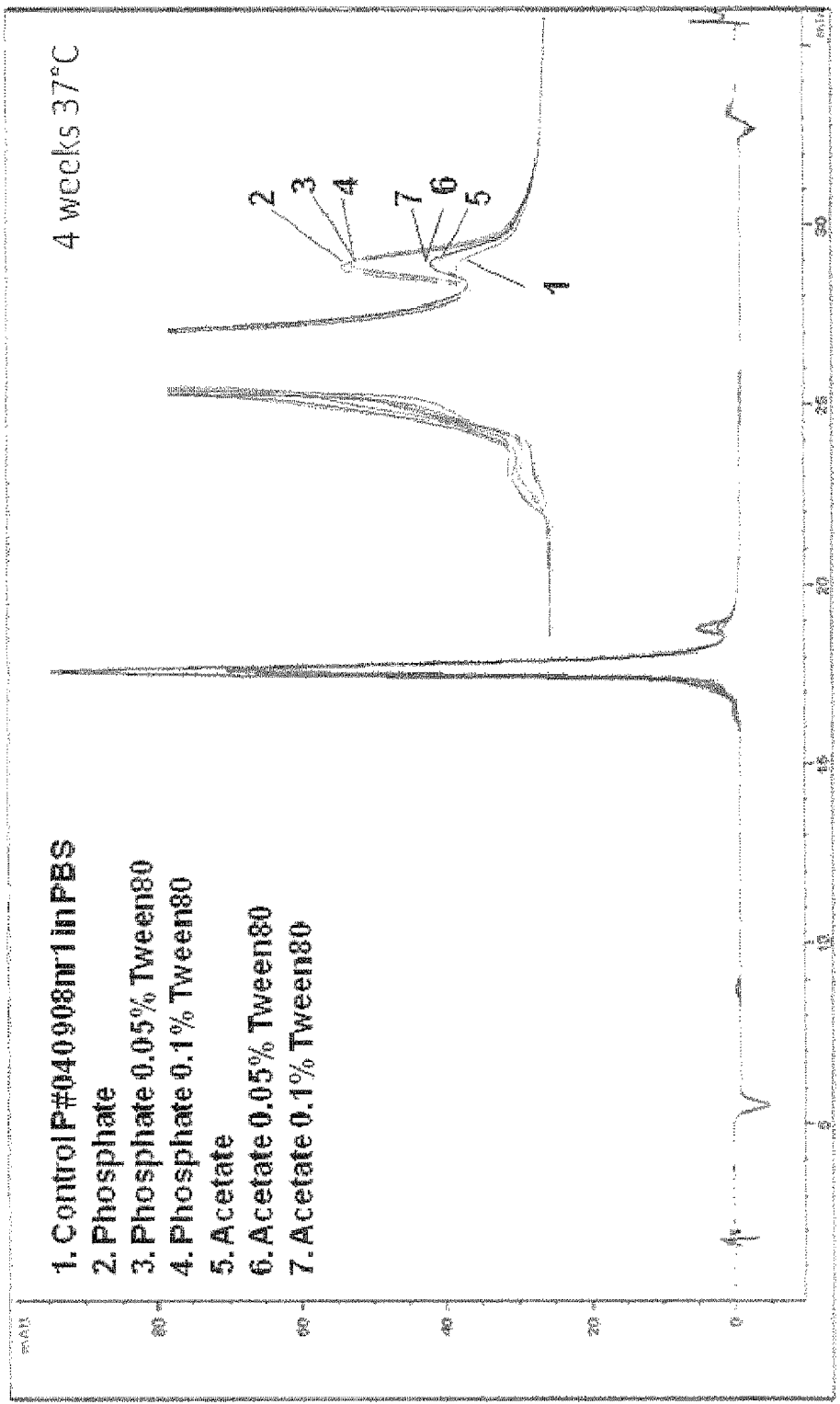

FIG. 15. Overlay of the RP-HPLC chromatograms of lyophilized RANKL008a, (A) directly after reconstitution and (B) after storage at 37° C. for 4 weeks.

Figure 16:
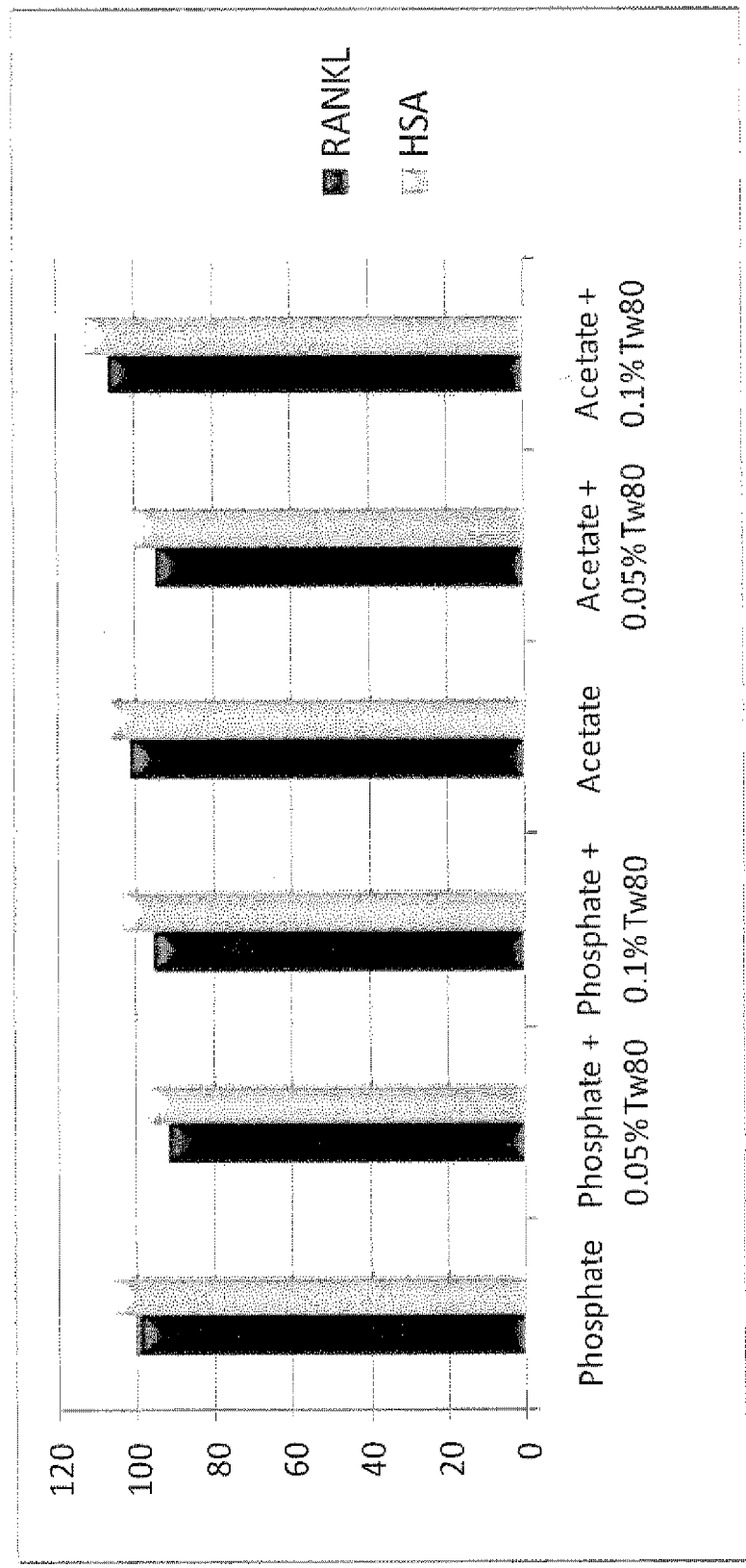

FIG. 16. The RANKL and HSA binding activity of lyophilized and reconstituted RANKL008a relative to the activities before lyophilization.

Figure 17:
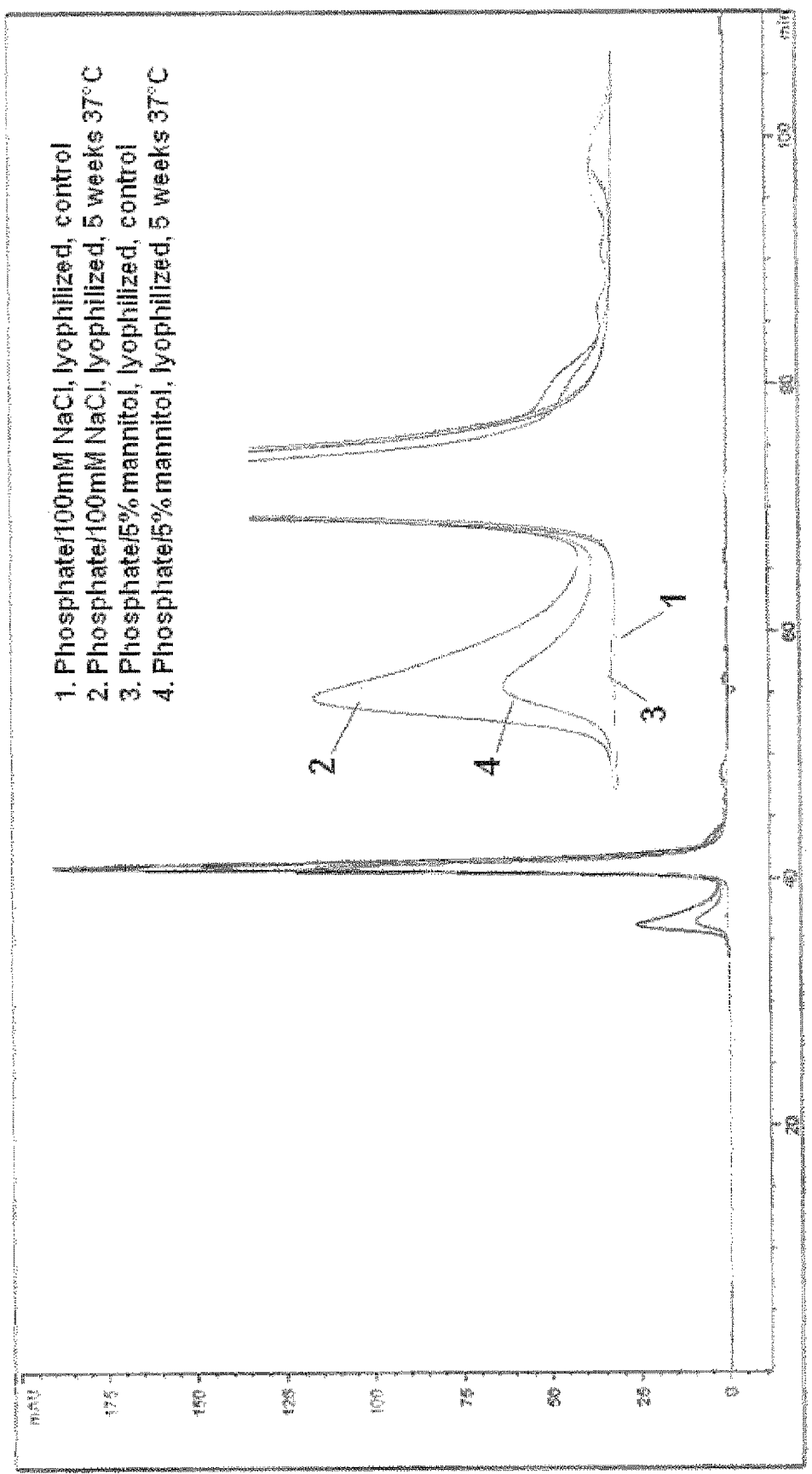

FIG. 17. The A280 nm SE-HPLC chromatograms of lyophilized RANKL008a in 10 mM Phosphate, pH 7+100 mM NaCl or 10 mM Phosphate, pH 7+5% mannitol, after incubation for 0 and 5 weeks at 37° C. A zoom on the main peak is shown as inset.

Figure 18:
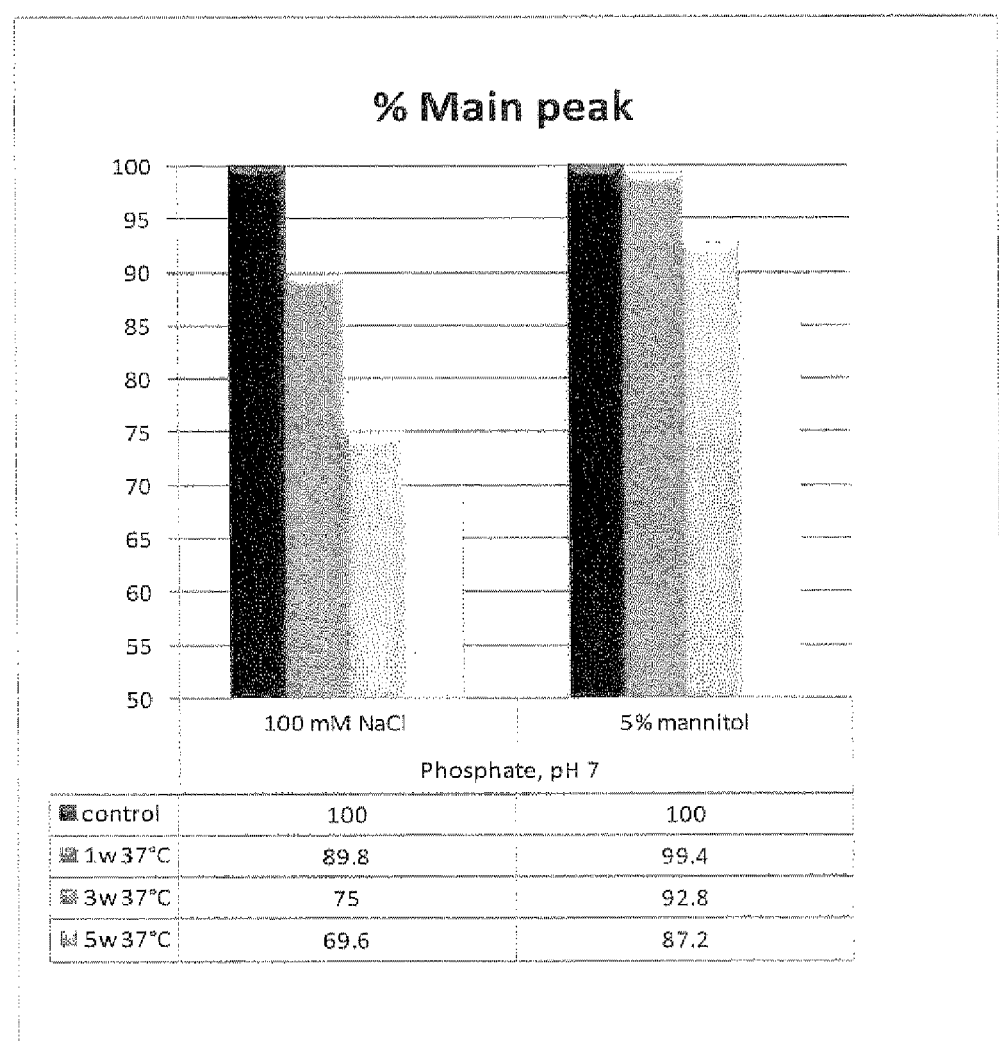
Figure 18:
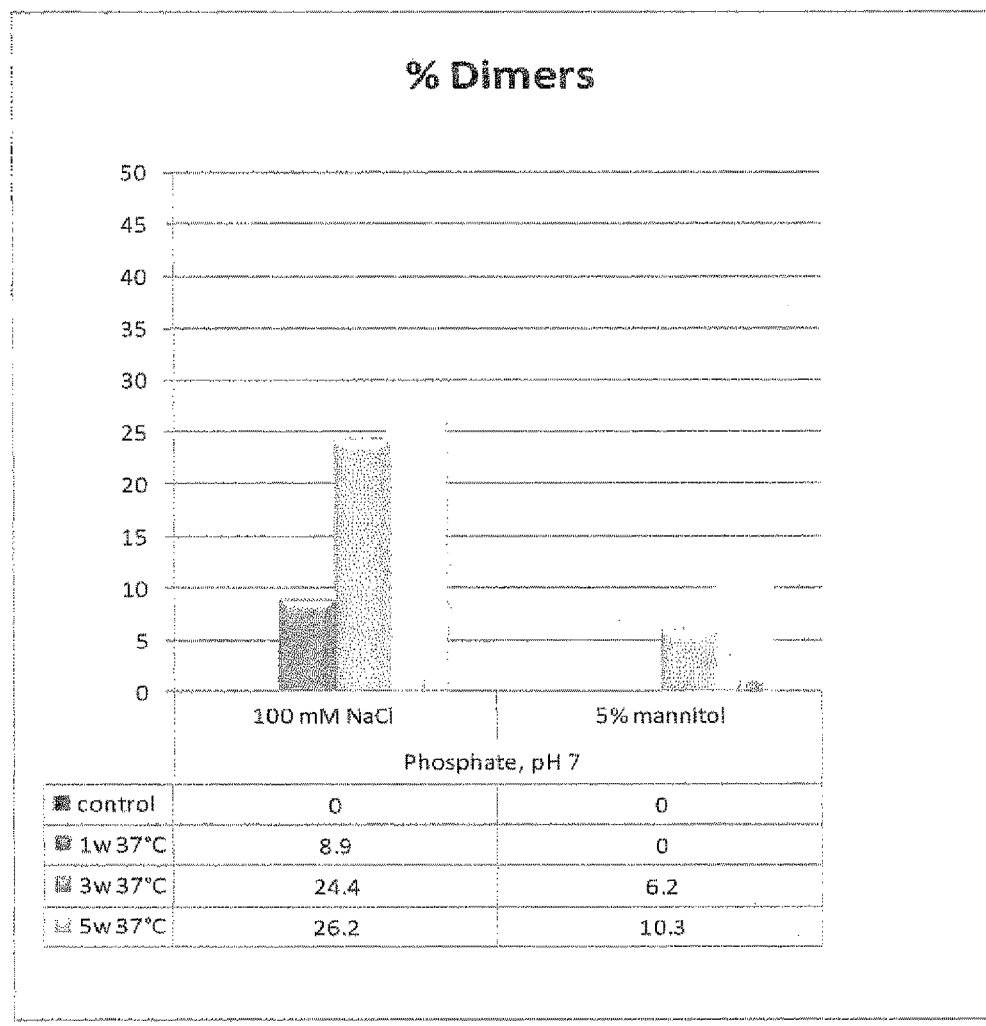

FIG. 18. SE-HPLC analysis of RANKL008a formulated in different buffers and stored for several weeks at 37° C. showed a time-dependent decrease in the surface area of the main peak (A) which is accompanied by an increase in the % prepeak (dimers, B).

Figure 19:
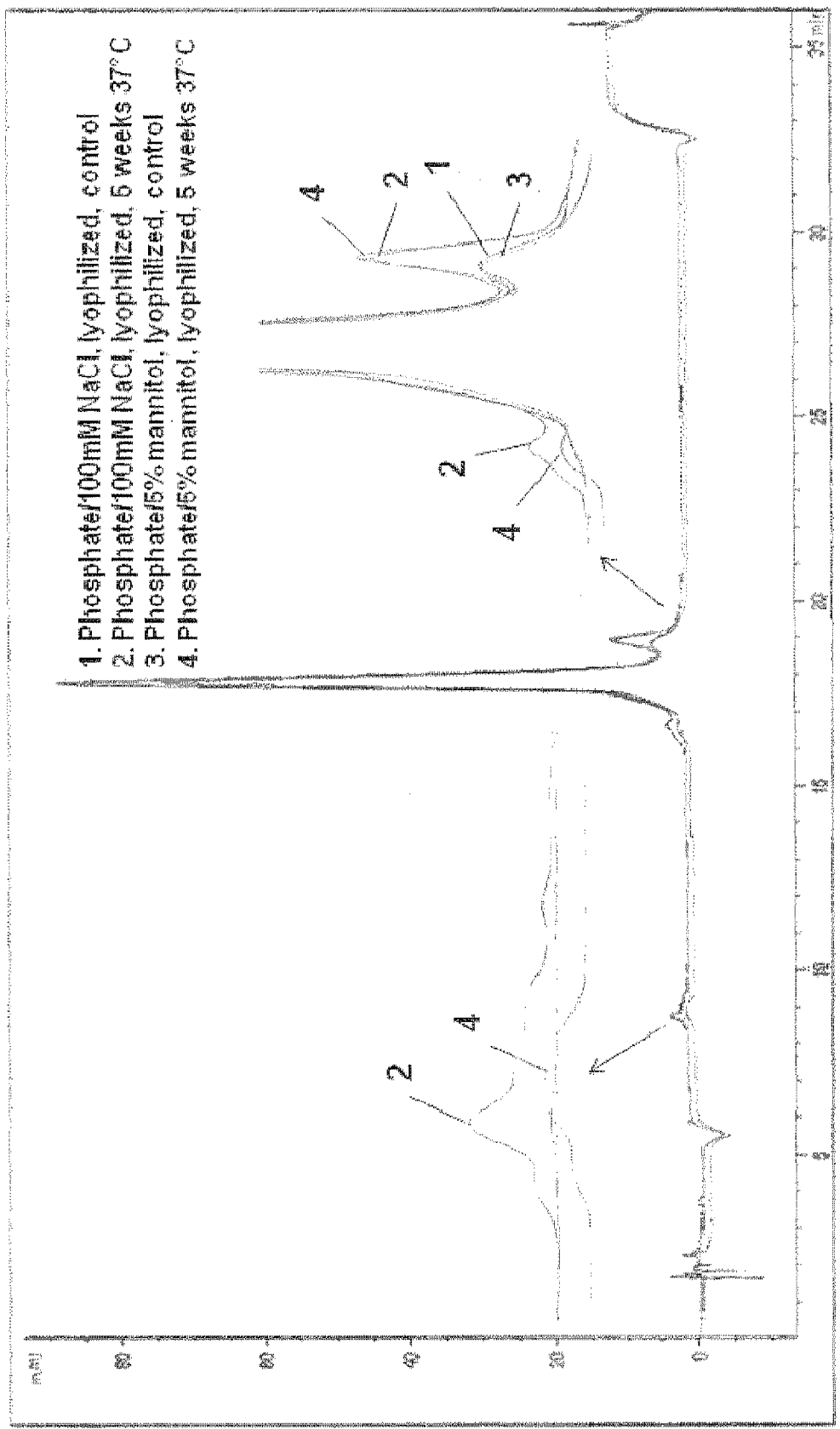

FIG. 19. The A280 nm RP-HPLC chromatograms of lyophilized RANKL008a in 10 mM Phosphate, pH 7+100 mM NaCl or 10 mM Phosphate, pH 7+5% mannitol, after incubation for 0 and 5 weeks at 37° C. A zoom on the main peak is shown as inset.

Figure 20:
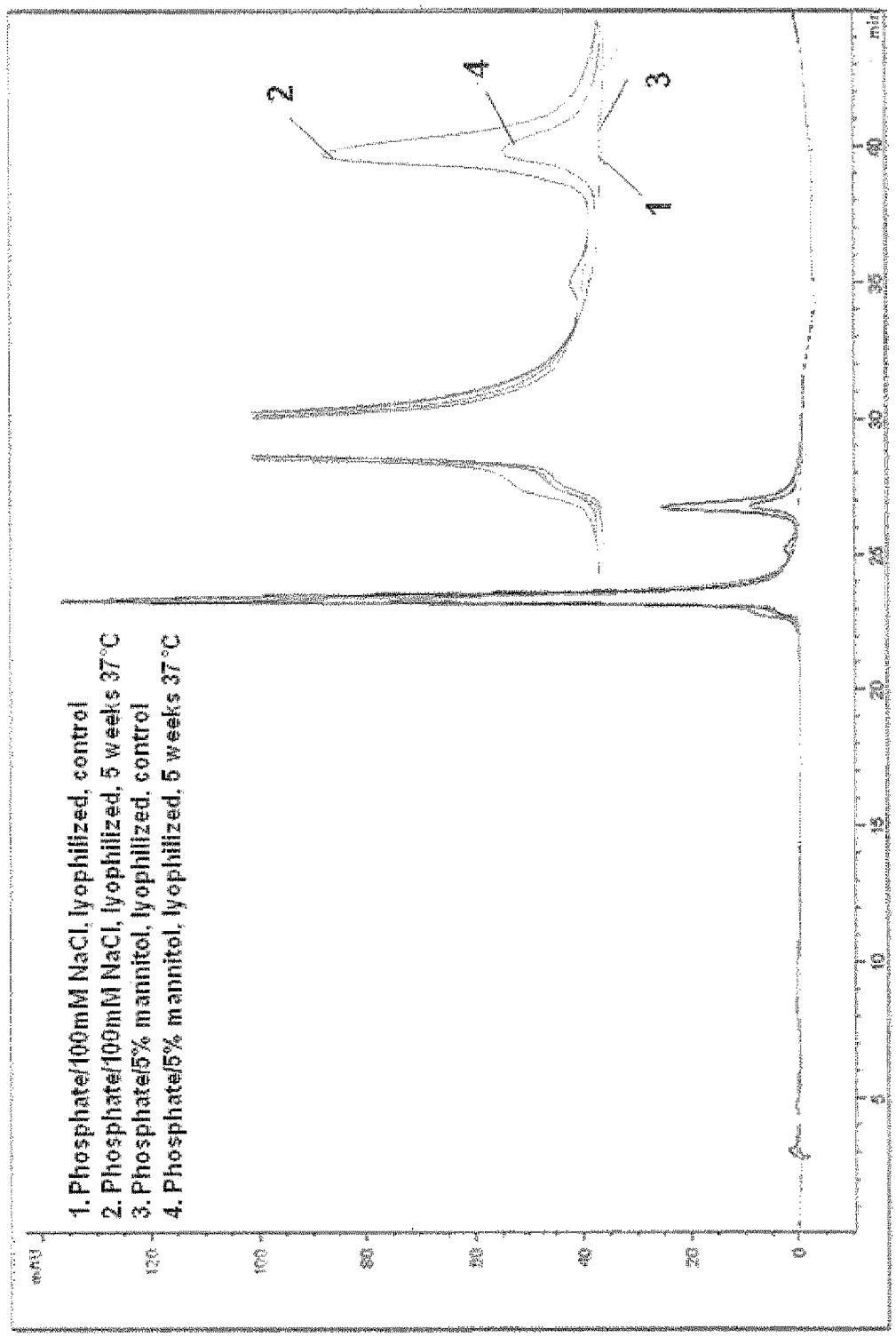

FIG. 20. The A280 nm IEX-HPLC chromatograms of lyophilized RANKL008a in 10 mM Phosphate, pH 7+100 mM NaCl or 10 mM Phosphate, pH 7+5% mannitol, after incubation for 0 and 5 weeks at 37° C. A zoom on the main peak is shown as inset.

Figure 21:
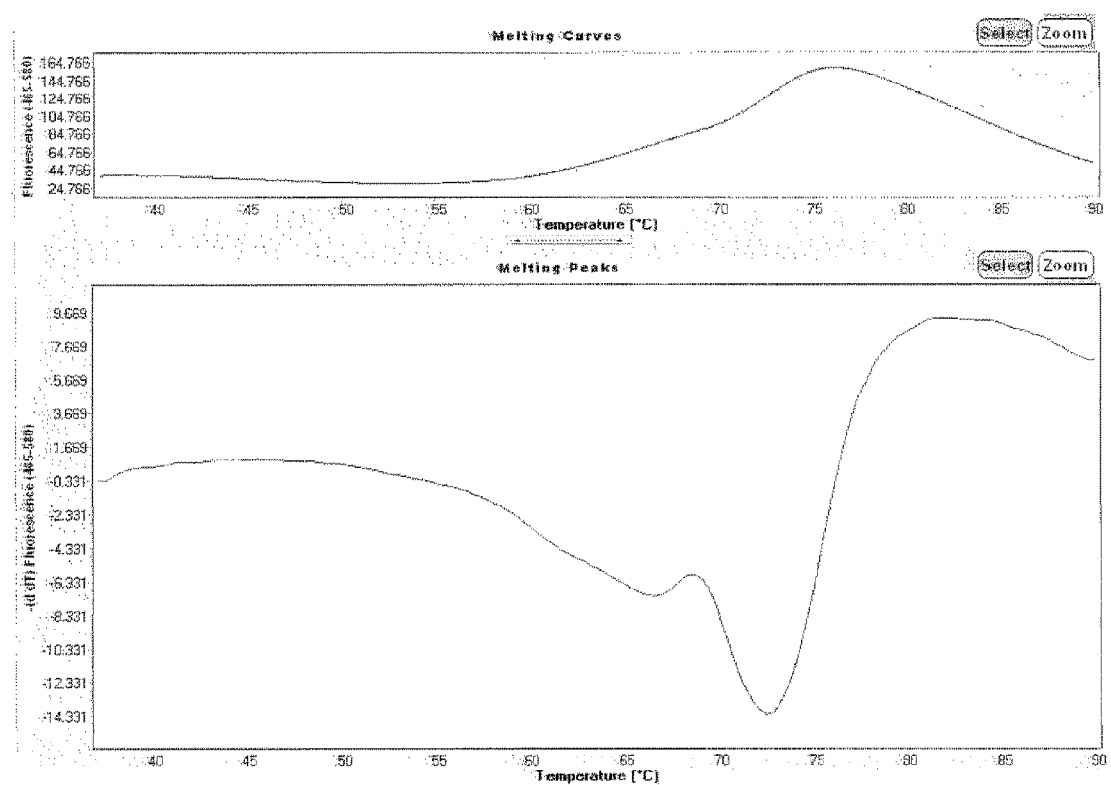

FIG. 21. Example of a fluorescence curve (up) and a negative first derivative plot (down) obtained in the thermal shift assay as described in Example 11.

Figure 22:
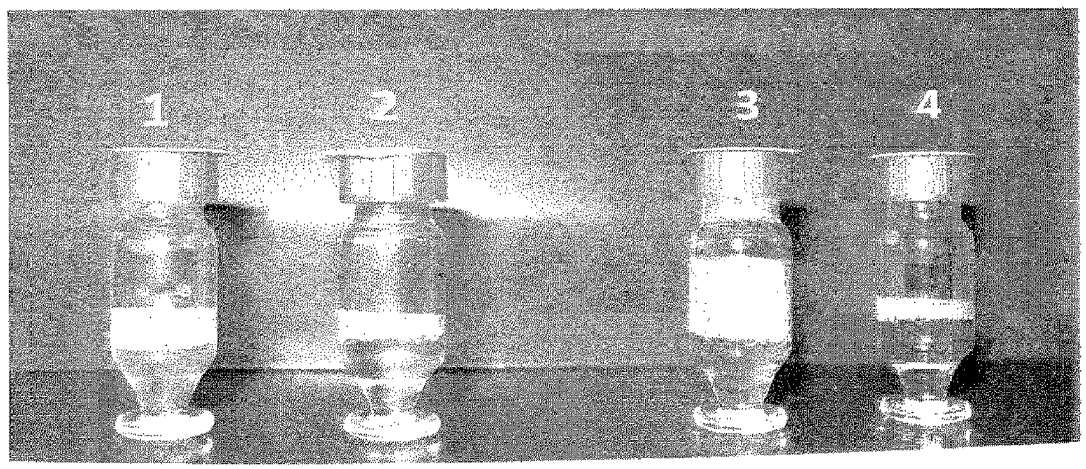

FIG. 22. Picture and visual observation of the vials after shaking. The RANKL008a sample, diluted (to 5 mg/ml) and undiluted with or without 0.01% Tween80 (v:v) was shaken strongly (10 s-1 min).

Figure 23:
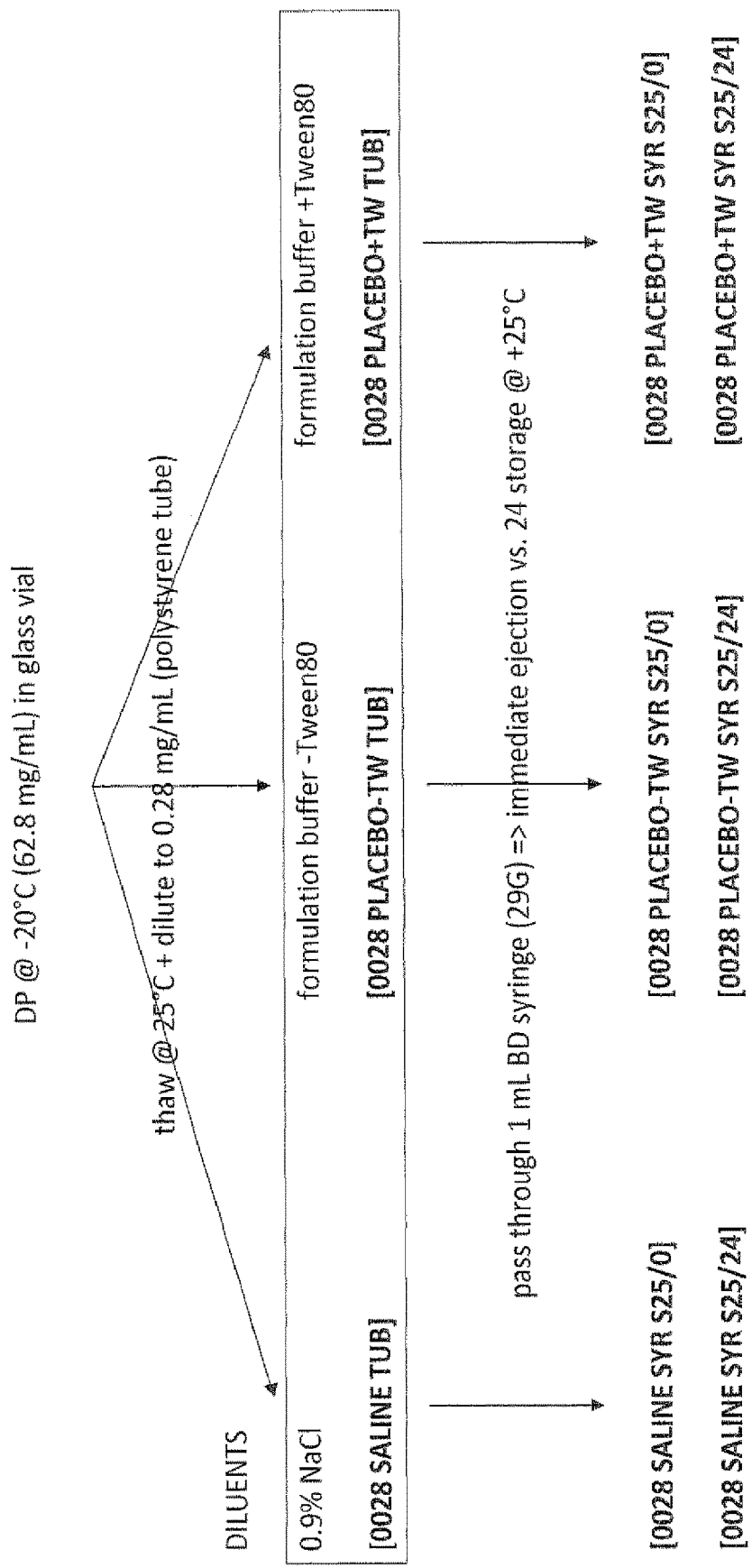

FIG. 23. Overview of dilutions and steps made in syringeability study as described in Example 13. Formulation buffer=10 mM $Na_2HPO_4$, 115 mM NaCl (pH7.0).

Figure 24:
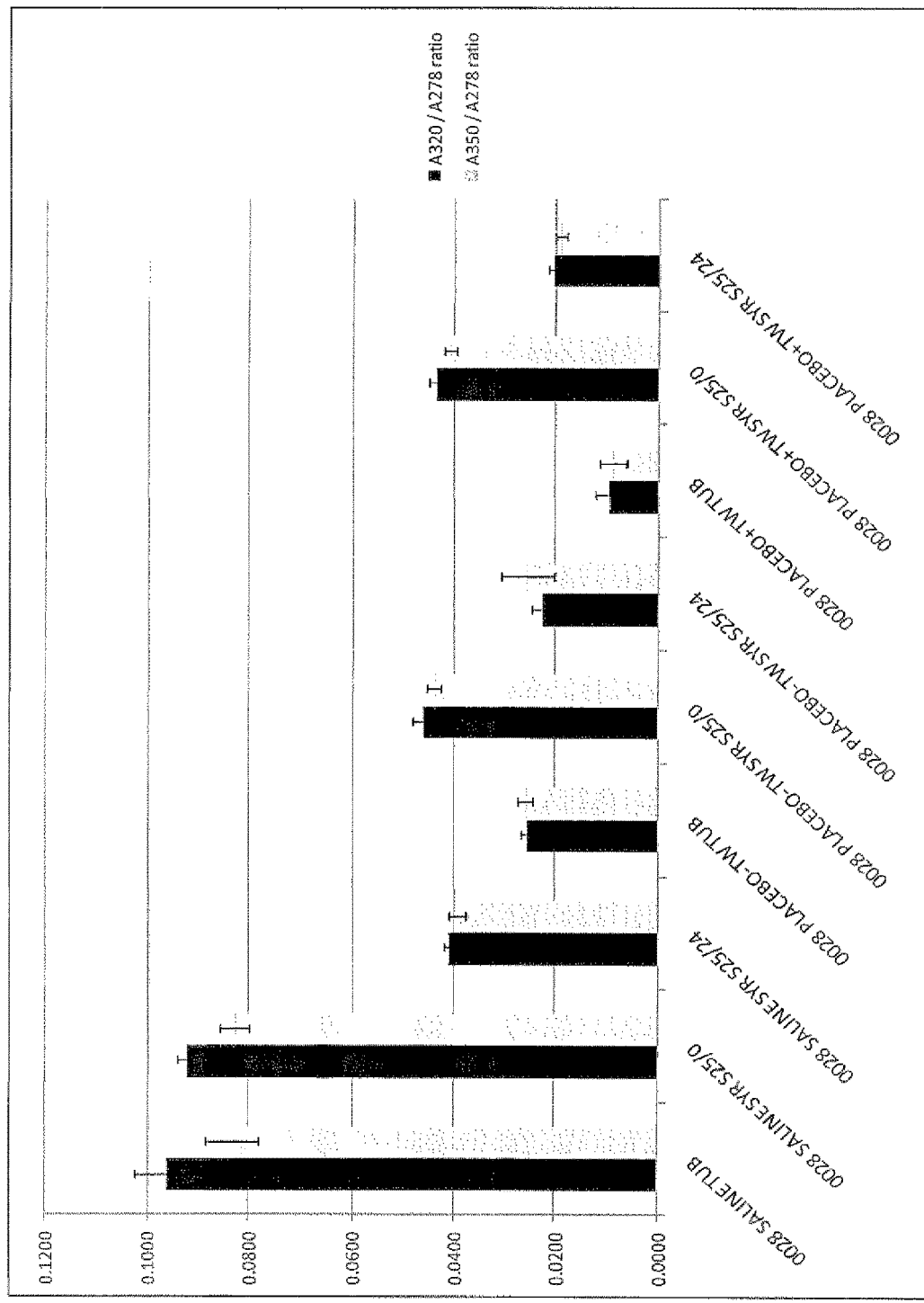

FIG. 24. 320/278 and 350/278 ratios (n=3) after passage/storage of RANKL008a in syringes with different diluents as described in Example 13.

Figure 25:
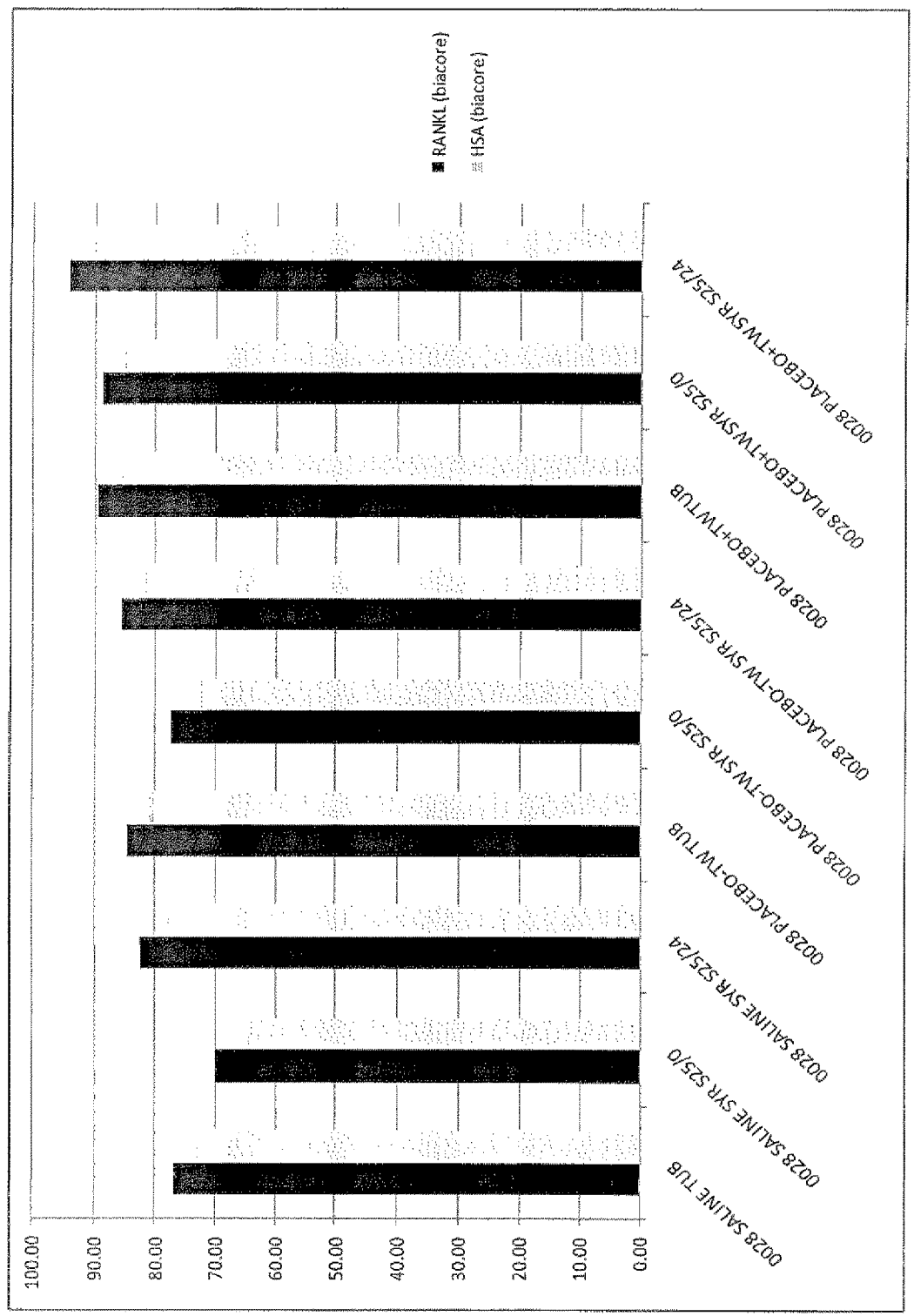

FIG. 25. Relative HSA and RANKL functionality of RANKL008a after dilution in different diluents and passage/storage in syringes as described in Example 13. Biacore: n=1; reference=P#090409nr1.

Figure 26:
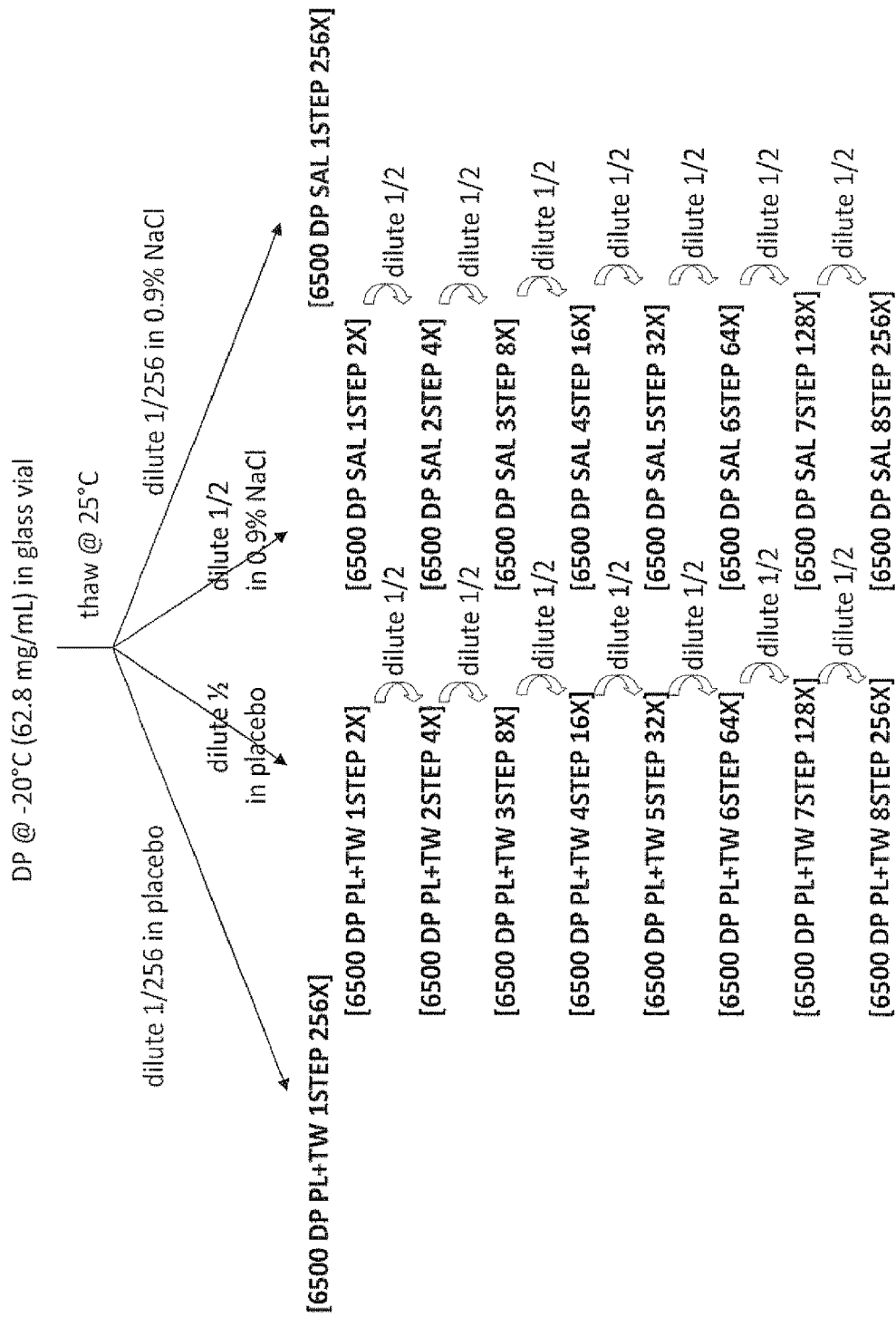

FIG. 26. Overview of diluent study comparing single step dilution (polystyrene tube) with serial dilution (Safe-Lock vial) as described in Example 14. Placebo=10 mM $Na_2HPO_4$, 115 mM NaCl, 0.01% Tween80 (v:v) (pH7.0).

Figure 27:
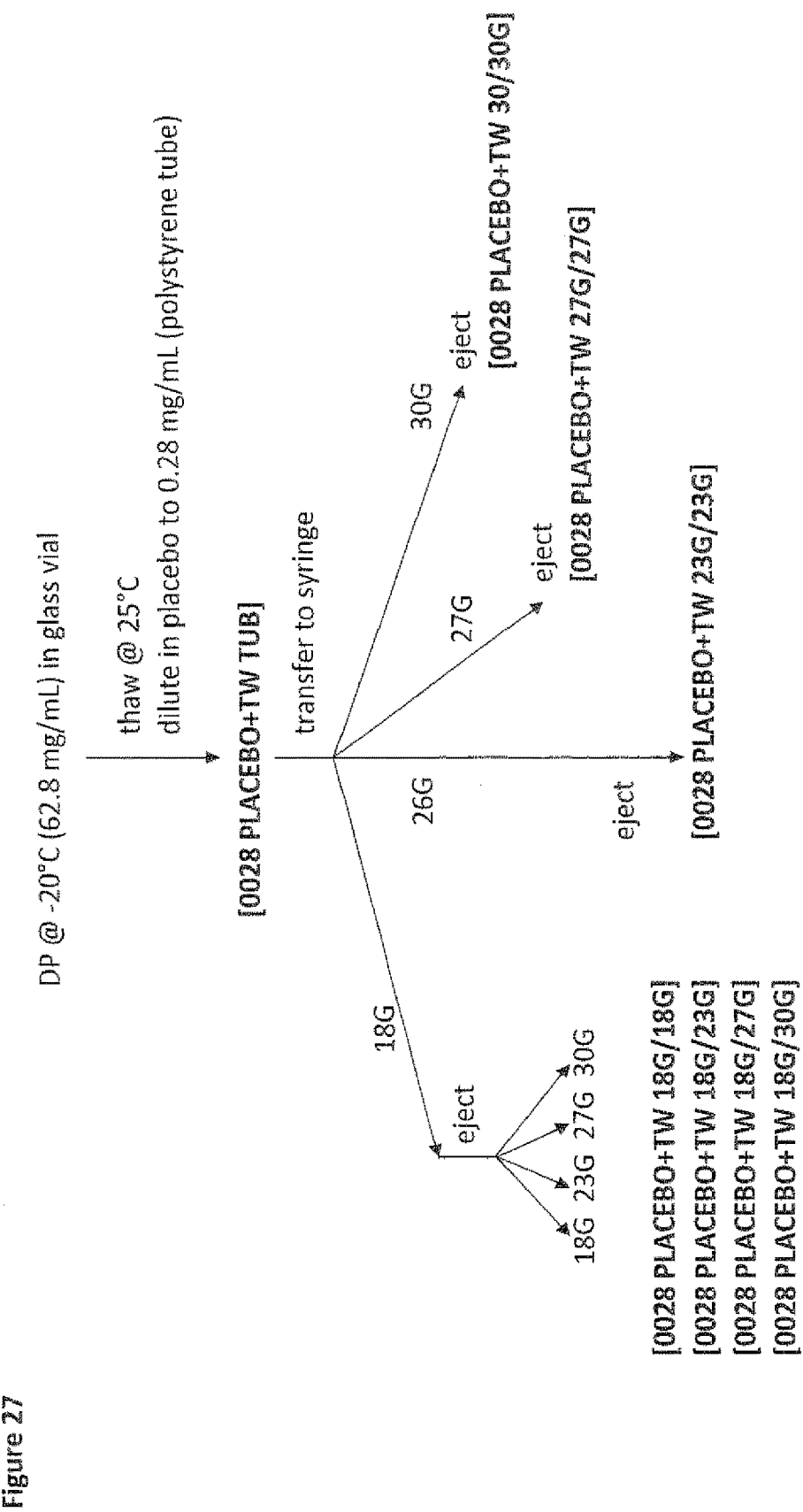

FIG. 27. Overview of needle/gauge size study with diluted RANKL008a as described in Example 15.

Figure 28:
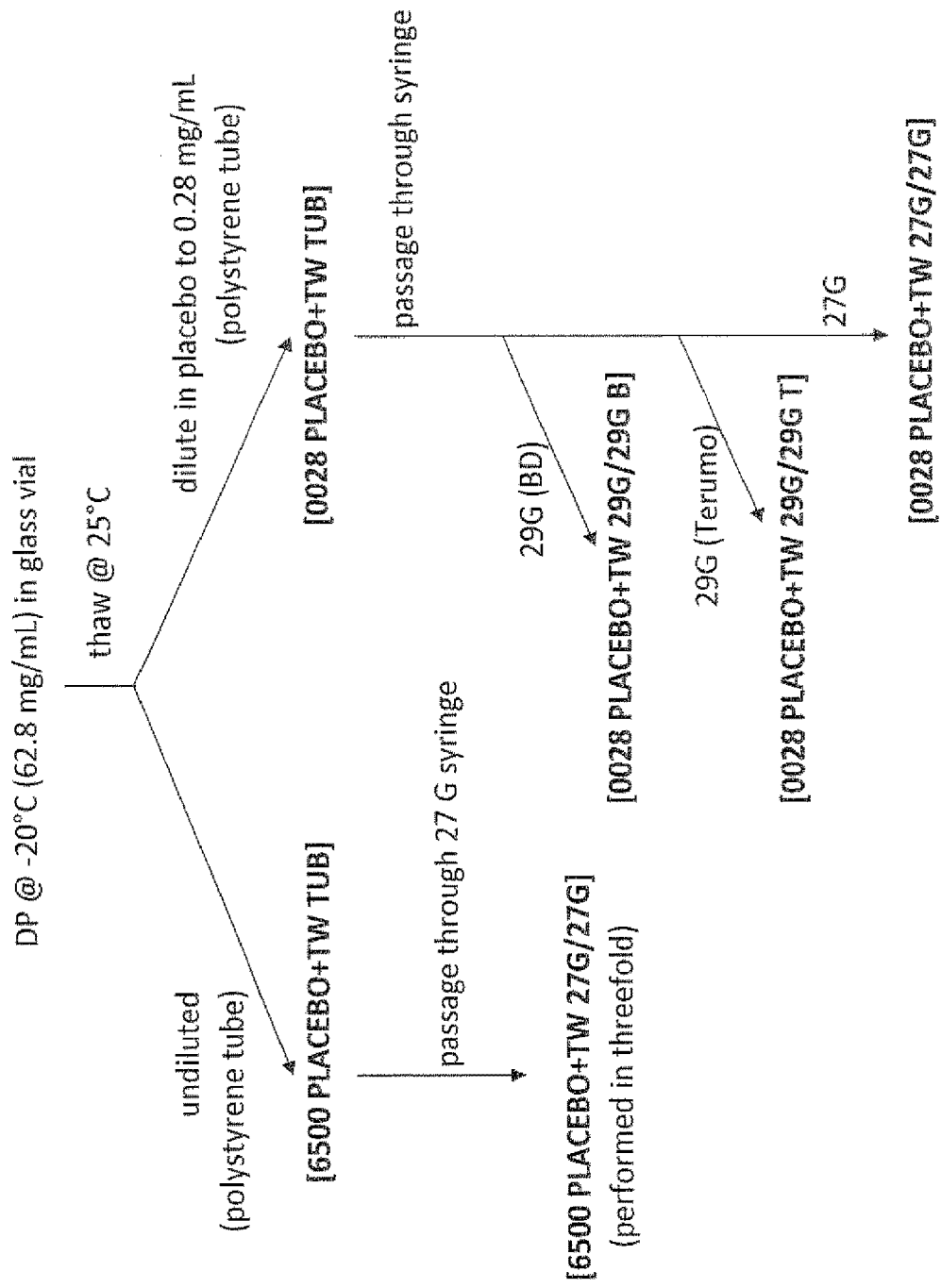

FIG. 28. Overview of further needle/gauge size study with diluted and undiluted RANKL008a as described in Example 15.

Figure 29:
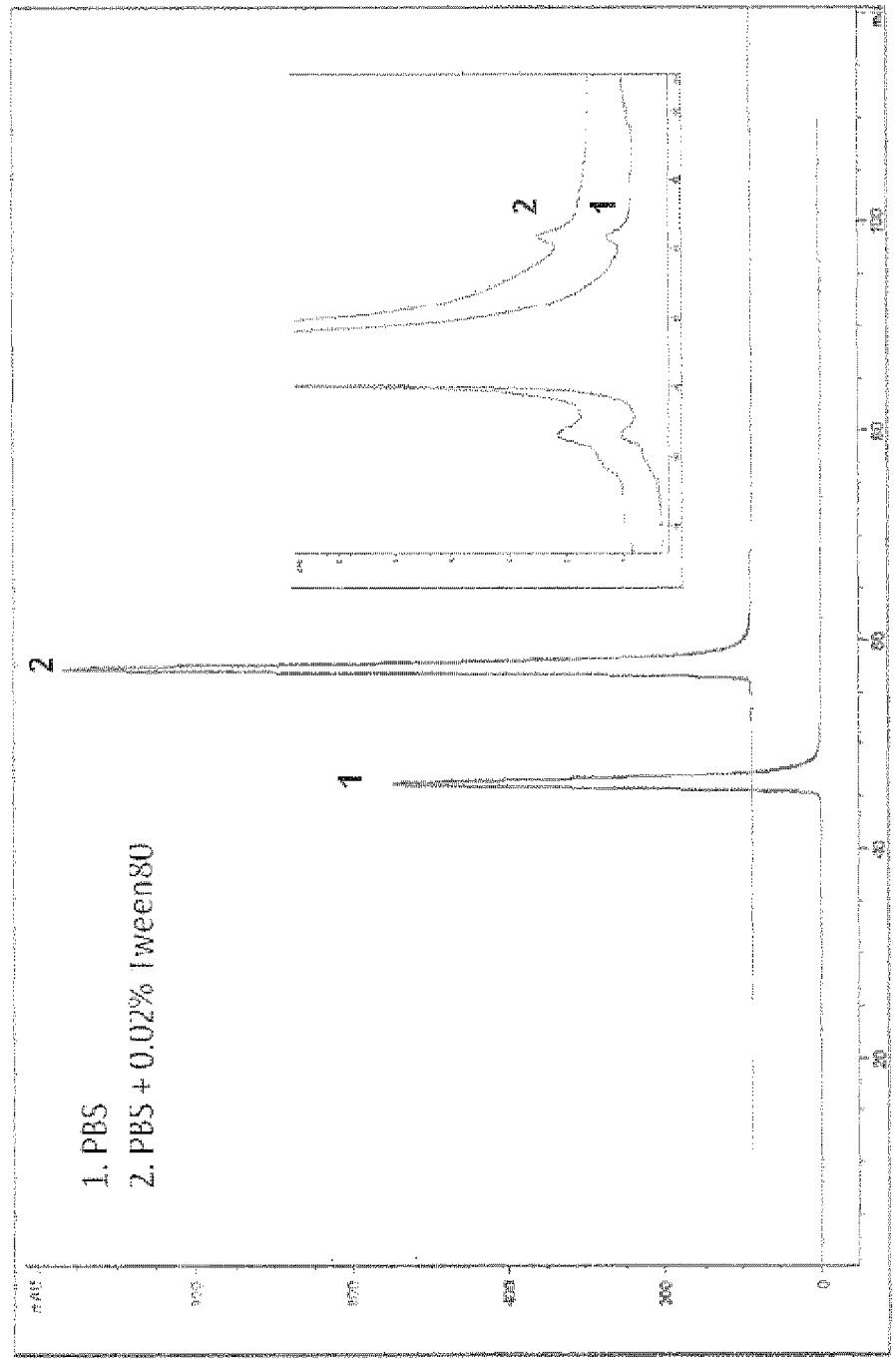

FIG. 29. The SE-HPLC chromatograms of RANKL008a at 156 mg/ml, formulated in PBS or PBS+0.02% Tween80 (v:v). Inset, zoom on the main peak.

Figure 30:
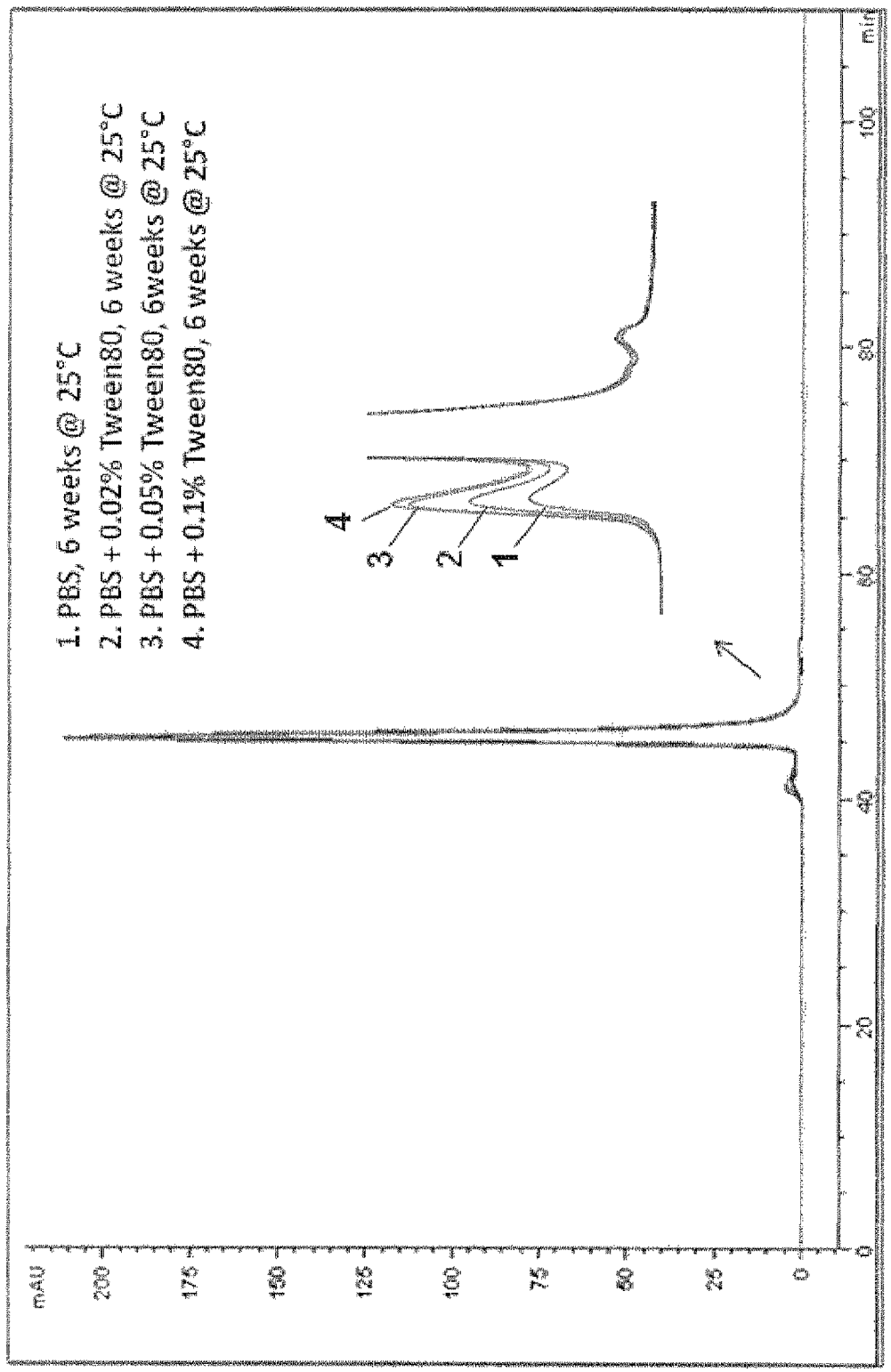

FIG. 30. Overlay of the SE-HPLC chromatograms of RANKL008a at 156 mg/ml after 6 weeks at 25° C. Insets, zoom on the main peak to demonstrate the time-dependent formation and increase of the pre- and post-peak.

Figure 31:
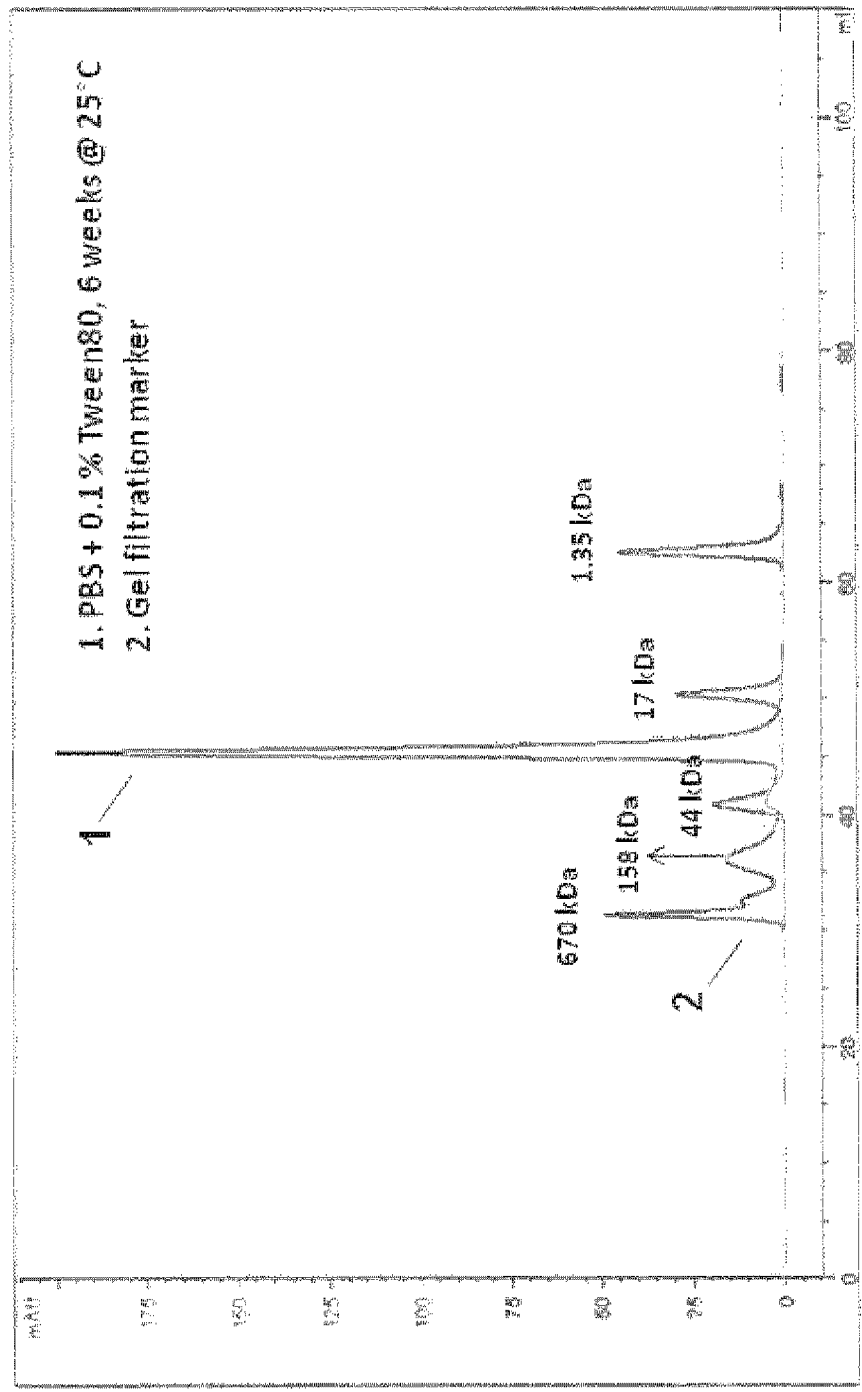

FIG. 31. Overlay of the SE-HPLC profiles of the gel filtration marker and RANKL008a (156 mg/ml) after 6 weeks at 25° C. in PBS.

Figure 32:
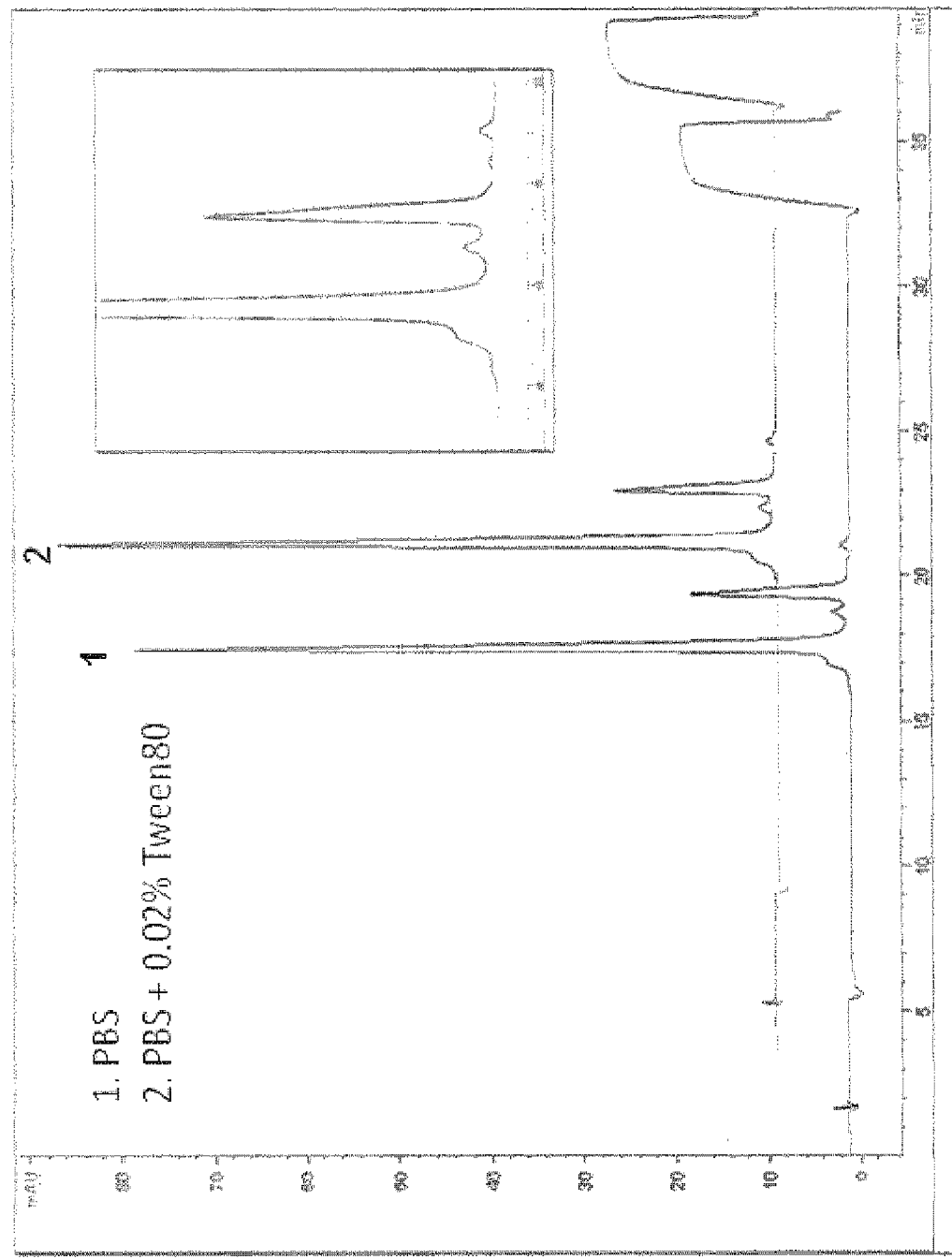

FIG. 32. The RP-HPLC chromatograms of RANKL008a at 156 mg/ml, formulated in PBS or PBS+0.02% Tween80 (v:v). Inset, zoom on the main peak.

Figure 33:
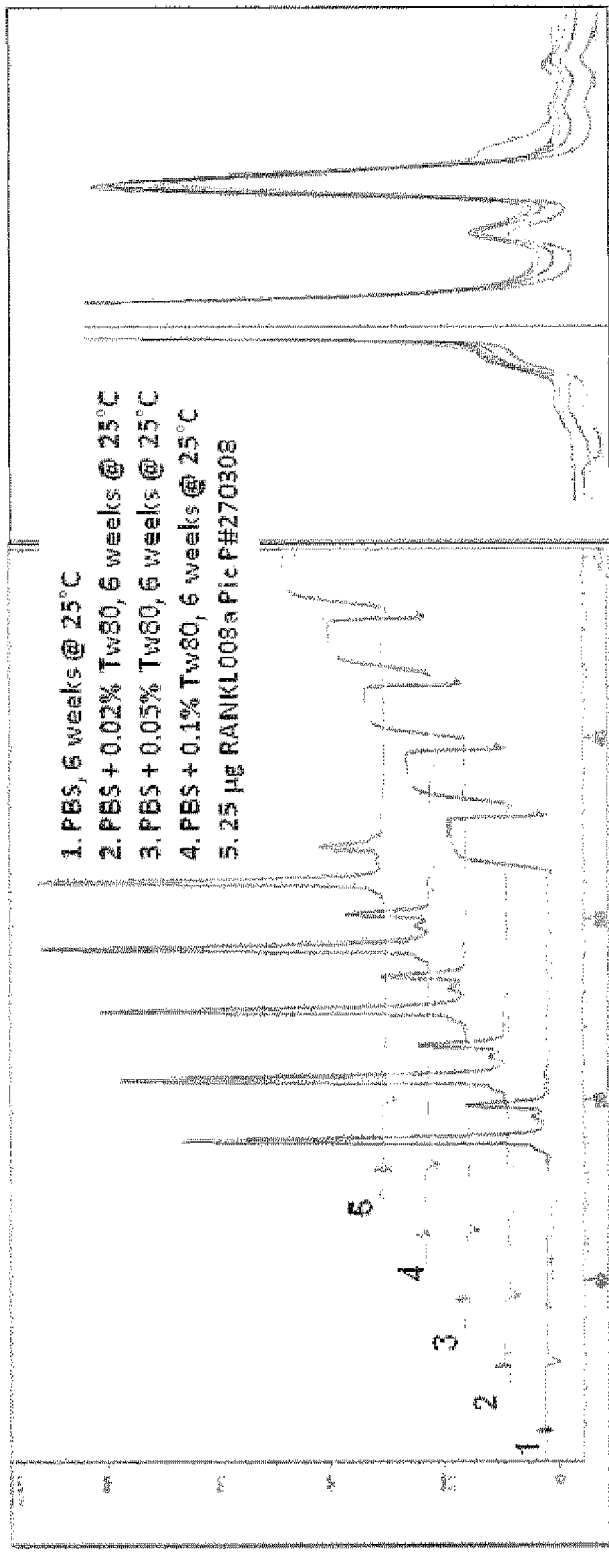

FIG. 33. Left panel: the RP-HPLC chromatograms of RANKL008a 156 mg/ml after storage for 6 weeks at 25° C. Right panel: zoom on the main peak and pre/post-peaks.

Figure 34:
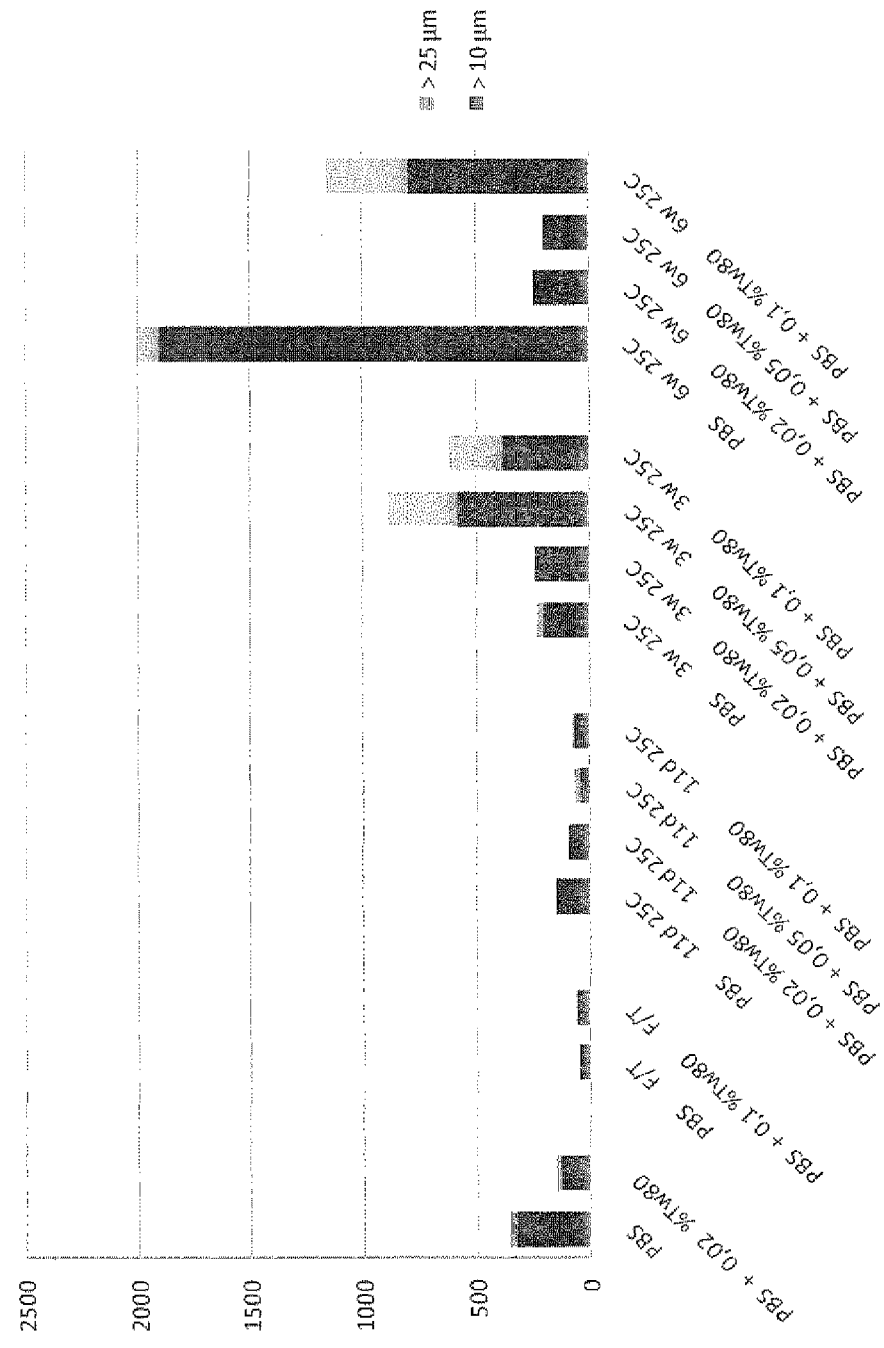

FIG. 34. The number of sub-visible particles in stressed and unstressed samples of RANKL008a at 156 mg/ml as measured by PAMAS.

Figure 35:
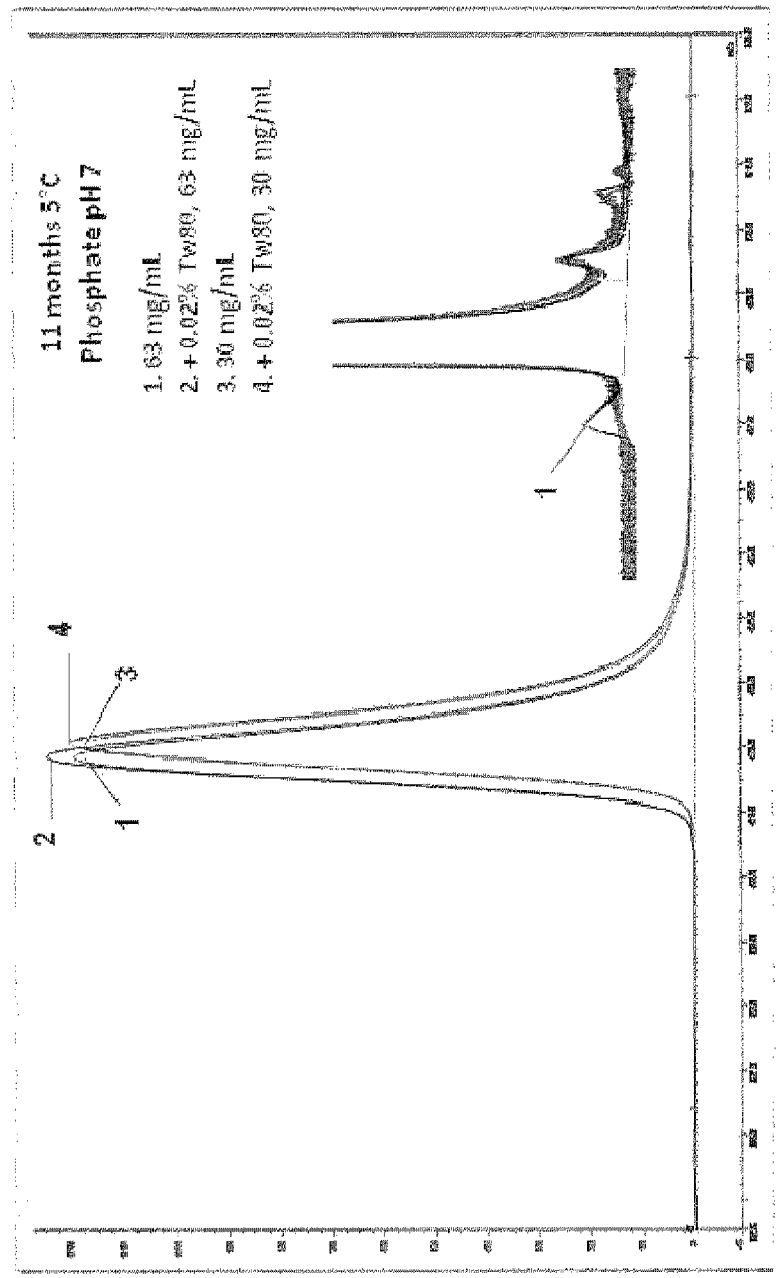

FIG. 35. Overlay of SE-HPLC chromatograms of phosphate (±0.02% Tween80 (v:v)) samples after storage during 11 months at 5° C. ($\lambda$=280 nm).

Figure 36:
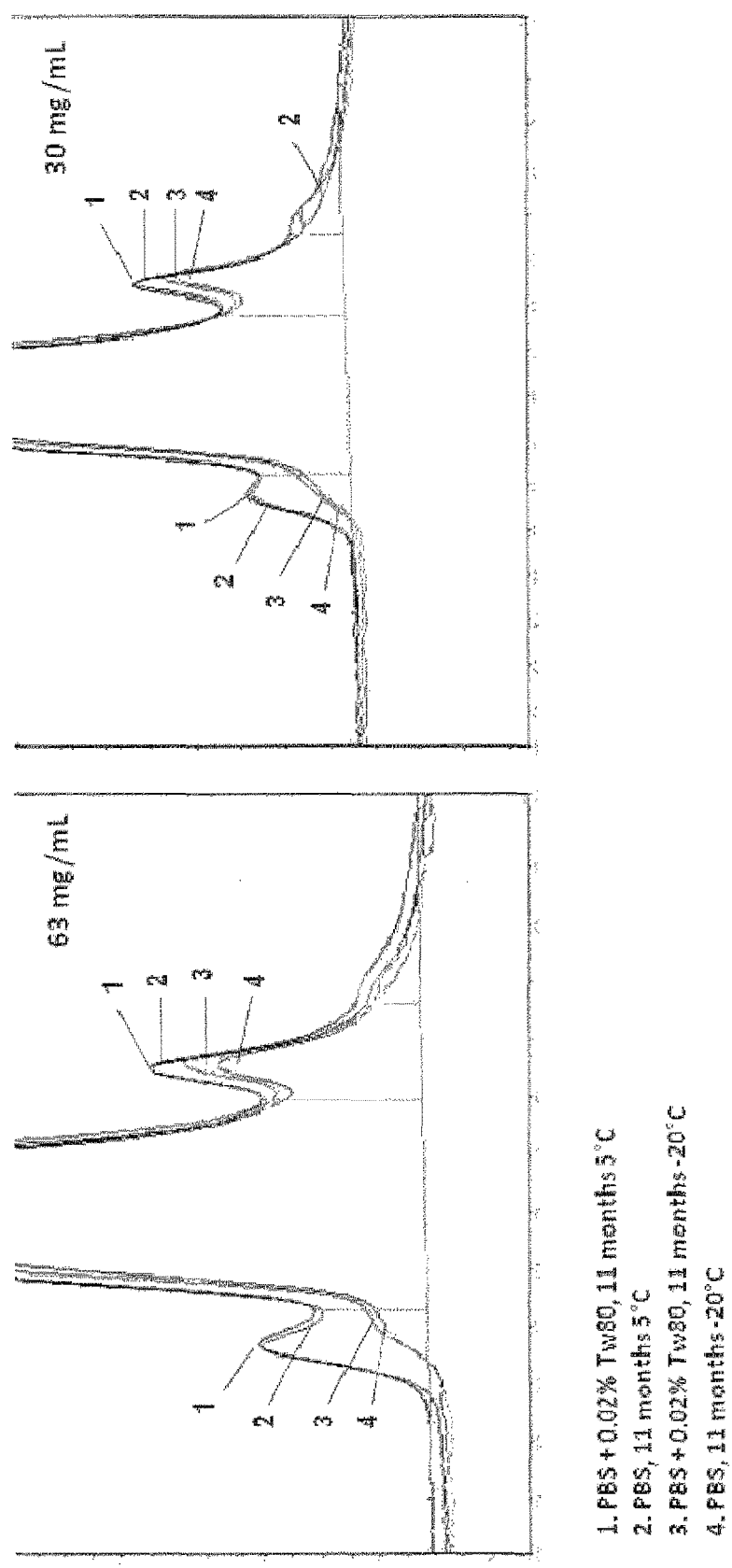
Figure 36:
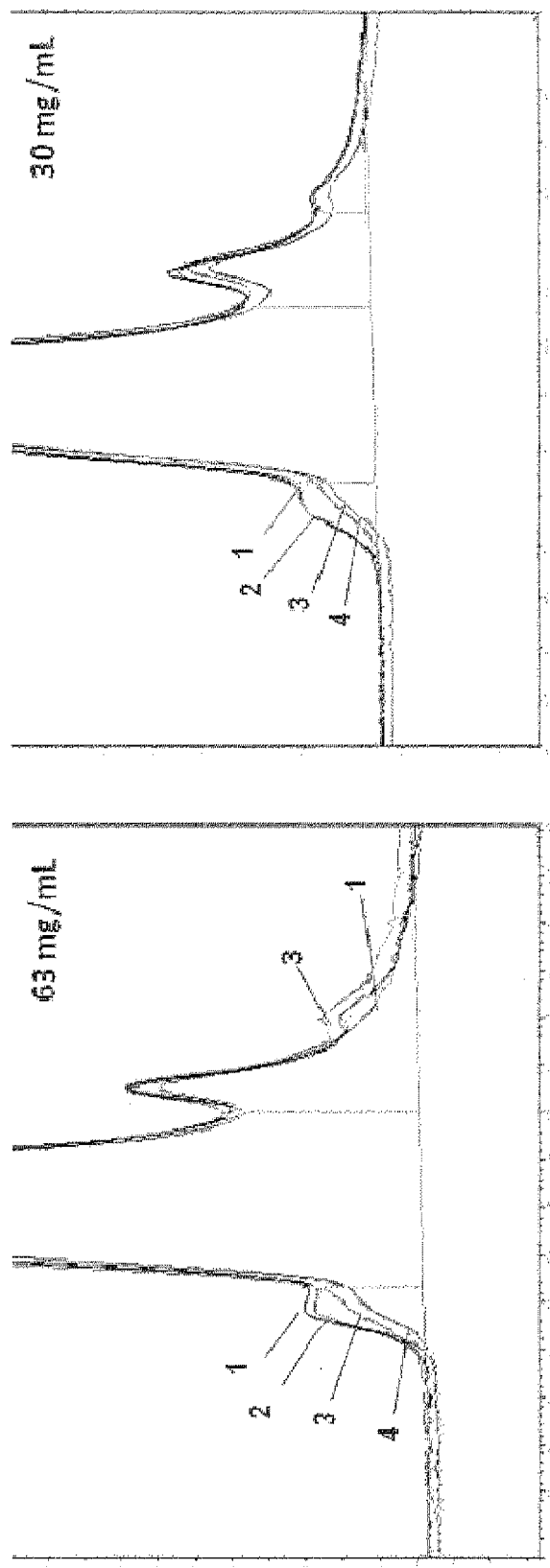
Figure 36:
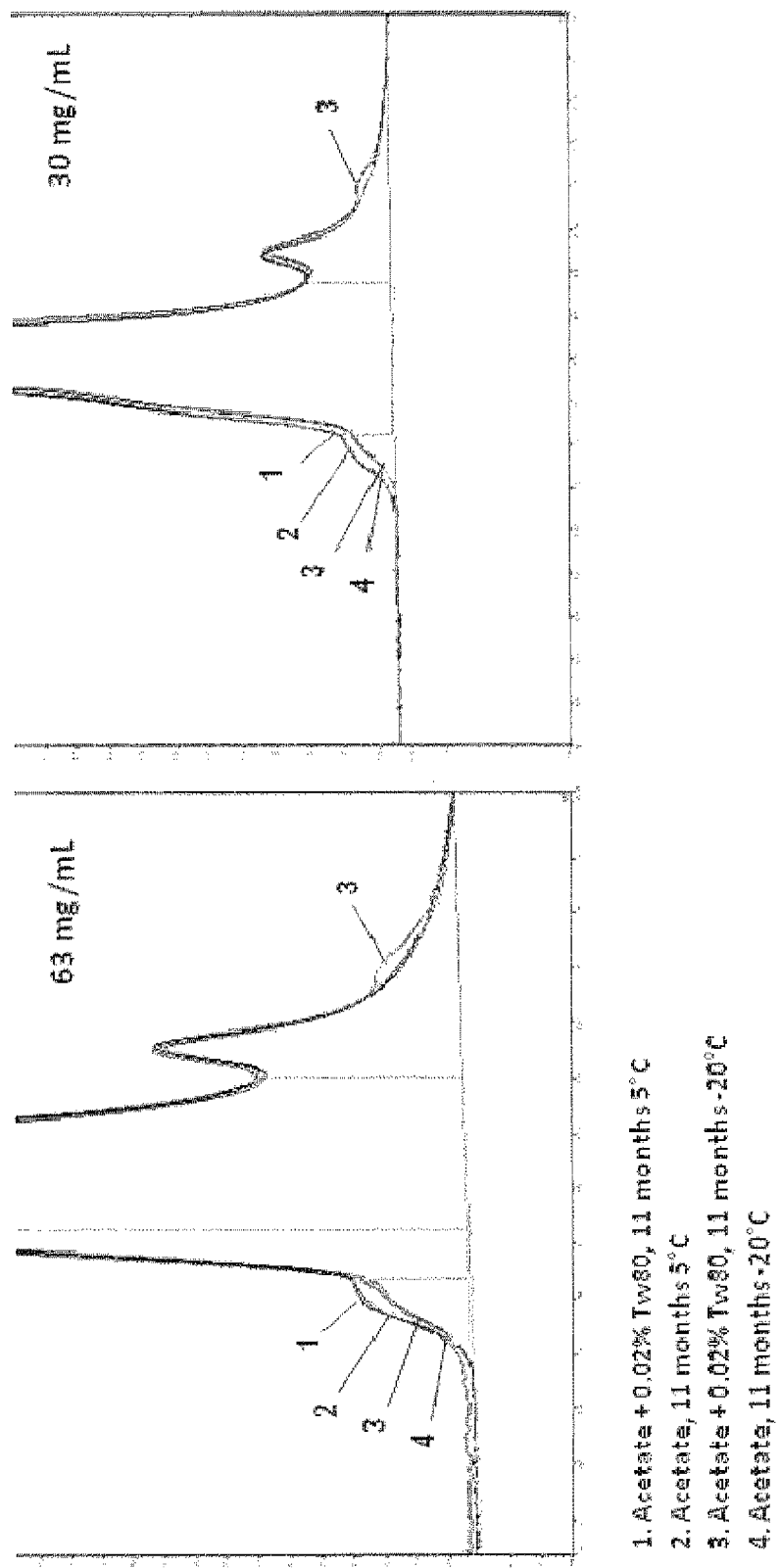

FIG. 36. Overlay of RP-HPLC chromatograms of samples in different buffers: comparison between 11 months at 5° C. and −20° C. at 63 mg/ml (left side) and 30 mg/ml (right side). PBS (A), phosphate (B) and acetate (C).

Figure 37:
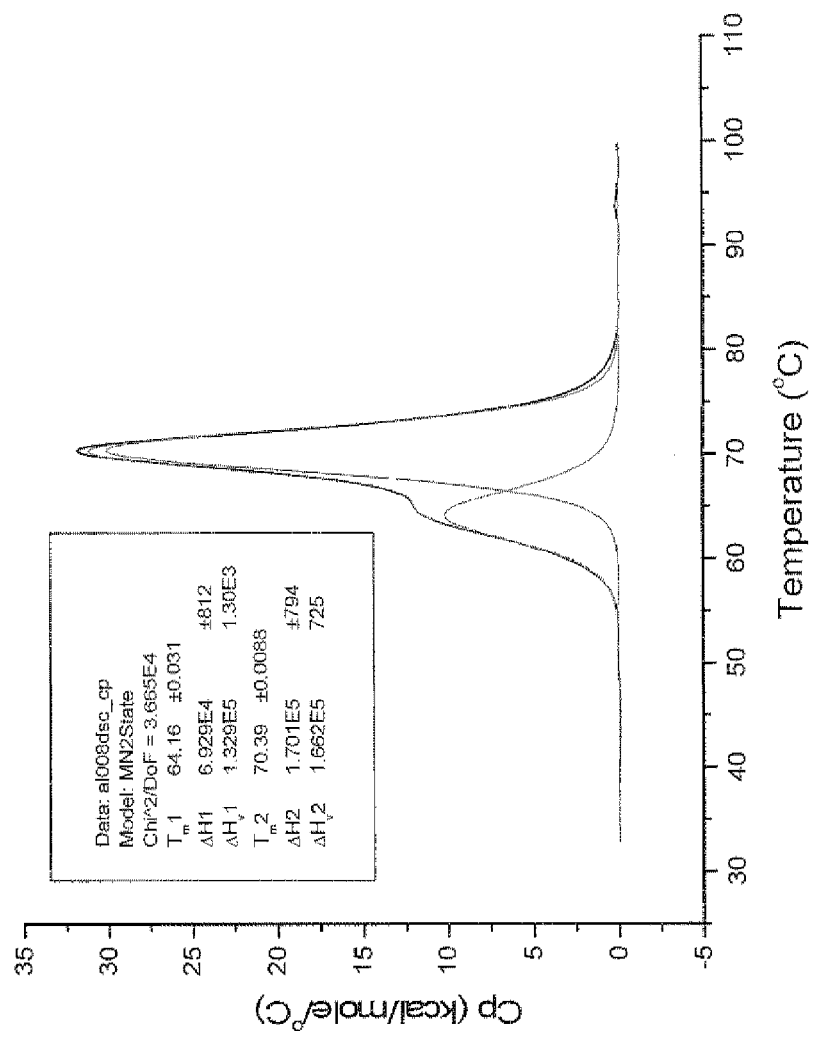

FIG. 37. Differential scanning calorimetry unfolding curve of RANKL008a. Non-two state model was applied to the DSC scan corresponding to RANKL008a.

Figure 38:
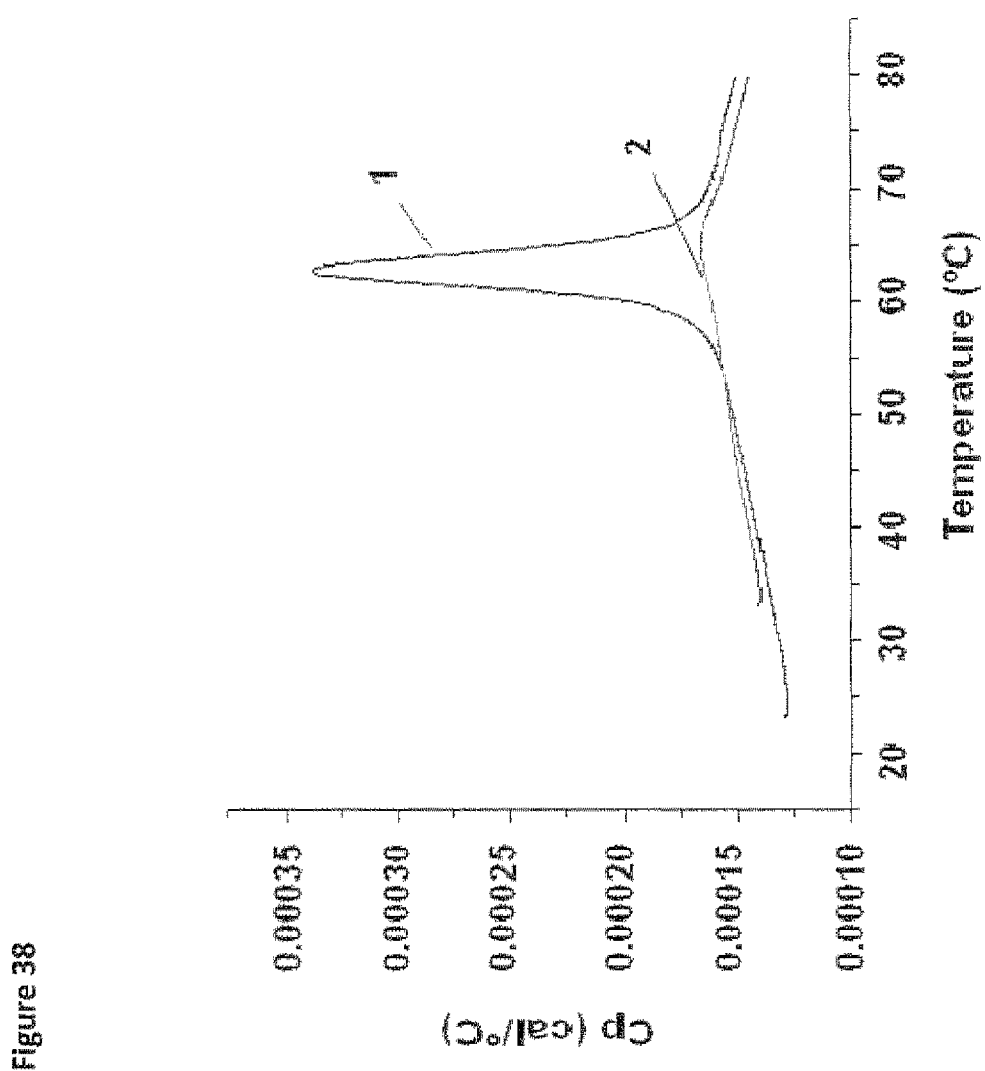

FIG. 38. Differential scanning calorimetry unfolding curve of Alb8. The sample was scanned up to 80° C. (1) and a rescan of the same sample was performed (2). A $T_m$ of 62.8° C. was noticed.

DETAILED DESCRIPTION

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

As used herein, the term "isolated" in the context of a polypeptide refers to a polypeptide which is substantially free of cellular material or contaminating proteins from the cell or tissue source from which it is derived, or substantially free of chemical precursors or other chemicals when chemically synthesized. The language "substantially free of cellular material" includes preparations of a polypeptide in which the polypeptide is separated from cellular components of the cells from which it is isolated or recombinantly produced. Thus, a polypeptide that is substantially free of cellular material includes preparations of a polypeptide having less than about 30%, 20%, 10%, or 5% (by dry weight) of heterologous protein, polypeptide, peptide, or antibody (also referred to as a "contaminating protein"). When the polypeptide is recombinantly produced, it may also be substantially free of culture medium, i.e., culture medium represents less than about 20%, 10%, or 5% of the volume of the polypeptide preparation. When the polypeptide is produced by chemical synthesis, it is preferably substantially free of chemical precursors or other chemicals, i.e., it is separated from chemical precursors or other chemicals which are involved in the synthesis of the polypeptide. Accordingly, such preparations of a polypeptide have less than about 30%, 20%, 10%, 5% (by dry weight) of chemical precursors or compounds other than the polypeptide of interest. In a specific embodiment, an "isolated" polypeptide is purified by a multi-step purification process that comprises two chromatography steps (e.g. cation exchange and anion exchange), a 100K ultrafiltration step, followed by a buffer exchange and concentration step in Ultrafiltration/Diafiltration mode.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, such as a cynomolgus monkey, chimpanzee, baboon and a human), and more preferably a human. In a certain embodiment, the subject is a mammal, preferably a human, with a disease or disorder associated with excessive bone loss and/or characterized by aberrant expression and/or activity of RANKL, such as e.g. osteoporosis, cancer-related bone diseases, and/or bone loss associated with autoimmunity and/or viral infection. In another embodiment, the subject is a mammal, preferably a human, at risk of developing a disease or disorder associated with or characterized by excessive bone loss and/or aberrant expression and/or activity of RANKL, such as e.g. osteoporosis, cancer-related bone diseases, and/or bone loss associated with autoimmunity and/or viral infection.

The terms "stability" and "stable" as used herein in the context of a formulation comprising a polypeptide comprising one or more single variable domains refer to the resistance of the polypeptide in the formulation to aggregation, the formation of degradation products and/or the formation of fragmentation products under given transportation and/or storage conditions. Apart from this and/or in addition, the "stable" formulations of the invention retain biological activity under given transportation and/or storage conditions. The stability of said polypeptide can be assessed by degrees of aggregation, degradation and/or fragmentation (as measured e.g. by SE-HPLC, RP-HPLC, IEX-HPLC, subvisible particle counting, analytical ultracentrifugation, dynamic light scattering, etc.), and/or by % of biological activity (as measured e.g. by ELISA, Biacore, etc.) compared to a reference formulation. For example, a reference formulation may be a reference standard frozen at −20° C. or <−65° C. (such as e.g. −80° C.) consisting of the same polypeptide at the same concentration in D-PBS or consisting of the same polypeptide at the same concentration and in the same buffer as the stressed samples but without applying the stress conditions, which reference formulation regularly gives a single peak by SE-HPLC, RP-HPLC and/or IEX-HPLC and/or keeps its biological activity in Biacore and/or ELISA.

"Solubility" is often described as the maximum achievable protein concentration whereby all of the protein remains in solution. At this concentration the protein should still be monomeric and free of aggregates. For determining protein solubility only a limited number of (mostly empirical) techniques are currently available. A first and popular technique consists of concentrating the sample by using centrifugal ultrafiltration up to the point where an opalescent solution is formed. Subsequently, the insoluble fraction is removed and the protein content of the supernatant is measured. Centrifugal concentrating devices such as for example Vivaspin concentrators with a molecular weight cut-off of 5 kDa can be used but require reasonable amounts of protein. Solubility can also be monitored using an inert macromolecule such as polyethylene glycol (PEG; Mr>6,000), which precipitates proteins primarily through an excluded volume effect, a process that can be generally understood in terms of a simple colloidal phase separation. A logarithmic linear relationship between protein solubility and weight percent polyethylene glycol can be obtained, and from this plot the intercept yields the solubility value.

The phrase "low to undetectable levels of aggregation" as used herein refers to samples containing no more than 5%, no more than 4%, no more than 3%, no more than 2%, no more than 1% or no more than 0.5% aggregation by weight of protein as measured by high performance size exclusion chromatography (SE-HPLC), subvisibie particle counting, analytical ultracentrifugation (AUC), dynamic light scattering (DLS), static light scattering (SLS), elastic light scattering, OD320/OD280 measurement, Fourier Transform infrared Spectroscopy (FTIR), circular dichroism (CD), urea-induced protein unfolding techniques, intrinsic tryptophan fluorescence and/or differential scanning calorimetry techniques. Aggregation as used in the present invention means the development of high molecular weight aggregates, i.e. aggregates with an apparent molecular weight of more/higher than the apparent 44 kDa observed in SE-HPLC analysis for dimers in comparison with molecular weight markers. Aggregation can be assessed by various methods known in the art. Without being limiting, examples include SE-HPLC, analytical ultracentrifugation, dynamic light scattering, subvisibie particle counting, and/or the methods mentioned above.

The term "low to undetectable levels of fragmentation and/or degradation" as used herein refers to samples containing equal to or more than 80%, 85%, 90%, 95%, 98% or 99% of the total protein, for example, in a single peak as determined by SE-HPLC, RP-HPLC and/or IEX-HPLC, representing the non-degraded polypeptide, and containing no other single peaks having more than 5%, more than 4%, more than 3%, more than 2%, more than 1%, or more than 0.5% of the total protein in each.

The term "very little to no loss of the biological activities" as used herein refers to single variable domain activities, including but not limited to, specific binding abilities of the single variable domain to an antigen of interest (preferably RANKL and/or HSA) as measured by various immunological assays, including, but not limited to ELISAs and/or by Surface Plasmon Resonance (Biacore). In one embodiment, the single variable domains of the formulations of the invention retain at least 50%, preferably at least 55%, 60%, 65%, 70%, 75%, 80%, 85%, 90%, 95% or 98% of the ability to specifically bind to an antigen as compared to a reference formulation as measured by an immunological assay known to one of skill in the art or described herein. For example, an ELISA based assay (e.g. as described in the Example section) may be used to compare the ability of the single variable domain to specifically bind to its target. A "reference formulation" as used herein refers to a formulation that is frozen at a temperature of −20±5° C. or at a temperature below −64° C. (such as e.g. at −80° C.) consisting of the same single variable domain at the same concentration in D-PBS or consisting of the same single variable domains at the same concentration in the same buffer/excipients as the stressed samples but without applying the stress conditions, which reference formulation regularly gives a single peak by SE-HPLC, RP-HPLC and/or IEX-HPLC and/or keeps its biological activity in Biacore and/or ELISA.

The phrase "pharmaceutically acceptable" as used herein means approved by a regulatory agency of the Federal or a state government, or listed in the U.S. Pharmacopeia, European Pharmacopoeia or other generally recognized pharmacopeia for use in animals, and more particularly in humans. In this sense, it should be compatible with the other ingredients of the formulation and not eliciting an unacceptable deleterious effect in the subject.

According to the European Pharmacopoeia, a solution is considered isotonic if it has an osmolality of 290±30 mOsm/kg. Osmolality measurements were therefore performed on the different formulations used in the stability studies.

As used herein, the term "effective amount" refers to the amount of an agent (e.g. a prophylactic or therapeutic agent) which is sufficient to reduce and/or ameliorate the severity and/or duration of a disease or disorder, for example, a disease or disorder associated with excessive bone loss and/or a disease or disorder associated by aberrant expression and/or activity of RANKL, e.g. osteoporosis, cancer-related bone diseases, and/or bone loss associated with autoimmunity and/or viral infection.

As used herein, the terms "therapeutic agent" and "therapeutic agents" refer to any agent(s) which can be used in the prevention, treatment and/or management of a disease or disorder, for example, a disease or disorder associated with or characterized by aberrant expression and/or activity of a certain target such as e.g. RANKL. In the context of the present invention, the term "therapeutic agent" refers to a polypeptide comprising one or more single variable domains (of which SEQ ID NO: 1 is a preferred example). In certain other embodiments, the term "therapeutic agent" refers an agent other than the polypeptide of the invention which might be used in the formulation.

As used herein, the term "therapeutically effective amount" refers to the amount of a therapeutic agent (e.g. a polypeptide comprising one or more single variable domains such as e.g. SEQ ID NO: 1), that is sufficient to reduce the severity of a disease or disorder, for example, a disease or disorder associated with or characterized by aberrant expression and/or activity of a certain target such as e.g. RANKL.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and decreased viscosity. Examples of excipients include, but are not limited to, proteins (e.g., serum albumin), amino acids (e.g., aspartic acid, glutamic acid, lysine, arginine, glycine), surfactants (e.g., SDS, Tween20, Tween80, polysorbate and nonionic surfactants), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., Mack Publishing Co., Easton, Pa.), which is incorporated herein in its entirety.

The term "variable domain" or "immunoglobulin variable domain" refers to the part or domain of an immunoglobulin molecule or antibody which is partially or fully responsible for antigen binding. The term "single variable domain" or "immunoglobulin single variable domain" (both terms are used interchangeably), defines molecules wherein the antigen binding site is present on, and formed by, a single immunoglobulin domain. This sets single variable domains apart from "conventional" immunoglobulins or their fragments, wherein two immunoglobulin domains, in particular two "variable domains" interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of a single variable domain is formed by a single VH or VL domain. Hence, the antigen binding site of a single variable domain is formed by no more than three CDRs. The term "single variable domain" does comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's). Such single variable domains and fragments are most preferably such that they comprise an immunoglobulin fold or are capable for forming, under suitable conditions, an immunoglobulin fold. As such, the single variable domain may for example comprise a light chain variable domain sequence (e.g. a $V_L$ sequence) or a suitable fragment thereof; or a heavy chain variable domain sequence (e.g. a $V_H$ sequence or $V_{HH}$ sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In one aspect of the invention, the single variable domains are light chain variable domain sequences (e.g. a $V^L$ sequence), or heavy chain variable domain sequences (e.g. a $V_H$ sequence); more specifically, the single variable domains can be heavy chain variable domain sequences that are derived from a conventional four-chain antibody or heavy chain variable domain sequences that are derived from a heavy chain antibody.

The single variable domain may be a domain antibody (or an amino acid sequence that is suitable for use as a domain antibody), a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$ sequence) [Note: Nanobody® and Nanobodies® are registered trademarks of Ablynx N.V.], other single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-546), to Holt et al. 2003 (Trends Biotechnol. 21(11): 484-490); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629).

In particular, the amino acid sequence of the invention may be a Nanobody or a suitable fragment thereof. For a further description of $V_{HH}$'s and Nanobodies, reference is made to the review article by Muyldermans 2001 (Reviews in Molecular Biotechnology 74: 277-302); as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular $V_{HH}$ sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101,985 and WO 08/142,164.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Thus, in the meaning of the present invention, the term "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

The term "single variable domain" also encompasses variable domains of different origin, comprising mouse, rat, rabbit, donkey, human and camelid variable domains; as well as fully human, humanized or chimeric variable domains. For example, the invention comprises camelid variable domains and humanized camelid variable domains, or camelized variable domains, e.g. camelized dAb as described by Ward et al (see for example WO 94/04678 and Davies and Riechmann (1994, FEBS Lett. 339(3): 285-290) and (1996, Protein Eng. 9(6): 531-537)). Moreover, the invention comprises fused variable domains, e.g. forming a multivalent and/or multispecific construct (for multivalent and multispecific polypeptides containing one or more $V_{HH}$ domains and their preparation, reference is also made to Conrath et al. 2001 (J. Biol. Chem. 276: 7346-7350) as well as to for example WO 96/34103 and WO 99/23221).

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

The single variable domains provided by the invention are preferably in essentially isolated form (as defined herein), or form part of a polypeptide of the invention (as defined herein), which may comprise or essentially consist of one or more single variable domains and which may optionally further comprise one or more further amino acid sequences (all optionally linked via one or more suitable linkers). For example, and without limitation, the one or more single variable domains may be used as a binding unit in such a polypeptide, which may optionally contain one or more further amino acid sequences that can serve as a binding unit (i.e. against one or more other targets), so as to provide a monovalent, multivalent or multispecific polypeptide of the invention, respectively as e.g. described in WO 08/101,985, WO 08/142,164, WO 09/068,625, WO 09/068,627 and WO 08/020,079. Such a protein or polypeptide may also be in essentially isolated form (as defined herein) and the methods of the present invention for the expression and/or production of single variable domains equally apply to polypeptides comprising one or more single variable domains.

According to the invention, the term "single variable domain" may comprise constructs comprising two or more antigen binding units in the form of single variable domain, as outlined above. For example, two (or more) variable domains with the same or different antigen specificity can be linked to form e.g. a bivalent, trivalent or multivalent construct. By combining variable domains of two or more specificities, bispecific, trispecific etc. constructs can be formed. For example, a variable domain according to the invention may comprise two variable domains directed against target A, and one variable domain against target B. Such constructs and modifications thereof, which the skilled person can readily envisage, are all encompassed by the term variable domain as used herein and are also referred to as "polypeptide of the invention" or "polypeptides of the invention".

The stable formulations of the present invention comprise polypeptides of the invention at high concentration (as defined further) and still exhibit little to no aggregation and high stability during transportation and/or long periods of storage. In addition to the polypeptide of the invention, the formulations of the present invention comprise at least an aqueous carrier and a buffer.

A "high concentration of polypeptide", a "polypeptide at high concentration" as used in the present invention means that the concentration of the polypeptide of the invention is at least 0.7 mM, at least 0.8 mM, at least 0.9 mM, at least 1.0 mM, at least 1.1 mM, at least 1.2 mM, at least 1.3 mM, at least 1.4 mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.2 mM, at least 3.4 mM, at least 3.6 mM. In other words, the concentration of the polypeptide is 0.7 mM or higher, 0.8 mM or higher, 0.9 mM or higher, 1.0 mM or higher, 1.1 mM or higher, 1.2 mM or higher, 1.3 mM or higher, 1.4 mM or higher, 1.5 mM or higher, 1.6 mM or higher, 1.7 mM or higher, 1.8 mM or higher, 1.9 mM or higher, 2.0 mM or higher, 2.1 mM or higher, 2.2 mM or higher, 2.3 mM or higher, 2.4 mM or higher, 2.5 mM or higher, 2.6 mM or higher, 2.7 mM or higher, 2.8 mM or higher, 2.9 mM or higher, 3.0 mM or higher, 3.2 mM or higher, 3.4 mM or higher, 3.6 mM or higher. In a specific aspect, the concentration of the polypeptide is about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.2 mM, about 3.4 mM, about 3.6 mM. In another specific aspect, the concentration of the polypeptide is between 0.7 and 3.6 mM, between 0.8 and 3.6 mM, between 0.9 and 3.6 mM, between 1.0 and 3.6 mM, between 1.2 and 3.6 mM, between 1.3 and 3.6 mM, between 1.4 and 3.6 mM, between 1.5 and 3.6 mM, between 1.5 and 2.5 mM, between 1.5 and 2.2 mM, between 1.5 and 2.0 mM, between 1.5 and 1.8 mM. In a specific aspect, a formulation of the invention comprises about 1.6 mM of polypeptide of the invention.

A "high concentration of polypeptide", a "polypeptide at high concentration" as used in the present invention also means that the concentration of the polypeptide of the invention is at least 30 mg/ml, at least 40 mg/ml, at least 50 mg/ml, at least 60 mg/ml, at least 65 mg/ml, at least 70 mg/ml, at least 80 mg/ml, at least 90 mg/ml, at least 100 mg/ml, at least 110 mg/ml, at least 120 mg/ml, at least 130 mg/ml, at least 140 mg/ml, at least 150 mg/ml. In other words, the concentration of the polypeptide is 30 mg/ml or higher, 40 mg/ml or higher, 50 mg/ml or higher, 60 mg/ml or higher, 65 mg/ml or higher, 70 mg/ml or higher, 80 mg/ml or higher, 90 mg/ml or higher, 100 mg/ml or higher, 110 mg/ml or higher, 120 mg/ml or higher, 130 mg/ml or higher, 140 mg/ml or higher, 150 mg/ml or higher. In another specific aspect, the concentration of the polypeptide is between 30 and 150 mg/ml, between 40 and 150 mg/ml, between 50 and 150 mg/ml, between 60 and 150 mg/ml, between 65 and 150 mg/ml, between 65 and 100 mg/ml, between 65 and 90 mg/ml, between 65 and 80 mg/ml, between 65 and 70 mg/ml. In a specific aspect, a formulation of the invention comprises about 65 mg/ml of polypeptide of the invention.

However, it should be clear to one skilled in the art that the formulation of the invention can also be used at lower concentrations of polypeptide such as e.g. from 1 to 10 mg/ml or from 1 to 20 mg/ml such as 1 mg/ml, 2 mg/ml, 5 mg/ml, 10 mg/ml, 15 mg/ml or 20 mg/ml. Accordingly, the same buffer solution may contain lower concentrations of the polypeptide of the invention such as e.g. from 1 to 10 mg/ml or from 1 to 20 mg/ml such as 1 mg/ml, 2 mg/ml, 5 mg/ml, 10 mg/ml, 15 mg/ml or 20 mg/ml, which concentrations may for example be useful in other forms of administration, such as other forms of parenteral administration (i.e. non subcutaneous administration such as e.g. intravenous, intramuscular, intracranial, etc.).

The carrier used in the formulation of the invention should be a liquid carrier. Preferably the carrier is an aqueous carrier such as e.g. distilled water, MilliQ water or Water for Injection (WFI).

The formulation may be buffered by phosphate. The concentration of phosphate which is included in the formulations of the invention may range from 1 mM to 100 mM, 1 mM to 75 mM, 5 mM to 75 mM, 5 mM to 50 mM, 10 mM to 50 mM, 10 mM to 25 mM, 10 mM to 20 mM. In a specific aspect, the concentration of phosphate which is included in the formulations of the invention is 1 mM, 2 mM, 5 mM, 10 mM, 15 mM, 20 mM, 25 mM, 50 mM, 75 mM, or 100 mM. Any form of phosphate may be used suitable for formulation and parenteral administration. Preferably disodium hydrogen phosphate ($Na_2HPO_4$) is used. The purity of phosphate should be at least 98%, at least 99%, or at least 99.5%. As used herein, the term "purity" in the context of phosphate refers to chemical purity of phosphate as understood in the art, e.g., as described in The Merck Index, 13th ed., O'Neil et al. ed. (Merck & Co., 2001). In a specific aspect, a formulation of the invention comprises 10 mM phosphate buffer, such as 10 mM disodium hydrogen phosphate.

Apart from or in addition to phosphate, acetate buffers may be used in the formulations of the present invention at concentration ranges from 1 mM to 100 mM, 1 mM to 75 mM, 5 mM to 75 mM, 5 mM to 50 mM, 10 mM to 50 mM, 10 mM to 25 mM, 10 mM to 20 mM. In a specific aspect, the concentration of acetate which is included in the formulations of the invention is 1 mM, 2 mM, 5 mM, 10 mM, 15 mM, 20 mM, 25 mM, 50 mM, 75 mM, or 100 mM. Any form of acetate may be used suitable for formulation and parenteral administration. The purity of acetate should be at least 98%, at least 99%, or at least 99.5%. As used herein, the term "purity" in the context of acetate refers to chemical purity of acetate as understood in the art, e.g., as described in The Merck Index, 13th ed., O'Neil et al. ed. (Merck & Co., 2001). In a specific aspect, a formulation of the invention comprises 10 mM acetate buffer.

The pH of the formulation generally should not be equal to the isoelectric point of the particular polypeptide and may range from about 4.0 to about 8.0, or may range from about 5.0 to about 7.5, preferably from 5.5 to 7.0. In a specific aspect, a formulation of the invention may have a pH of about 7.0. In another specific aspect, a formulation of the invention may have a pH of about 5.5. In a preferred aspect, the formulation of the invention comprises a phosphate buffer at pH 7.0. In another preferred aspect, the formulation of the invention comprises a phosphate buffer pH 7.0 at 10 mM. In another preferred aspect, the formulation of the invention comprises an acetate buffer at pH 5.5. In another preferred aspect, the formulation of the invention comprises an acetate buffer pH 5.5 at 10 mM.

It will be understood by one skilled in the art that the formulations of the invention may be isotonic or slightly hypotonic with human blood, i.e. the formulations of the invention have essentially the same or a slightly lower osmotic pressure as human blood. Such isotonic or slightly hypotonic formulations generally have an osmotic pressure from about 240 mOSm/kg to about 320 mOSm/kg, such as about 240 mOSm/kg or higher, 250 mOSm/kg or higher or 260 mOSm/kg or higher.

Tonicity of a formulation is adjusted by the use of tonicity modifiers. "Tonicity modifiers" are those pharmaceutically acceptable inert substances that can be added to the formulation to provide an isotonicity of the formulation. Preferred tonicity modifiers in the formulation of the invention are salts.

Accordingly, the formulation of the invention may also comprise a salt. Without being limiting, the salt may be selected from the group consisting of: NaCl, KCl, CaCl$_2$, and MgCl$_2$. In a specific aspect, the salt is NaCl. In another specific aspect, the salt is not KCl. The concentration of salt (preferably NaCl) that may be included in the formulations of the invention may range from 10 mM to 200 mM, 10 mM to 150 mM, 50 mM to 150 mM, 100 mM to 150 mM, or 100 mM to 120 mM. In a specific aspect, the concentration of salt (preferably NaCl) which may be included in the formulations of the invention may be about 10 mM, about 25 mM, about 50 mM, about 75 mM, about 100 mM, about 110 mM, about 120 mM, about 150 mM, or about 200 mM. In a specific embodiment, the concentration of salt (preferably NaCl) included in the formulations of the invention may be about 115 mM. The purity of NaCl may be at least 98%, at least 99%, or at least 99.5%. As used herein, the term "purity" in the context of NaCl refers to chemical purity of NaCl as understood in the art, e.g., as described in The Merck Index, 13th ed., O'Neil et al. ed. (Merck & Co., 2001).

The formulations of the present invention may further comprise other excipients, such as saccharides (e.g., sucrose, mannose, trehalose, etc.), polyols (e.g., mannitol, sorbitol, etc.) and surfactants (e.g., Tween20 or Tween80). In a preferred aspect, the formulation of the invention comprises a surfactant. In a specific aspect, the surfactant is Tween20 or Tween80, which is at a concentration ranging from between about 0% to about 0.1% (v:v), 0.001% (v:v) to about 0.1% (v:v), or about 0.01% (v:v) to about 0.1% (v:v) of the formulation. In a specific embodiment, the surfactant is Tween20 or Tween80, which is at a concentration of 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v).

In certain embodiments, a formulation of the invention may comprise between about 30 mg/ml and about 150 mg/ml of SEQ ID NO: 1, between about 10 mM and about 50 mM sodium hydrogen phosphate (such as disodium hydrogen phosphate/Na$_2$HPO$_4$), between about 50 mM and about 150 mM NaCl and has a pH of between about 5.5 and about 7.0. In a further embodiment, a formulation of the invention may comprise about 65 mg/ml SEQ ID NO: 1, about 10 mM sodium hydrogen phosphate, about 115 mM NaCl and has a pH of about 7.0. In another specific embodiment, a formulation of the invention comprises about 65 mg/ml of SEQ ID NO: 1, about 10 mM sodium hydrogen phosphate (such as disodium hydrogen phosphate; Na$_2$HPO$_4$), about 115 mM NaCl and about 0.01% Tween80, and has a pH of about 7.0.

The formulations of the present invention exhibit stability under at least one or more of the following stress conditions:
  multiple (up to 10) freeze/thaw cycles;
  storage at a temperature of −20±5° C. up to at least 3 months (preferably at least 6 months, at least 9 months, at least 1 year, 1.5 year or even 2 years or more);
  storage at a temperature of 2-8° C. up to at least 3 months (preferably at least 6 months, at least 9 months, at least 11 months, at least 1 year, 1.5 year or even 2 years or more);
  storage at a temperature of 25±5° C. up to at least 6 weeks;
  storage at a temperature of 37±5° C. up to at least 2 weeks (preferably at least 4 weeks, more preferably at least 6 weeks, most preferably at least 8 weeks or more);
  mechanical stress.

Preferably the formulation of the invention is stable under one or more of the following forms of mechanical stress:
  shaking the formulation during 10 s to 1 min;
  pushing the formulation through a needle (25 G, preferably 26 G, more preferably 27 G, even more preferably 28 G, most preferably 29 G or more) with a syringe (the syringe used can be any commercially available syringe, such as e.g. a 1 ml, 2 ml, 3 ml, 4 ml, 5 ml, 10 ml, 20 ml, 30 ml, 40 ml up to 50 ml syringe);
  rotating for two days at 10 rpm; and/or
  stirring for 1 hour at room temperature and 2 days at 4° C. at least 10 rpm (such as 50 rpm, 100 rpm or more).

A "freeze/thaw cycle" or "F/T cycle" is defined as the freezing of a sample in a freezer (−20±5° C.) or ultrafreezer (below −64° C. (such as e.g. at −80° C.)) until the sample is solid, followed by thawing at room temperature until all ice crystals have visually disappeared. In one aspect, the formulation of the invention exhibits stability under multiple (up to 10) freeze/thaw cycles. The formulation of the invention may exhibit stability under at least 1, at least 2, at least 3, at least 5 to up to at least 10 freeze/thaw cycles, such as e.g. 10 cycles at −20° C., 10 cycles at −20° C., 2 cycles at −80° C.+1 cycle at −20° C. or 2 cycles at −80° C. 6 cycles at −20° C.

In another aspect, the formulation of the invention exhibits stability under storage at a temperature of −20±5° C. The formulation of the invention may exhibit stability under storage at a temperature of −20±5° C. for at least 2 weeks, 3 weeks, 4 weeks, 2 months, up to 3 months and more (preferably at least 6 months, at least 9 months, at least 1 year, 1.5 year or even 2 years or more).

In yet another aspect, the formulation of the invention exhibits stability under storage at a temperature of 2-8° C. The formulation of the invention may exhibit stability under storage at a temperature of 2-8° C. for at least 2 weeks, 3 weeks, 4 weeks, 2 months, up to 3 months, 6 months, 9 months, 11 months, 1 year, 1.5 year or even 2 years and more.

In yet another aspect, the formulation of the invention exhibits stability under storage at a temperature of 25±5° C. The formulation of the invention may exhibit stability under storage at a temperature of 25±5° C. for at least 2 weeks, 3 weeks, 4 weeks, up to 6 weeks and more.

In yet another aspect, the formulation of the invention exhibits stability under storage at a temperature of 37±5° C. The formulation of the invention may exhibit stability under storage at a temperature of 37±5° C. for at least 2 weeks, 3 weeks, 4 weeks, 6 weeks, up to 8 weeks and more.

As is known to one skilled in the art, the temperatures indicated in this text can be subject to normal variations.

In yet another aspect, the formulation of the invention exhibits stability under one or more forms of mechanical and/or shear stress. Mechanical stress as used in the present invention can be any form of external force applied on the formulation that may affect the stability of the polypeptide present in the formulation. Without being limiting, the mechanical stress applied to the solution include shear stress, stir stress, shake stress, rotation stress, etc. The formulation of the invention may for example be shaken during at least 10 s, 20 s, 30 s, 40 s, 50 s up to 1 minute or more. The formulation of the invention may be pushed through a syringe (the syringe used can be any commercially available syringe, such as e.g. a 1 ml, 2 ml, 3 ml, 4 ml, 5 ml, 10 ml, 20 ml, 30 ml, 40 ml up to 50 ml syringe) with a needle once, twice, three times, four times, five times up to 10 times or more. Preferably the needle has a size of 25 G (such as 26 G, 27 G, 28 G, 29 G, 30 G) or more. More preferably the size of the needles is 276 or more. The formulation of the invention may be rotated for 1 hour, 2 hours, 6 hours, 12 hours, 1 day up to two days or more at 10 rpm. The formulation of the invention may be stirred for 1 hour at room temperature and 1 to 2 days or more at 2-8° C. The speed of stirring is preferably above 10 rpm, such as e.g. 50 rpm, 100 rpm or more.

Preferably, the formulations of the present invention are stable under more than one of the above stress conditions, such as at least two, at least three, at least four, at least five, at least six, at least seven, at least eight or most preferably under all of the above stress conditions.

Stability of the formulations can be assessed by various analytical and/or immunological methods known in the art. The protein content of the polypeptides of the invention can, for example be detected by spectrophotometrical methods.

SDS-PAGE allows the visualization of the polypeptides in a given sample via direct staining. SDS-PAGE is used to separate proteins according to their size. Both reducing and non-reducing SDS-PAGE analysis can be performed.

The molecular size distribution and the relative amounts of polypeptide of the invention and protein impurities can be determined by Size Exclusion High Performance Liquid Chromatography (SE-HPLC). The relative amount of a specific protein impurity, expressed as area %, can be calculated by dividing the peak area corresponding to the protein impurity by the total integrated area. SE-HPLC methods are known to the skilled person and are also described in the Example section, Reversed Phase High Performance Liquid chromatography (RP-HPLC) separates molecules with respect to differences in hydrophobicity and is based on the reversible interaction between the molecule and the hydrophobic stationary phase. In this assay a Zorbax 300SB-C3 column (Agilent Technologies, Palo Alto, US) can be used. The relative amount of a specific protein impurity, expressed as area %, can be calculated by dividing the peak area corresponding to the protein impurity by the total integrated area. RP-HPLC methods are known to the skilled person and are also described in the Example section.

Polypeptides of the invention and their charge variants can be separated by ion Exchange High Performance Liquid Chromatography (IEX-HPLC). Also potential impurities can be detected with this method. The relative amount of a specific protein impurity, expressed as area %, can be calculated by dividing the peak area corresponding to the protein impurity by the total integrated area. IEX-HPLC methods are known to the skilled person and are also described in the Example section.

The polypeptides present in the formulations of the invention preferably do not form pyroglutamate at the N-terminal glutamic acid. The formation of pyroglutamate in the sample can e.g. be measured by RP-HPLC. For example, analysis by RP-HPLC of a formulation containing SEQ ID NO: 1 after storage for 8 weeks at a temperature of 37° C., showed the formation of pyroglutamate as a separate peak at 18-19 minutes. Preferably in the formulation of the invention, less than 10% (more preferably less than 5%, even more preferably less than 3%, most preferably less than 1%) of the polypeptides form pyroglutamate at the N-terminal glutamic add (e.g. as assessed by RP-HPLC) under one or more of the above stress conditions.

The polypeptides present in the formulations of the invention also preferably do not form dimers. The formation of dimers in the sample can e.g. be measured by SE-HPLC. For example, analysis in SE-HPLC of a formulation containing SEQ ID NO 1 after storage for 8 weeks at a temperature of 37° C., showed the formation of a separate peak eluting at an apparent molecular weight of 44 kDa in comparison with molecular weight markers, while the monomeric polypeptide eluted between the 44 and 17 kDa molecular weight markers. This separate peak at 44 kDa represents a dimeric form of SEQ ID NO: 1. Preferably in the formulation of the invention, less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage under one or more of the above stress conditions.

Preferably in the formulation of the invention, less than 10% (more preferably less than 5%, even more preferably less than 3%, most preferably less than 1%) of the polypeptides forms pyroglutamate at the N-terminal glutamic acid (e.g. as assessed by RP-HPLC) and less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage under one or more of the above stress conditions.

Apart from this and/or in addition, the formulations of the present invention show only low to undetectable levels of aggregation even during storage under one or more of the above stress conditions. For example, in the formulation of the invention, no more than 5%, no more than 4%, no more than 3%, no more than 2%, no more than 1%, and most preferably no more than 0.5% of the polypeptide forms an aggregate after storage under one or more of the above stress conditions.

Aggregation as used in the present invention means the development of high molecular weight aggregates, i.e. aggregates with an apparent molecular weight in SE-HPLC analysis of more/higher than the 44 kDa. As described above, 44 kDa is the apparent molecular weight observed in SE-HPLC analysis for dimers. Aggregation can be assessed by various methods known in the art. Without being limiting, examples include SE-HPLC, analytical ultracentrifugation, dynamic light scattering and/or subvisible particle counting.

In an analytical ultracentrifuge, a sample being spun can be monitored in real time through an optical detection system, using ultraviolet light absorption and/or interference optical refractive index sensitive system. This allows the operator to observe the evolution of the sample concentration versus the axis of rotation profile as a result of the applied centrifugal field. With modern instrumentation, these observations are electronically digitized and stored for further mathematical analysis. Two kinds of experiments are commonly performed on these instruments: sedimentation velocity experiments and sedimentation equilibrium experiments.

Sedimentation velocity experiments aim to interpret the entire time-course of sedimentation, and report on the shape and molar mass of the dissolved macromolecules, as well as their size-distribution (Perez-Ramirez and Steckert (2005) Therapeutic Proteins: Methods and Protocols. C. M. Smales and D. C. James, Eds. Vol. 308: 301-318. Humana Press Inc, Totowa, N.J., US.). The size resolution of this method scales approximately with the square of the particle radii, and by adjusting the rotor speed of the experiment size-ranges from 100 Da to 10 GDa can be covered. Sedimentation velocity experiments can also be used to study reversible chemical equilibria between macromolecular species, by either monitoring the number and molar mass of macromolecular complexes, by gaining information about the complex composition from multi-signal analysis exploiting differences in each components spectroscopic signal, or by following the composition dependence of the sedimentation rates of the macromolecular system, as described in Gilbert-Jenkins theory.

Sedimentation equilibrium experiments are concerned only with the final steady-state of the experiment, where sedimentation is balanced by diffusion opposing the concentration gradients, resulting in a time-independent concentration profile. Sedimentation equilibrium distributions in the centrifugal field are characterized by Boltzmann distributions. This experiment is insensitive to the shape of the macromolecule, and directly reports on the molar mass of the macromolecules and, for chemically reacting mixtures, on chemical equilibrium constants.

The kinds of information that can be obtained from an analytical ultracentrifuge include the gross shape of macromolecules, the conformational changes in macromolecules, and size distributions of macromolecular samples. For macromolecules, such as proteins, that exist in chemical equilibrium with different non-covalent complexes, the number and subunit stoichiometry of the complexes and equilibrium constant constants can be studied. (see also Scott D. J., Harding S. E. and Rowe A. J. Analytical Ultracentrifugation Techniques and Methods, RSC Publishing)

Dynamic light scattering (also known as Photon Correlation Spectroscopy or Quasi-Elastic Light Scattering) is a technique in physics, which can be used to determine the size distribution profile of small particles in solution. When a beam of light passes through a colloidal dispersion, the particles or droplets scatter some of the light in all directions. When the particles are very small compared with the wavelength of the light, the intensity of the scattered light is uniform in all directions (Rayleigh scattering); for larger particles (above approximately 250 nm diameter), the intensity is angle dependent (Mie scattering). If the light is coherent and monochromatic, as from a laser for example, it is possible to observe time-dependent fluctuations in the scattered intensity using a suitable detector such as a photomultiplier capable of operating in photon counting mode.

These fluctuations arise from the fact that the particles are small enough to undergo random thermal (Brownian) motion and the distance between them is therefore constantly varying. Constructive and destructive interference of light scattered by neighbouring particles within the illuminated zone gives rise to the intensity fluctuation at the detector plane which, as it arises from particle motion, contains information about this motion. Analysis of the time dependence of the intensity fluctuation can therefore yield the diffusion coefficient of the particles from which, via the Stokes Einstein equation, knowing the viscosity of the medium, the hydrodynamic radius or diameter of the particles can be calculated. (see also Berne B. J. and Pecora R. Dynamic Light Scattering With Applications to Chemistry, Biology and Physics, Dover Publications)

Aggregation can also be measured by the PAMAS SVSS-C (Small Volume Syringe System-C) instrument (PArtikelMess—und AnalyseSysteme GMBH), which is a particle size distribution analyzer for low viscous fluids. It uses the principle of light obscuration to detect sub-visible particles in the size range 1 µm-200 µm. The validation criteria/specified limits of the European Pharmacopoeia (EP<2.9.19 Particulate Contamination: sub-visible particles) for small and large volume parenterals are defined by the total counts per container:

For particles >10 µm, no more than 6000 counts per container

For particles >25 µm, no more than 600 counts per container

The OD320/OD280 ratio is also a measure for turbidity or the presence of particulates in the sample. In a preferred aspect, the OD320/OD280 ratio of the formulation of the invention should be 0.05 or lower, preferably 0.01 or lower, such as 0.005 or lower.

The tendency for aggregate formation of a polypeptide in a certain formulation can also be measured by elastic light scattering. Elastic light scattering can be measured in a spectrofluorometer (e.g. excitation and emission wavelength 500 nm) by temperature-induced denaturation as measured e.g. at an angle of 90°. Preferably the maximum scatter will stay within the absorption detection limit. The scatter should be 1000 abs. or lower, preferably 750 abs or lower, such as 500 abs or lower.

Apart from this and/or in addition, the formulations of the present invention shows only low to undetectable levels of fragmentation and/or degradation even during storage under one or more of the above stress conditions. Fragmentation and degradation can be measured e.g. by SE-HPLC and/or RP-HPLC. For example, analysis in SE-HPLC of a formulation containing SEQ ID NO: 1 after storage for 8 weeks at a temperature of 37° C., showed the formation of some minor postpeaks, representing degradation products of SEQ ID NO: 1. For example, analysis by RP-HPLC of a formulation containing SEQ ID NO: 1 after storage for 8 weeks at a temperature of 37° C., showed the formation of some minor peaks at 8-9 minutes, representing degradation products. Preferably in the formulation of the invention, no more than 5%, no more than 4%, no more than 3%, no more than 2%, no more than 1%, no more than 0.5%, no more than 0.1%, no more than 0.05%, and most preferably no more than 0.01% of the polypeptides shows degradation and/or fragmentation after storage under one or more of the above stress conditions.

Preferably, the polypeptides present in the formulations of the present invention have a solubility of at least 0.7 mM, at least 0.8 mM, at least 0.9 mM, at least 1.0 mM, at least 1.1 mM, at least 1.2 mM, at least 1.3 mM, at least 1.4 mM, at least 1.5 mM, at least 1.6 mM, at least 1.7 mM, at least 1.8 mM, at least 1.9 mM, at least 2.0 mM, at least 2.1 mM, at least 2.2 mM, at least 2.3 mM, at least 2.4 mM, at least 2.5 mM, at least 2.6 mM, at least 2.7 mM, at least 2.8 mM, at least 2.9 mM, at least 3.0 mM, at least 3.2 mM, at least 3.4 mM, at least 3.6 mM and/or at least 30 mg/ml, at least 40 mg/ml, at least 50 mg/ml, at least 60 mg/ml, at least 65 mg/ml, at least 70 mg/ml, at least 80 mg/ml, at least 90 mg/ml, at least 100 mg/ml, at least 110 mg/ml, at least 120 mg/ml, at least 130 mg/ml, at least 140 mg/ml, at least 150 mg/ml.

The techniques of static light scattering (SLS), tangential flow filtration (TFF), Fourier Transform Infrared Spectroscopy (FTIR), circular dichroism (CD), urea-induced protein unfolding techniques, intrinsic tryptophan fluorescence, differential scanning calorimetry (DSC), and/or 1-anilino-8-naphthalenesulfonic acid (ANS) protein binding can also be used to assess the physical properties and stability of polypeptides.

Apart from this and/or in addition, the formulations of the present invention show very little to no loss of potency and/or biological activity of their polypeptides, even during storage under one or more of the above stress conditions.

The potency and/or biological activity of a biological describes the specific ability or capacity of said biological to achieve a defined biological effect. The potency and biological activities of the polypeptides of the invention can be assessed by various assays including any suitable in vitro assay, cell-based assay, in vivo assay and/or animal model known per se, or any combination thereof, depending on the specific disease or disorder involved. Suitable in vitro assays will be clear to the skilled person, and for example include ELISA; FACS binding assay; Biacore; competition binding assay (AlphaScreen®, Perkin Elmer, Massachusetts, USA; FMAT); TRAP assay (osteoclast differentiation assay; Rissanen et al. 2005, J. Bone Miner. Res. 20, Suppl. 1: S256); NF-kappaB reporter gene assay (Mizukami et al. 2002, Mol. Cell. Biol. 22: 992-1000). For example, SEQ ID NO: 1 interacts with RANKL and blocks the interaction of this ligand with RANK, thereby preventing signalization through this receptor. The potency of SEQ ID NO: 1 for blocking the interaction of RANKL with RANK can be determined, e.g. by ELISA, Biacore, AlphaScreen®.

For example, in one embodiment, Biacore kinetic analysis uses Surface Plasmon Resonance (SPR) technology to monitor macromolecular interactions in real time and is used to determine the binding on and off rates of polypeptides of the formulations of the invention to their target. BIAcore kinetic analysis comprises analyzing the binding and dissociation of the target from chips with immobilized polypeptides of the invention on their surface. A typical Biacore kinetic study involves the injection of 250 µL of polypeptide reagent at varying concentration in HBS buffer containing 0.005% Tween20 over a sensor chip surface, onto which has been immobilized the antigen. In the BIAcore 3000 system, the ligands is immobilized on carboxymethylated dextran over a gold surface, while the second partner (analyte) is captured as it flows over the immobilized ligand surface. The immobilized ligands are remarkably resilient and maintain their biological activity. The bound analytes can be stripped from the immobilized ligand without affecting its activity to allow many cycles of binding and regeneration on the same immobilized surface. Interaction is detected in real time via SPR and at high sensitivity. Because the same affinity may reflect different on-rates and off-rates, this instrument excels over most other affinity measuring methods in that it measures on-rates (ka) and off-rates (kd). Concentration determination experiments are also feasible.

The formulations of the present invention exhibit almost no loss in biological activities of the polypeptide during the prolonged storage under the condition described above, as assessed by various immunological assays including, for example, enzyme-linked immunosorbent assay (ELISA) and Surface Plasmon Resonance to measure the ability of the polypeptide to specifically bind to an antigen. The polypeptides present in the formulations of the present invention retain after the storage for the above-defined periods more than 80%, more than 85%, more than 90%, more than 95%, more than 98%, more than 99%, or more than 99.5% of the initial biological activities (e.g., the ability to bind to RANKL and/or HSA) of the polypeptides prior to the storage. In some embodiments, the polypeptides in the formulations of the invention retain after the storage for the above-defined periods at least 80%, at least 85%, at least 90%, at least 95%, at least 98%, at least 99%, or at least 99.5% of the biological activity (e.g., the ability to bind to RANKL and/or HSA) compared to a reference formulation prior to the storage.

In the formulations of the present invention, at least 80% (preferably at least 85%, at least 90%, at least 95%, at least 98%, at least 99%, or at least 99.5%) of the polypeptides retain their binding activity to RANKL after storage under one or more of the above stress conditions compared to the binding activity prior to storage. Without being limiting, the binding of the polypeptides to RANKL can be determined e.g. by ELISA and/or Biacore. In another aspect, in the formulations of the present invention at least 80% (at least 85%, at least 90%, at least 95%, at least 98%, at least 99%, or at least 99.5%) of the polypeptides retain their binding activity to HSA after storage under one or more of the above stress conditions compared to the binding activity prior to storage. In a preferred aspect, at least 80% (at least 85%, at least 90%, at least 95%, at least 98%, at least 99%, or at least 99.5%) of the polypeptides present in the formulation of the invention retain their binding activity to RANKL and HSA after storage under one or more of the above stress conditions compared to the binding activity prior to storage.

Suitable animal models for determining the potency and/or biological activity of the polypeptides present in the formulations of the invention will be clear to the skilled person, and for example include (SCID)/ARH-77 mouse model (Sordillo and Pearse 2003, Cancer 97 (3 Suppl): 802-812), SCID-hu mouse model of human MM (Sordillo and Pearse 2003, Cancer 97 (3 Suppl): 802-812; Tassone et al. 2005, Blood 106: 713-716), Transgenic mice that overexpress OPG under control of apoE gene promoter and associated enhancer (Simonet et al. 1997, Cell 89: 309-319), Mouse model of sarcoma-induced bone destruction (Honore et al. 2000, Nat. Med. 6: 521-528), Ovariectomized animal models such as, for example, ovariectomized monkeys (Jerome et al. 1995, Bone 17: 4035-4085), ovariectomized mice (Roggia et al. 2001, Proc. Natl. Acad. Sci. USA 20: 13960-13965) or ovariectomized rats and cynomolgus monkeys (Simonet et al. 1997, Cell 89: 309-319; Høegh-Andersen et al. 2004, Arthritis Res. Ther. 6: R169-R180), Rat (animal) models for arthritis (Bendele et al. 1999, Toxicologic Pathology 27: 134-142; Romas et al. 2002, Am. J. Pathol. 161: 1419-1427; Mori et al. 2002, Histochemistry and Cell Biology 117: 283-292) such as models for collagen-induced arthritis or models for adjuvant-induced arthritis, Animal models of tumor-derived PTHrP-induced hypercalcemia (Morony et al. 1999, J. Bone Miner. Res. 14: 1478-1485; Capparelli et al. 2000, Cancer Res. 60: 783-778), Murine model of multiple myeloma (Vanderkerken et al. 2003, Cancer Res. 63: 287-289), Inflammatory Bowel Disease model in mice (Byrne et al. 2005, Gut 54: 78-86), Transgenic mice overexpressing MIF (Onodera et al. 2006, J. Bone Miner. Res. 21: 876-885), Transgenic mice overexpressing soluble osteoclast differentiation factor (sODF) (Mizuno et al. 2002, 20: 337-44), Transgenic mice expressing CSF-1 under control of the CSF-1R promoter/first intron driver [transgene TgN(Csf1r-Csf1)Ers (TgRC) mice] (Wei et al. 2006, J. Leukoc. Biol. 80: 1445-1453), Transgenic mice overexpressing core-binding factor alpha1 (Cbfal) (Geoffroy et al. Mol. Cell Biol. 22: 6222-6233), Transgenic mice overexpressing Decoy receptor 3 (DcR3) (Tang et al. 2007, J. Biol. Chem. 282: 2346-2354), as well as the assays used in the experimental part below and in the prior art cited herein.

Accordingly the present invention provides stable formulations of polypeptides comprising one or more single variable domains (preferably comprising three single variable domains, more preferably comprising two single variable domains that bind RANKL and one single variable domain that binds HSA, such as e.g. SEQ ID NO: 1) at high concentration (as defined above), wherein less than 10% (more preferably less than 5%, even more preferably less than 3%, most preferably less than 1%) of the polypeptide forms pyroglutamate at the N-terminal glutamic acid (e.g. as assessed by RP-HPLC) during storage under stress conditions, such as e.g. at a temperature of 37±5° C. up to at least 2 weeks (preferably at least 4 weeks, more preferably at least 6 weeks, most preferably at least 8 weeks or more);

less than 25% (more preferably less than 20%, even more preferably less than 15% or less than 10%, most preferably 5% or less, such as 3%, 1% or even less than 1%) of the polypeptide forms dimers (e.g. as assessed by SE-HPLC) during storage under stress conditions, such as e.g. at a temperature of 37±5° C. up to at least 2 weeks (preferably at least 4 weeks, more preferably at least 6 weeks, most preferably at least 8 weeks or more);

at least 80% (at least 85%, at least 90%, at least 95%, at least 98%, at least 99%, or at least 99.5%) of the polypeptides retain their binding activity (e.g. as assessed by ELISA and/or Biacore) to at least one of their (preferably to all of their) targets after storage under stress conditions, such as e.g. at 37±5° C. up to 2 weeks (preferably at least 4 weeks, more preferably at least 6 weeks, most preferably at least 8 weeks or more) compared to the binding activity prior to storage; and/or the polypeptide is stable under mechanical stress.

In another aspect, the polypeptide present in the formulation of the invention has a biphasic melting temperature profile wherein one Tm1 is at least 60° C. or more, preferably at least 61° C. or more, more preferably at least 62° C. or more and Tm2 is at least 65° C. or more, preferably at least 66° C. or more, more preferably at least 67° C. or more, as measured by the thermal shift assay and/or differential scanning calorimetry (DSC). Without being limiting, melting point determination can be done by the fluorescence-based thermal shift assay which is based on the fact that upon thermal unfolding the hydrophobic regions of proteins, usually hidden in the core of the protein fold, become accessible for binding to a hydrophobic fluorescent dye. The fluorescence emission of this dye is quenched in aqueous solution, whereas upon binding to the hydrophobic patches of an unfolded protein a sharp increase in the fluorescence yield of the probe is observed. Temperature induced unfolding is typically a two-state process with a sharp transition between the folded and unfolded state, where the melting temperature (Tm) is defined as the temperature at which half of the protein is in the unfolded state, i.e. the first derivative of the fluorescence signal upon gradual heating of the sample is plotted and the observed peak (or peaks when multiple domains and/or variants of the same domain are present) represents the melting temperature. The thermal shift assay can be performed in a typical real-time PCR instrument where melting curves can be recorded accurately in high-throughput mode with only small quantities of protein required.

During a differential scanning calorimetry experiment the sample is heated at a constant rate in an adiabatic environment ($\Delta T=0$). The energy required to keep the temperature difference between a reference and the sample cell at zero is measured and yields the heat capacity as a function of temperature (Cp(T)). The temperature corresponding to the maximum heat capacity represents the melting temperature ($T_m$). If the temperature dependent unfolding process is reversible other thermodynamic parameters such as the unfolding enthalpy ($\Delta H_{unfolding}$) can be determined.

Accordingly, the present invention also relates to stable formulations of polypeptides comprising one or more single variable domains (preferably comprising three single variable domains, more preferably comprising two single variable domains that bind RANKL and one single variable domain that binds HSA, such as e.g. SEQ ID NO: 1) at high concentration (as defined above), wherein less than 10% (more preferably less than 5%, even more preferably less than 3%, most preferably less than 1%) of the polypeptides forms pyroglutamate at the N-terminal glutamic acid (e.g. as assessed by RP-HPLC) during storage under stress conditions, such as e.g. at a temperature of 37±5° C. up to at least 2 weeks (preferably at least 4 weeks, more preferably at least 6 weeks, most preferably at least 8 weeks or more);

less than 25% (more preferably less than 20%, even more preferably less than 15% or less than 10%, most preferably 5% or less, such as 3%, 1% or even less than 1%) of the polypeptide forms dimers (e.g. as assessed by SE-HPLC) during storage under stress conditions, such as e.g. at a temperature of 37±5° C. up to at least 2 weeks (preferably at least 4 weeks, more preferably at least 6 week, most preferably at least 8 weeks or more);

at least 80% (at least 85%, at least 90%, at least 95%, at least 98%, at least 99%, or at least 99.5%) of the polypeptides retain their binding activity (e.g. as assessed by ELISA and/or Biacore) to at least one of their (preferably to all of their) targets after storage under stress conditions, such as e.g. at 37±5° C. up to 2 weeks (preferably at least 4 weeks, more preferably at least 6 weeks, most preferably at least 8 weeks or more) compared to the binding activity prior to storage;

the polypeptide is stable under mechanical stress; and/or the polypeptide has a biphasic melting temperature profile wherein one Tm1 is at least 60° C. or more, preferably at least 61° C. or more, more preferably at least 62° C. or more and Tm2 is at least 65° C. or more, preferably at least 66° C. or more, more preferably at least 67° C. or more, as measured by the thermal shift assay and/or differential scanning calorimetry (DSC).

In a specific aspect, in addition to the polypeptide of the invention at high concentration (as defined above) and the aqueous carrier, the formulation of the invention has a pH of about pH 7.0, and is further characterized that less than 10% (more preferably less than 5%, even more preferably less than 3%, most preferably less than 1%) of the polypeptides present in said formulation forms pyroglutamate at the N-terminal glutamic acid (e.g. as assessed by RP-HPLC) during storage at a temperature of 37±5° C. for up to at least 2 weeks (preferably at least 4 weeks, more preferably at least 6 weeks, most preferably at least 8 weeks or more). Preferably, the formulation of the invention comprises a phosphate buffer (preferably disodium hydrogen phosphate/$Na_2HPO_4$) at pH 7.0, and is further characterized that less than 10% (more preferably less than 5%, even more preferably less than 3%, most preferably less than 1%) of the polypeptides present in said formulation forms pyroglutamate at the N-terminal glutamic acid (e.g. as assessed by RP-HPLC) during storage at a temperature of 37±5° C. for up to at least 2 weeks (preferably at least 4 weeks, more preferably at least 6 weeks, most preferably at least 8 weeks or more). Preferably the concentration of the phosphate buffer is around 10 mM.

In another specific aspect, in addition to the polypeptide of the invention at high concentration (as defined above) and the aqueous carrier, the formulation of the invention has a pH of about 5.5, and is further characterized that less than 10% (more preferably less than 5%, even more preferably less than 3%, most preferably less than 1%) of the polypeptides present in said formulation forms pyroglutamate at the N-terminal glutamic acid (e.g. as assessed by RP-HPLC)

during storage at a temperature of 37±5° C. for up to at least 2 weeks (preferably at least 4 weeks, more preferably at least 6 weeks, most preferably at least 8 weeks or more). Preferably, the formulation of the invention comprises an acetate buffer at pH 5.5, and is further characterized that less than 10% (more preferably less than 5%, even more preferably less than 3%, most preferably less than 1%) of the polypeptides present in said formulation forms pyroglutamate at the N-terminal glutamic (e.g. as assessed by RP-HPLC) acid during storage at a temperature of 37±5° C. for up to at least 2 weeks (preferably at least 4 weeks, more preferably at least 6 weeks, most preferably at least 8 weeks or more). Preferably the concentration of the acetate buffer is around 10 mM.

In yet another specific aspect, in addition to the polypeptide of the invention at high concentration (as defined above) and the aqueous carrier, the formulation of the invention has a pH of about 7.0, and is further characterized that less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably, the formulation of the invention comprises a phosphate buffer (preferably disodium hydrogen phosphate/$Na_2HPO_4$) at pH 7.0, and is further characterized that less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably the concentration of the phosphate buffer is around 10 mM.

In yet another specific aspect, in addition to the polypeptide of the invention at high concentration (as defined above) and the aqueous carrier, the formulation of the invention has a pH of about 5.5, and is further characterized that less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably, the formulation of the invention comprises an acetate buffer at pH 5.5, and is further characterized that less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably the concentration of the acetate buffer is around 10 mM.

In yet another specific aspect, in addition to the polypeptide of the invention at high concentration (as defined above) and the aqueous carrier, the formulation of the invention has a pH of about 7.0, and is further characterized that less than 10% (more preferably less than 5%, even more preferably less than 3%, most preferably less than 1%) of the polypeptides present in said formulation forms pyroglutamate at the N-terminal glutamic acid (e.g. as assessed by RP-HPLC) and less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably, the formulation of the invention comprises a phosphate buffer (preferably disodium hydrogen phosphate/$Na_2HPO_4$) at pH 7.0, and is further characterized that less than 10% (more preferably less than 5%, even more preferably less than 3%, most preferably less than 1%) of the polypeptides present in said formulation forms pyroglutamate at the N-terminal glutamic acid (e.g. as assessed by RP-HPLC) and less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably the concentration of the phosphate buffer is around 10 mM.

In yet another specific aspect, in addition to the polypeptide of the invention at high concentration (as defined above) and the aqueous carrier, the formulation of the invention has a pH of about 5.5, and is further characterized that less than 10% (more preferably less than 5%, even more preferably less than 3%, most preferably less than 1%) of the polypeptides present in said formulation forms pyroglutamate at the N-terminal glutamic acid (e.g. as assessed by RP-HPLC) and less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably, the formulation of the invention comprises an acetate buffer at pH 5.5, and is further characterized that less than 10% (more preferably less than 5%, even more preferably less than 3%, most preferably less than 1%) of the polypeptides present in said formulation forms pyroglutamate at the N-terminal glutamic acid (e.g. as assessed by RP-HPLC) and less than 25% (more preferably less than 20%, even more preferably less than 15% or less than 10%, most preferably 5% or less, such as 3%, 1% or even less than 1%) of the polypeptides forms dimers (e.g. as assessed by SE-HPLC) during storage at a temperature of 37±5° C. for up to at least 2 weeks (preferably at least 4 weeks, more preferably at least 6 weeks, most preferably at least 8 weeks or more). Preferably the concentration of the acetate buffer is around 10 mM.

In yet another specific aspect, in addition to the polypeptide of the invention at high concentration (as defined above) and the aqueous carrier, the formulation of the invention has a pH of about 7.0, and is further characterized that at least 80% (at least 85%, at least 90%, at least 95%, at least 98%, at least 99%, or at least 99.5%) of the polypeptides retain their binding activity (as assessed by ELISA and/or Biacore) to RANKL during storage at a temperature of 37±5° C. for up to at least 2 weeks (preferably at least 4 weeks, more preferably at least 6 weeks, most preferably at least 8 weeks or more) compared to the binding activity prior to storage. In a preferred aspect, the formulation of the invention comprises a phosphate buffer at pH 7.0, and is further characterized that at least 80% (at least 85%, at least 90%, at least 95%, at least 98%, at least 99%, or at least 99.5%) of the polypeptides retain their binding activity (e.g. as assessed by ELISA and/or Biacore) to RANKL during storage at a temperature of 37±5° C. for up to at least 2 weeks (preferably at least 4 weeks, more preferably at least 6 weeks, most preferably at least 8 weeks or more) compared to the binding activity prior to storage. Preferably the concentration of the phosphate buffer is around 10 mM.

In yet another specific aspect, in addition to the polypeptide of the invention at high concentration (as defined above) and the aqueous carrier, the formulation of the invention has a pH of about 5.5, and is further characterized that at least 80% (at least 85%, at least 90%, at least 95%, at least 98%, at least 99%, or at least 99.5%) of the polypeptides retain their binding activity (as assessed by ELISA and/or Biacore) to RANKL during storage at a temperature of 37±5° C. for up to at least 2 weeks (preferably at least 4 weeks, more preferably at least 6 weeks, most preferably at least 8 weeks or more) compared to the binding activity prior to storage. In a preferred aspect, the formulation of the invention comprises an acetate buffer at pH 5.5, and is further characterized that at least 80% (at least 85%, at least 90%, at least 95%, at least 98%, at least 99%, or at least 99.5%) of the polypeptides retain their binding activity (as assessed by ELISA and/or Biacore) to RANKL during storage at a temperature of 37±5° C. for up to at least 2 weeks (preferably at least 4 weeks, more preferably at least 6 weeks, most preferably at least 8 weeks or more) compared to the binding activity prior to storage. Preferably the concentration of the acetate buffer is around 10 mM.

In yet another specific aspect, in addition to the polypeptide of the invention at high concentration (as defined above) and the aqueous carrier, the formulation of the invention has a pH of about 7.0, and is further characterized that at least 80% (at least 85%, at least 90%, at least 95%, at least 98%, at least 99%, or at least 99.5%) of the polypeptides retain their binding activity (as assessed by ELISA and/or Biacore) to HSA during storage at a temperature of 37±5° C. for up to at least 2 weeks (preferably at least 4 weeks, more preferably at least 6 weeks, most preferably at least 8 weeks or more) compared to the binding activity prior to storage. In a preferred aspect, the formulation of the invention comprises a phosphate buffer at pH 7.0, and is further characterized that at least 80% (at least 85%, at least 90%, at least 95%, at least 98%, at least 99%, or at least 99.5%) of the polypeptides retain their binding activity (as assessed by ELISA and/or Biacore) to HSA during storage at a temperature of 37±5° C. for up to at least 2 weeks (preferably at least 4 weeks, more preferably at least 6 weeks, most preferably at least 8 weeks or more) compared to the binding activity prior to storage. Preferably the concentration of the phosphate buffer is around 10 mM.

In yet another specific aspect, in addition to the polypeptide of the invention at high concentration (as defined above) and the aqueous carrier, the formulation of the invention has a pH of about 5.5, and is further characterized that at least 80% (at least 85%, at least 90%, at least 95%, at least 98%, at least 99%, or at least 99.5%) of the polypeptides retain their binding activity (as assessed by ELISA and/or Biacore) to HSA during storage at a temperature of 37±5° C. for up to at least 2 weeks (preferably at least 4 weeks, more preferably at least 6 weeks, most preferably at least 8 weeks or more) compared to the binding activity prior to storage. Preferably the concentration of the acetate buffer is around 10 mM.

In yet another specific and most preferred aspect, in addition to the polypeptide of the invention at high concentration (as defined above) and the aqueous carrier, the formulation of the invention has a pH of about 7.0, and is further characterized that at least 80% (at least 85%, at least 90%, at least 95%, at least 98%, at least 99%, or at least 99.5%) of the polypeptides retain their binding activity (as assessed by ELISA and/or Biacore) to RANKL and to HSA during storage at a temperature of 37±5° C. for up to at least 2 weeks (preferably at least 4 weeks, more preferably at least 6 weeks, most preferably at least 8 weeks or more) compared to the binding activity prior to storage. In a preferred aspect, the formulation of the invention comprises a phosphate buffer at pH 7.0, and is further characterized that at least 80% (at least 85%, at least 90%, at least 95%, at least 98%, at least 99%, or at least 99.5%) of the polypeptides retain their binding activity (as assessed by ELISA and/or Biacore) to RANKL and to HSA during storage at a temperature of 37±5° C. for up to at least 2 weeks (preferably at least 4 weeks, more preferably at least 6 weeks, most preferably at least 8 weeks or more) compared to the binding activity prior to storage. Preferably the concentration of the phosphate buffer is around 10 mM.

In yet another specific aspect, in addition to the polypeptide of the invention at high concentration (as defined above) and the aqueous carrier, the formulation of the invention has a pH of about 5.5, and is further characterized that at least 80% (at least 85%, at least 90%, at least 95%, at least 98%, at least 99%, or at least 99.5%) of the polypeptides retain their binding activity (as assessed by ELISA and/or Biacore) to RANKL and to HSA during storage at a temperature of 37±5° C. for up to at least 2 weeks (preferably at least 4 weeks, more preferably at least 6 weeks, most preferably at least 8 weeks or more) compared to the binding activity prior to storage. In a preferred aspect, the formulation of the invention comprises an acetate buffer at pH 5.5, and is further characterized that at least 80% (at least 85%, at least 90%, at least 95%, at least 98%, at least 99%, or at least 99.5%) of the polypeptides retain their binding activity (as assessed by ELISA and/or Biacore) to RANKL and to HSA during storage at a temperature of 37±5° C. for up to at least 2 weeks (preferably at least 4 weeks, more preferably at least 6 weeks, most preferably at least 8 weeks or more) compared to the binding activity prior to storage. Preferably the concentration of the acetate buffer is around 10 mM.

In another specific aspect, in addition to the polypeptide of the invention at high concentration (as defined above), the aqueous carrier and the buffer (preferably a phosphate buffer at pH 7.0 or an acetate buffer at pH 5.5) the formulation of the invention comprises a surfactant, and is further characterized that the polypeptides present in the formulation are stable under mechanical stress. In a specific aspect, the formulation of the invention comprises Tween20 or Tween80 (at a concentration ranging from about 0% to about 0.1% (v:v), about 0.001% (v:v) to about 0.1% (v:v), or about 0.01% (v:v) to about 0.1% (v:v) such as 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)) and is characterized that the polypeptides present in the formulation are stable under mechanical stress.

In a preferred aspect, the formulation of the invention comprises Tween80 (at a concentration of 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)) and is characterized that the polypeptides present in the formulation of the invention are stable when shaking the formulation during at least 10 s, 20 s, 30 s, 40 s, 50 s up to 1 minute of more. In another preferred aspect, the formulation of the invention comprises Tween80 (at a concentration of 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)) and is characterized that the polypeptides present in the formulation of the invention are stable when pushing the formulation through a syringe (the syringe used can be any commercially available syringe, such as e.g. a 1 ml, 2 ml, 3 ml, 4 ml, 5 ml, 10 ml, 20 ml, 30 ml, 40 ml up to 50 ml syringe) with needle size of 25 G or more (such as 26 G, 27 G, 28 G, 29 G, 30 G or more, preferably 270 or more) once, twice, three times, four times, five times up to 10 times or more. In another preferred aspect, the formulation of the invention comprises Tween80 (at a concentration of 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)) and is characterized that the polypeptides present in the formulation of the invention are stable when rotating the formulation for 1 hour, 2 hours, 6 hours, 12 hours, 1 day up to two days or more at 10 rpm. In another preferred aspect, the formulation of the invention comprises Tween80 (at a concentration of 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, preferably 0.01% (v:v)) and is characterized that the polypeptides present in the formulation of the invention are stable when stirring the formulation for 1 hour at room temperature and 1 to 2 days or more at 2-8° C. at least 10 rpm (such as 50 rpm, 100 rpm or more).

Accordingly, in a specific aspect, the formulation of the invention comprises:
30-150 mg/ml of SEQ ID NO: 1;
10-20 mM disodium hydrogen phosphate ($Na_2HPO_4$);
100-150 mM Sodium chloride (NaCl);
0.01% Tween80 (v:v);
and is further characterized that:
less than 10% (more preferably less than 5%, even more preferably less than 3%, most preferably less than 1%) of the polypeptide forms pyroglutamate at the N-terminal glutamic acid (as assessed by RP-HPLC) during storage at a temperature of 37±5° C. up to at least 2 weeks (preferably at least 4 weeks, more preferably at least 6 weeks, most preferably at least 8 weeks or more);
less than 25% (more preferably less than 20%, even more preferably less than 15% or less than 10%, most preferably 5% or less, such as 3%, 1% or even less than 1%) of the polypeptide forms dimers (as assessed by SE-HPLC) during storage at a temperature of 37±5° C. up to at least 2 weeks (preferably at least 4 weeks, more preferably at least 6 weeks, most preferably at least 8 weeks or more);
at least 80% (at least 85%, at least 90%, at least 95%, at least 98%, at least 99%, or at least 99.5%) of the polypeptides retain their binding activity (as assessed by ELISA and/or Biacore) to at least one of their targets after storage at 37±5° C. up to 2 weeks (preferably at least 4 weeks, more preferably at least 6 weeks, most preferably at least 8 weeks or more) compared to the binding activity prior to storage; and/or
the polypeptide is stable under one or more of the following mechanical stress conditions:
shaking the formulation during 10 s to 1 min;
pushing the formulation through a needle (25 G, preferably 26 G, more preferably 27 G, even more preferably 28 G, most preferably 29 G or more) with a syringe (the syringe used can be any commercially available syringe, such as e.g. a 1 ml, 2 ml, 3 ml, 4 ml, 5 ml, 10 ml, 20 ml, 30 ml, 40 ml up to 50 ml syringe);
rotating for two days at 10 rpm; and/or
stirring for 1 hour at room temperature and 2 days at 4° C. at least 10 rpm (such as 50 rpm, 100 rpm or more).

An example of a preferred formulation of the invention with these characteristics comprises 65 mg/ml of SEQ ID NO: 1, 10 mM disodium hydrogen phosphate ($Na_2HPO4$), 115 mM Sodium chloride (NaCl) and 0.01% Tween80 (v:v).

General methods for producing the single variable domains and/or polypeptides present in the formulations of the invention are known to the skilled person and/or have been described in the art. The single variable domains and/or polypeptides can be produced in any host known to the skilled person. For example but without being limiting, the single variable domains and/or polypeptides can be produced in prokaryotic hosts among which *E. coli* or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*. Production of Nanobodies in prokaryotes and lower eukaryotic hosts such as *Pichia pastoris* has e.g. been described in WO 94/04678, WO 94/25591 and WO 08/142,164. The contents of these applications are explicitly referred to in the connection with general culturing techniques and methods, including suitable media and conditions. The contents of these documents are incorporated by reference. The skilled person can also devise suitable genetic constructs for expression of the polypeptides of the invention in different hosts on the basis of the present application and common general knowledge. The present invention also relates to conditions and genetic constructs described in the art, for example the general culturing methods, plasmids, promoters and leader sequences described in WO 94/25591, WO 08/020,079, Gasser et al. 2006 (Biotechnol. Bioeng. 94: 535); Gasser et al. 2007 (Appl. Environ. Microbiol. 73: 6499); or Damasceno et al. 2007 (Microbial. Biotechnol. 74: 381).

More particularly, the method for the expression and/or production of a polypeptide comprising one or more single variable domains at least comprising the steps of:
a) cultivating a host or host cell (as defined herein) under conditions that are such that said host or host cell will multiply;
b) maintaining said host or host cell under conditions that are such that said host or host cell expresses and/or produces the polypeptide;
c) isolating and/or purifying the secreted polypeptide from the medium.

To produce/obtain expression of the polypeptide, the transformed host cell or transformed host organism may generally be kept, maintained and/or cultured under conditions such that the (desired) polypeptide is expressed/produced. Suitable conditions will be clear to the skilled person and will usually depend upon the host cell/host organism used, as well as on the regulatory elements that control the expression of the (relevant) nucleotide sequence. Again, reference is made to the handbooks and patent applications mentioned above.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the polypeptide to be isolated).

In the present invention, the host can be removed from the culture medium by routine means. For example, the host can be removed by centrifugation or filtration. The solution obtained by removal of the host from the culture medium is also referred to as culture supernatant, or clarified culture supernatant. The polypeptides of the invention can be purified from the culture supernatant by standard methods. Standard methods include, but are not limited to chromatographic methods, including size exclusion chromatography, hydrophobic interaction chromatography, ion exchange chromatography, and affinity chromatography. These methods can be performed alone or in combination with other purification methods, e.g. precipitation or gel electrophoresis. The skilled person can devise suitable combinations of purification methods for the polypeptides of the invention on the basis of common general knowledge. For specific examples the art cited herein is referred to.

In one exemplary embodiment, the polypeptides of the invention can be purified from culture supernatant by a combination of affinity chromatography on Protein A, ion exchange chromatography and size exclusion chromatography. Reference to any "step of purification", includes, but is not limited to these particular methods.

More specifically, the polypeptides of the invention can be purified from culture supernatant using a process wherein the clarified supernatant (obtained by centrifugation) is captured on any combination of columns selected from (without being limiting) affinity chromatography resin such as Protein A resin, Cation Exchange Chromatography (CIEC) or an Anion Exchange Chromatography (AIEC) using for example Poros SOHS (FORDS), SOURCE 30S or SOURCE 15S (GE Healthcare), SP Sepharose (GE Healthcare), Capto S (GE Healthcare), Capto MMC (GE Healthcare) or Poros 50HQ (POROS), SOURCE 30Q or SOURCE 15Q (GE Healthcare), Q Sepharose (GE Healthcare), Capto Q and DEAE Sepharose (GE Healthcare), Size exclusion chromatography (SE-HPLC) using for example Superdex 75 or Superdex 200 (GE Healthcare), hydrophobic interaction chromatography (HIC) using for example octyl, butyl sepharose or equivalents, optionally also including a tangential flow filtration (TFF) step. Any combination of columns can be used for the purification of the polypeptides of the invention, such as e.g. Protein A resin followed by Cation Exchange Chromatography or two Cation Exchange Chromatography steps.

The present invention also provides methods for preparing the stable formulations of the invention comprising the polypeptides of the invention. More particularly, the present invention provides methods for preparing stable formulations of such polypeptides, said methods comprising concentrating a fraction containing the purified polypeptide to a final polypeptide concentration of more than 30 mg/ml, 40 mg/ml, 50 mg/ml, 60 mg/ml, 70 mg/ml, 80 mg/ml, 90 mg/ml, 100 mg/ml, or 150 mg/ml, such as e.g. 65 mg/ml using e.g. a semipermeable membrane with an appropriate molecular weight (MW) cutoff (e.g. a 5 kD cutoff for single variable domains; a 10 kD cutoff for bivalent polypeptides comprising two single variable domains; or a 15 kD cutoff for trivalent polypeptides comprising three single variable domains) and diafiltering and/or ultrafiltering to buffer exchange and further concentrate the polypeptide fraction into the formulation buffer using the same membrane. As extensively described above, the formulation buffer of the present invention may further comprise:

a buffer such as a phosphate (preferably disodium hydrogen phosphate) or acetate buffer at a concentration of about 10-20 mM;

a salt such as NaCl at a concentration in the range from about 0 mM to about 200 mM, preferably 100 mM to 150 mM, such as around 115 mM.

The pH of the formulation may range from about 5.5 to about 7.0, preferably about 7.0.

Surfactant (e.g. Tween20 or Tween80) will be added after the final diafiltration/ultrafiltration step at a concentration in the range of about 0% to about 0.1% (v:v), such as e.g. 0.01% (v:v).

The formulations of the present invention may be sterilized by various sterilization methods, including sterile filtration, radiation, etc. In a specific embodiment, the polypeptide formulation is filter-sterilized with a presterilized 0.2 micron filter.

The formulations of the invention may be lyophilized (freeze dried) if desired. Accordingly, the invention also encompasses lyophilized forms of the formulations of the invention. Preferably the final residual water content of the lyophilized formulation is extremely low, around 1% to 4%.

Freeze-drying works by freezing the material and then reducing the surrounding pressure and adding enough heat to allow the frozen water in the material to sublime directly from the solid phase to gas. Accordingly, the present invention also relates to a method for freeze drying the formulation of the invention. More specifically the present invention relates to a method comprising the steps of:

a) Freezing the formulation of the invention at a temperature of between −50° C. and −80° C.;

b) Lowering the pressure (to the range of a few millibars) and supplying enough heat for the water to sublimate.

The present invention thus also relates to a formulation which is produced by freeze-drying the formulation of the invention.

The formulations of the invention may also be spray dried if desired. Accordingly, the invention also encompasses spray dried forms of the formulations of the invention. Preferably the final residual water content of the spray dried formulation is extremely low, around 1% to 4%.

Spray drying is a method of producing a dry powder from a liquid or slurry by rapidly drying with a hot gas. Spray drying works by dispersing the liquid formulation into a controlled drop size spray and passing hot air as the heated drying media. Accordingly, the present invention also relates to a method for spray drying the formulation of the invention. More specifically the present invention relates to a method comprising the steps of:
  a) dispersing the liquid formulation into a controlled drop size (drop sizes from 10 to 500 micron can be achieved, such as e.g. in the 100 to 200 micron diameter range) spray by use of an atomizer or Spray Nozzle (such as e.g. rotary nozzles, single-fluid pressure swirl nozzles, two-fluid or Ultrasonic Nozzle);
  b) passing a hot drying gas as a co-current or counter-current flow to the spray.

The present invention thus also relates to a formulation which is produced by spray drying the formulation of the invention.

Preferably, the liquid, lyophilized or spray dried formulation of the present invention is supplied in a hermetically sealed container. Liquid formulations may comprise a quantity between 1 ml and 20 ml, preferably about 1 ml, 2 ml, 3 ml, 4 ml, 5 ml, 6 ml, 7 ml, 8 ml, 9 ml, 10 ml, 15 ml, or 20 ml.

The liquid, lyophilized or spray dried formulations of the present invention can be prepared as unit dosage forms by preparing a vial containing an aliquot of the liquid, lyophilized or spray dried formulation for a one time use. For example, a unit dosage of liquid formulation per vial may contain 1 ml, 2 ml, 3 ml, 4 ml, 5 ml, 6 ml, 7 ml, 8 ml, 9 ml, 10 ml, 15 ml, or 20 ml of the formulation. The pharmaceutical unit dosage forms can be made suitable for any form of delivery of the polypeptide of the invention including (without being limiting) parenteral delivery, topical delivery, pulmonary delivery, intranasal delivery, vaginal delivery, enteral delivery, rectal delivery, oral delivery and/or sublingual delivery. In one aspect, the present invention relates to a pharmaceutical unit dosage form suitable for parenteral (such as e.g. intravenous, intraarterial, intramuscular, intracerebral, intraosseous, intradermal, intrathecal, intraperitoneal, subcutaneous, etc) administration to a subject, comprising a formulation of the invention in a suitable container. In a preferred aspect, the pharmaceutical unit dosage form is suitable for subcutaneous administration to a subject. In another preferred aspect, the subject is a human. In a specific embodiment, the liquid formulations of the present invention are formulated into single dose vials as a sterile liquid that contains 65 mg/ml of SEQ ID NO: 1, 10 mM phosphate buffer at pH 7.0, 115 mM sodium chloride and 0.01% Tween80 (v:v).

The amount of a formulation of the present invention which will be effective in the prevention, treatment and/or management of a certain disease or disorder can be determined by standard clinical techniques well-known in the art or described herein. The precise dose to be employed in the formulation will also depend on the route of administration, and should be decided according to the judgment of the practitioner and each patient's circumstances. Effective doses may be extrapolated from dose-response curves derived from in vitro or animal model test systems. For formulations of the polypeptide, encompassed by the invention, the dosage administered to a patient may further be calculated using the patient's weight in kilograms (kg) multiplied by the dose to be administered in mg/kg. For subcutaneous administration of a formulation of the invention comprising 65 mg/ml of polypeptide (such as e.g. SEQ ID NO: 1) a dosage of for example 1-3 mg/kg bodyweight is envisaged.

The required volume (in ml) to be given is then determined by taking the mg dose required divided by the concentration of the polypeptide formulation. The final calculated required volume will be obtained by pooling the contents of as many vials as are necessary into syringe(s) to administer the polypeptide formulation of the invention. For example, for subcutaneous administration of a formulation of the invention comprising 65 mg/ml of polypeptide (such as e.g. SEQ ID NO: 1) it is envisaged that the required volume is around 1-3 ml for a dose of 1-3 mg/kg.

The present invention also encompasses a finished packaged and labelled pharmaceutical product. This article of manufacture or kit includes the appropriate unit dosage form in an appropriate vessel or container such as a glass vial or other container that is hermetically sealed. In one embodiment, the unit dosage form is suitable for intravenous, intramuscular, intranasal, oral, topical or subcutaneous delivery. Thus, the invention encompasses formulations, preferably sterile, suitable for each delivery route. In the case of dosage forms suitable for parenteral administration (such as e.g. subcutaneous administration) the active ingredient, e.g., polypeptide of the invention (such as e.g. SEQ ID NO: 1), is sterile and suitable for administration as a particulate free solution. In other words, the invention encompasses both parenteral solutions and lyophilized or spray dried powders, each being sterile, and the latter being suitable for reconstitution prior to injection.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises the formulation containing the polypeptide. The packaging material includes instruction means which indicate that said polypeptide can be used to prevent, treat and/or manage one or more symptoms associated with the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide of interest, and wherein said packaging material includes instruction means which indicate that said agents can be used to prevent, treat and/or manage the disease or disorder by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises a formulation containing the polypeptide, and wherein said packaging material includes instruction means which indicate that said agents can be used to prevent, treat and/or manage one or more symptoms associated with the disease or disorder by administering specific doses and using specific dosing regimens as described herein.

The formulations, containers, pharmaceutical unit dosages and kits of the present invention may be administered to a subject to prevent, treat and/or manage a specific disease and/or disorder. In a specific aspect, the formulations, containers, pharmaceutical unit dosages and kits of the present invention are administered to a subject to prevent, treat and/or manage a disease and/or disorder associated with or characterized by aberrant expression and/or activity of a certain target or one or more symptoms thereof. In another specific aspect, the formulations, containers, pharmaceutical unit dosages and kits of the present invention are administered to a subject to prevent, treat and/or manage a disease and/or disorder associated with or characterized by aberrant expression and/or activity of RANKL or one or more symptoms thereof.

Diseases and disorders associated with aberrant expression and/or activity of RANKL are for example bone diseases and disorders, and include (without being limiting) the following diseases and disorders: Osteoporosis (McClung 2006, Current Osteoporosis Reports 4: 28-33), including, but not limited to, primary osteoporosis, endocrine osteoporosis (including, but not limited to, hyperthyroidism, hyperparathyroidism (Anandarajah and Schwarz 2006, J. Cell Biochem. 97: 226-232), Cushing's syndrome, and acromegaly), hereditary and congenital forms of osteoporosis (including, but not limited to, osteogenesis imperfecta, homocystinuria, Menkes' syndrome, Riley-Day syndrome), osteoporosis due to immobilization of extremities, glucocorticoid-induced osteoporosis (Locklin et al. 2001, Bone 28 (Suppl.): 580; McClung 2006, Current Osteoporosis Reports 4: 28-33; Anandarajah and Schwarz 2006, J. Cell Biochem. 97: 226-232) and post-menopausal osteoporosis (McClung 2006, Current Osteoporosis Reports 4: 28-33); (Juvenile or Familial) Paget's disease (Candy et al. 2002, Hum. Mol. Genet. 11: 2119-2127; Whyte et al. 2002, J. Bone Miner. Res. 17: 26-29; Whyte et al. 2002, N. Engl. J. Med. 347: 175-184; Johnson-Pais et al. 2003, J. Bone Miner Res. 18: 376-380; Anandarajah and Schwarz 2006, J. Cell Biochem. 97: 226-232; Anandarajah and Schwarz 2006, J. Cell Biochem. 97: 226-232); Osteomyelitis, i.e., an infectious lesion in bone, leading to bone loss; Hypercalcemia (Anandarajah and Schwarz 2006, J. Cell Biochem. 97: 226-232), including, but not limited to, hypercalcemia resulting from solid tumors (including, but not limited to, breast, lung and kidney) and hematologic malignancies (including, but not limited to, multiple myeloma (Sordillo and Pearse 2003, Cancer 97 (3 Suppl): 802-812; Vanderkerken et al. 2003, Cancer Res. 63: 287-289), lymphoma and leukemia), idiopathic hypercalcemia, and hypercalcemia associated with hyperthyroidism and renal function disorders; Bone loss, including but not limited to, osteopenia following surgery, osteopenia induced by steroid administration, osteopenia associated with disorders of the small and large intestine, and osteopenia associated with chronic hepatic and renal diseases; Osteonecrosis, i.e., bone cell death, including, but not limited to, osteonecrosis associated with traumatic injury, osteonecrosis associated with Gaucher's disease, osteonecrosis associated with sickle cell anemia, osteonecrosis associated with systemic lupus erythematosus, osteonecrosis associated with rheumatoid arthritis, osteonecrosis associated with periodontal disease, osteonecrosis associated with osteolytic metastasis, and osteonecrosis associated with other condition; Bone loss associated with arthritic disorders such as psoriatic arthritis, rheumatoid arthritis, loss of cartilage and joint erosion associated with rheumatoid arthritis (Bezerra et al. 2005, Brazilian Journal of Medical and Biological Research 38: 161-170; Anandarajah and Schwarz 2006, J. Cell Biochem. 97: 226-232); Arthritis (Bezerra et al. 2005, Brazilian Journal of Medical and Biological Research 38: 161-170), including inflammatory arthritis (McClung 2006, Current Osteoporosis Reports 4: 28-33), Collagen-induced arthritis (Bezerra et al. 2005, Brazilian Journal of Medical and Biological Research 38: 161-170); Periprosthetic osteolysis (McClung 2006, Current Osteoporosis Reports 4: 28-33; Anandarajah and Schwarz 2006, J. Cell Biochem. 97: 226-232); Cancer-related bone disease (McClung 2006, Current Osteoporosis Reports 4: 28-33); Bone loss associated with aromatase inhibitor therapy (Lewiecki 2006, Expert Opin. Biot. Ther. 6: 1041-1050); Bone loss associated with androgen deprivation therapy (Lewiecki 2006, Expert Opin. Biol. Ther. 6: 1041-1050); Bone loss associated bone metastasis; Bone loss associated with diseases having immune system involvement, such as adult and childhood leukaemias, cancer metastasis, autoimmunity, and various viral infections (Holstead Jones et al. 2002, Ann. Rheum. Dis. 61 (Suppl II): ii32-ii39); Osteopenic disorders such as adult and childhood leukaemia (Oliveri et al. 1999, Henry Ford Hosp. Med. 39: 45-48); chronic infections such as hepatitis C or HIV (Stellon et al. 1985, Gastroenterology 89: 1078-1083); autoimmune disorders such as diabetes mellitus (Piepkorn et al, 1997, Horm. Metab. Res. 29: 584-91), and lupus erythematosus (Seitz et al. 1985, Ann. Rheum Dis. 44: 438-445), allergic diseases such as asthma (Ebeling et al. 1998, J. Bone Min. Res. 13: 1283-1289), lytic bone metastases in multiple cancers such as breast cancer (Coleman 1998, Curr. Opin. Oncol. 10 (Suppl 1): 7-13); Prostate cancer; Myeloma bone disease (Anandarajah and Schwarz 2006, J. Cell Biochem. 97: 226-232); Periodontal infections (Anandarajah and Schwarz 2006, J. Cell Biochem. 97: 226-232); Expansile skeletal hyperphosphatasia (Anandarajah and Schwarz 2006, J. Cell Biochem. 97: 226-232); Bone metastases (Lewiecki 2006, Expert Opin. Biol. Ther. 6: 1041-1050; Anandarajah and Schwarz 2006, J. Cell Biochem. 97: 226-232).

Also encompassed within the scope of the present invention is the prevention and/or treatment with the formulations, containers, pharmaceutical unit dosages and kits of the invention of other diseases and disorders associated with an imbalance in the RANKL/RANK/OPG pathway. Such diseases and disorders include but are not limited to osteoporosis, inflammatory conditions, autoimmune conditions, asthma, rheumatoid arthritis, multiple sclerosis, Multiple myeloma (Sordillo and Pearse 2003, Cancer 97 (3 Suppl): 802-812; Vanderkerken et al. 2003, Cancer Res. 63: 287-289); Vascular diseases (Anandarajah and Schwarz 2006, J. Cell Biochem. 97: 226-232) and Cardiovascular disease (Lewiecki 2006, Expert Opin. Biol. Ther. 6: 1041-1050).

Also encompassed within the scope of the present invention is the prevention and/or treatment with the formulations, containers, pharmaceutical unit dosages and kits of the invention of diseases and disorders associated with osteopetrosis such as osteopetrosis tarda, osteopetrosis congenita and marble bone disease.

The formulations, containers, pharmaceutical unit dosages and kits of the present invention may also be advantageously utilized in combination with one or more other therapies (e.g., one or more other prophylactic or therapeutic agents), preferably therapies useful in the prevention, treatment and/or management of the (same or another) disease or disorder. When one or more other therapies (e.g., prophylactic or therapeutic agents) are used, they can be administered separately, in any appropriate form and by any suitable route. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, other single variable domains, synthetic or natural inorganic molecules, mimetic agents, and synthetic or natural organic molecules. Any therapy (e.g., prophylactic or therapeutic agents) which is known to be useful, or which has been used or is currently being used for the prevention, treatment and/or management of one or more symptoms associated with a specific disease or disorder, can be used in combination with the formulations of the present invention in accordance with the invention described herein.

A formulation of the invention may be administered to a mammal, preferably a human, concurrently with one or more other therapies (e.g., one or more other prophylactic or therapeutic agents). The term "concurrently" is not limited to the administration of prophylactic or therapeutic agents/therapies at exactly the same time, but rather it is meant that the formulation of the invention and the other agent/therapy are administered to a mammal in a sequence and within a time interval such that the polypeptide contained in the formulation can act together with the other agent/therapy to provide an increased benefit than if they were administered otherwise. For example, the formulation of the invention and the one or more other prophylactic or therapeutic agents may be administered at the same time or sequentially in any order at different points in time; however, if not administered at the same time, they should be administered sufficiently close in time so as to provide the desired therapeutic or prophylactic effect.

When used in combination with other therapies (e.g., prophylactic and/or therapeutic agents), the formulations of the invention and the other therapy can act additively or synergistically. The invention contemplates administration of a formulation of the invention in combination with other therapies (e.g., prophylactic or therapeutic agents) by the same or different routes of administration, e.g., oral and parenteral.

Various delivery systems are known and can be used to administer the formulation of the present invention. Methods of administering formulations of the present invention include, but are not limited to, parenteral administration (e.g., intradermal, intramuscular, intraperitoneal, intravenous and, preferably subcutaneous), epidural administration, topical administration, and mucosal administration (e.g., intranasal and oral routes). In a specific embodiment, liquid formulations of the present invention are administered subcutaneously.

The invention will now be further described by means of the following non-limiting preferred aspects and examples:
Preferred Aspects
1. A formulation, such as a pharmaceutical formulation, comprising an aqueous carrier, a buffer and a polypeptide comprising one or more single variable domains, said formulation being formulated for administration to a human subject, wherein the polypeptide has a concentration of at least 30 mg/ml.
2. The formulation of aspect 1, wherein the polypeptide has a concentration of at least 60 mg/ml.
3. The formulation of aspect 2, wherein the polypeptide has a concentration of at least 80 mg/ml.
4. The formulation of aspect 3, wherein the polypeptide has a concentration of at least 100 mg/ml.
5. The formulation of any of aspects 1 to 4, wherein the polypeptide comprises three single variable domains.
6. The formulation of any of aspects 1 to 5, wherein the polypeptide comprises at least one single variable domain that is directed against and/or specifically binds RANKL.
7. The formulation of any of aspects 1 to 6, wherein the polypeptide comprises at least one single variable domain that is directed against and/or specifically binds HSA.
8. The formulation of any of aspects 1 to 7, wherein the polypeptide comprises two single variable domains directed against and/or specifically binding RANKL and one single variable domain directed against and/or specifically binding HSA.
9. The formulation of any of aspects 1 to 8, wherein the polypeptide is SEQ ID NO: 1.
10. The formulation of any of aspects 1 to 9, wherein the polypeptide has a biphasic melting temperature profile wherein one Tm1 is at least 60° C. or more, preferably at least 61° C. or more, more preferably at least 62° C. or more and Tm2 is at least 65° C. or more, preferably at least 66° C. or more, more preferably at least 67° C. or more, as measured by the thermal shift assay and/or differential scanning calorimetry (DSC).
11. The formulation of any of aspects 1 to 10, wherein the polypeptide is stable after multiple (up to 10) freeze/thaw cycles, said stability as determined by SE-HPLC, IEX-HPLC, RP-HPLC, Biacore analysis and/or potency assay.
12. The formulation of any of aspects 1 to 11, wherein the polypeptide is stable during storage at a temperature of −20±5° C. up to at least 3 months (preferably at least 6 months, at least 9 months, at least 1 year, 1.5 year or even 2 years or more), said stability as determined by SE-HPLC and/or RP-HPLC.
13. The formulation of any of aspects 1 to 12, wherein the polypeptide is stable during storage at a temperature of 2-8° C. up to at least 3 months (preferably at least 6 months, at least 9 months, at least 11 months, at least 1 year, 1.5 year or even 2 years or more), said stability as determined by SE-HPLC, RP-HPLC and/or potency assay.
14. The formulation of any of aspects 1 to 13, wherein the polypeptide is stable during storage at a temperature of 25±5° C. up to at least 6 weeks, said stability as determined by SE-HPLC, RP-HPLC, potency assay and/or SDS-PAGE.
15. The formulation of any of aspects 1 to 14, wherein the polypeptide is stable during storage at a temperature of 37±5° C. up to at least 2 weeks, said stability as determined by SE-HPLC, RP-HPLC, potency assay and/or SDS-PAGE.
16. The formulation of aspect 15, wherein the polypeptide is stable during storage at a temperature of 37±5° C. up to at least 4 weeks.
17. The formulation of aspect 16, wherein the polypeptide is stable during storage at a temperature of 37±5° C. up to at least 6 weeks.
18. The formulation of aspect 17, wherein the polypeptide is stable during storage at a temperature of 37±5° C. up to at least 8 weeks.
19. The formulation of any of aspects 11 to 18, wherein less than 10% of the polypeptides forms pyroglutamate at the N-terminal glutamic acid during storage, the % of pyroglutamate as measured by RP-HPLC.
20. The formulation of any of aspects 15 to 19, wherein less than 10% of the polypeptides forms pyroglutamate at the N-terminal glutamic acid during storage at a temperature of 37±5° C., the % of pyroglutamate as measured by RP-HPLC.
21. The formulation of any of aspects 11 to 18, wherein less than 25% of the polypeptides forms dimers during storage, the % of dimers as measured by SE-HPLC.
22. The formulation of aspect 21, wherein less than 15% of the polypeptides forms dimers.
23. The formulation of any of aspects 15 to 18 and/or 21 to 22, wherein less than 25% of the polypeptides forms dimers during storage at a temperature of 37±5° C., the % of dimers as measured by SE-HPLC.
24. The formulation of aspect 23, wherein less than 15% of the polypeptides forms dimers.
25. The formulation of any of aspects 1 to 24, that does not show the formation of aggregates as measured by analytical ultracentrifugation and/or dynamic light scattering.
26. The formulation of any of aspects 1 to 25, wherein at least 80% of the polypeptides retain their binding activity to RANKL after storage compared to the binding activity prior to storage, said binding activity as measured by ELISA and/or Biacore.
27. The formulation of aspect 26, wherein at least 90% of the polypeptides retain their binding activity to RANKL after storage compared to the binding activity prior to storage, said binding activity as measured by ELBA and/or Biacore.
28. The formulation of any of aspects 1 to 25, wherein at least 80% of the polypeptides retain their binding activity to HSA after storage compared to the binding activity prior to storage, said binding activity as measured by ELISA and/or Biacore.
29. The formulation of aspect 28, wherein at least 90% of the polypeptides retain their binding activity to HSA after storage compared to the binding activity prior to storage, said binding activity as measured by ELISA and/or Biacore.
30. The formulation of any of aspects 1 to 29, wherein at least 80% of the polypeptides retain their binding activity to RANKL and HSA after storage compared to the binding activity prior to storage, said binding activity as measured by ELISA and/or Biacore.
31. The formulation of aspect 30, wherein at least 90% of the polypeptides retains their binding activity to RANKL and HSA after storage compared to the binding activity prior to storage, said binding activity as measured by ELISA and/or Biacore.
32. The formulation of any of aspects 15 to 18 and/or 26 to 31, wherein at least 80% of the polypeptides retain their binding activity to RANKL after storage at 37±5° C. compared to the binding activity prior to storage, said binding activity as measured by ELISA and/or Biacore.
33. The formulation of aspect 32, wherein at least 90% of the polypeptides retain their binding activity to RANKL after storage at 37±5° C. compared to the binding activity prior to storage, said binding activity as measured by ELISA and/or Biacore.
34. The formulation of any of aspects 15 to 18 and/or 26 to 33, wherein at least 80% of the polypeptides retain their binding activity to HSA after storage at 37±5° C. compared to the binding activity prior to storage, said binding activity as measured by ELISA and/or Biacore.
35. The formulation of aspect 34, wherein at least 90% of the polypeptides retain their binding activity to HSA after storage at 37±5° C. compared to the binding activity prior to storage, said binding activity as measured by ELISA and/or Biacore.
36. The formulation of any of aspects 15 to 18 and/or 26 to 35, wherein at least 80% of the polypeptides retain their binding activity to RANKL and HSA after storage at 37±5° C. compared to the binding activity prior to storage, said binding activity as measured by ELISA and/or Biacore.
37. The formulation of aspect 36, wherein at least 90% of the polypeptides retain their binding activity to RANKL and HSA after storage at 37±5° C. compared to the binding activity prior to storage, said binding activity as measured by ELISA and/or Biacore.
38. The formulation of any of aspects 1 to 37, wherein the single variable domain is stable under mechanical stress.
39. The formulation of aspect 38, wherein the mechanical stress is selected from shaking during 10 s to 1 min, pushing through a needle (25 G, preferably 26 G, more preferably 27 G, even more preferably 28 G, most preferably 29 G or more) with a syringe, rotation for two days at 10 rpm, and stirring for 1 hour at room temperature and 2 days at 4° C. at least 10 rpm (such as 50 rpm, 100 rpm or more).
40. The formulation of any of aspects 1 to 39, which has a pH in the range of 5.5-7.0.
41. The formulation of aspect 40, wherein the buffer is a phosphate buffer or an acetate buffer,
42. The formulation of aspect 41, wherein the buffer is at a concentration of 10 mM.
43. The formulation of aspect 40 to 42, which has a pH of about 5.5.
44. The formulation of aspect 43, wherein the buffer is an acetate buffer at a concentration of 10 mM.
45. The formulation of aspect 40 to 42, which has a pH of about 7.0.
46. The formulation of aspect 45, wherein the buffer is a phosphate buffer at a concentration of 10 mM.
47. The formulation according to any of aspects 19 or 20, which has a pH of 5.5 or 7.0.
48. The formulation according to aspect 47, wherein the buffer is acetate or phosphate at a concentration of 10 mM.
49. The formulation according to any of aspects 21 to 24, which has a pH of 5.5 or 7.0.
50. The formulation according to aspect 49, wherein the buffer is acetate or phosphate at a concentration of 10 mM.
51. The formulation according to any of aspects 26 to 37, which has a pH of 5.5 or 7.0.
52. The formulation according to aspect 51, wherein the buffer is acetate or phosphate at a concentration of 10 mM.
53. The formulation of any of aspects 1 to 52, wherein the aqueous carrier is distilled water.
54. The formulation of any of aspects 1 to 53, wherein the aqueous carrier is MilliQ grade water or Water for injection (WFI).
55. The formulation according to any of aspects 1 to 54, which is isotonic or slightly hypotonic.
56. The formulation according to aspect 55, which has an osmolality of 290±60 mOsm/kg.
57. The formulation of any of aspects 55 or 56, further comprising a salt.
58. The formulation of aspect 57, wherein the salt is NaCl.

59. The formulation of any of aspects 57 or 58, wherein the salt is at a concentration of about 100 mM.
60. The formulation of any of aspects 57 or 58, wherein the salt is at a concentration of 115 mM.
61. The formulation of any of aspects 1 to 60, further comprising a surfactant.
62. The formulation of any of aspects 38 or 39, comprising a surfactant.
63. The formulation of any of aspects 61 or 62, wherein the surfactant is at a concentration up to 0.01%.
64. The formulation of any of aspects 61 to 63, wherein the surfactant is Tween20 or Tween80.
65. The formulation of any of aspects 61 to 64, wherein the surfactant is Tween80 at a concentration of 0.01% (v:v).
66. The formulation of any of aspects 1 to 65, wherein
    less than 10% of the polypeptide forms pyroglutamate at the N-terminal glutamic acid during storage at a temperature of 37±5° C. up to at least 2 weeks, the % of pyroglutamate as measured by RP-HPLC;
    less than 25% of the polypeptide forms dimers during storage at a temperature of 37±5° C. up to at least 2 weeks, the % of dimers as measured by SE-HPLC;
    at least 80% of the polypeptide retains its binding activity to at least one of its targets after storage at 37±5° C. up to 6 weeks compared to the binding activity prior to storage, said binding activity as measured by ELISA and/or Biacore; and/or
    the polypeptide is stable during mechanical stress.
67. The formulation of any of aspects 1 to 66, comprising:
    65 mg/ml of SEQ ID NO: 1;
    10 mM disodium hydrogen phosphate (Na$_2$H$_2$PO$_4$);
    115 mM Sodium chloride (NaCl);
    0.01% Tween80 (v:v).
68. A method for the preparation of a formulation of any of aspects 1 to 67, comprising the step of concentrating the polypeptide with SEQ ID NO: 1 and exchanging it with a buffer.
69. A formulation which is produced by lyophilizing the formulation according to any of aspects 1 to 67.
70. Method for the preparation of the lyophilized formulation of claim 69, comprising the step of freeze-drying a solution of any of aspects 1 to 67.
71. A formulation which is produced by spray drying the formulation according to any of aspects 1 to 67.
72. Method for the preparation of the spray dried formulation of claim 71, comprising the step of spray drying a solution of any of aspects 1 to 67.
73. A sealed container containing a formulation according to any of aspects 1 to 67, 69 and/or 71.
74. A pharmaceutical unit dosage form suitable for parenteral administration to a human, comprising a formulation according to any of aspects 1 to 67, 69 and/or 71 in a suitable container.
75. The pharmaceutical unit dosage form of claim 74, which is suitable for subcutaneous administration.
76. A kit comprising one or more of the sealed containers according to aspect 73 and/or pharmaceutical unit dosage forms according to any of aspects 74 or 75, and instructions for use of the formulation.
77. The formulation, container, pharmaceutical unit dosage or kit according to any of the preceding aspects for use in therapy.
78. Method for prevention and/or treatment of one or more bone diseases and/or disorders, comprising administering to a subject in need thereof a formulation according to any of aspects 1 to 67, 69 or 71.
79. Method of claim 78 wherein the bone disease and/or disorder is osteoporosis, cancer-related bone diseases, and/or bone loss associated with autoimmunity and/or viral infection.

EXAMPLES

Example 1: Materials and Methods Used in the Study 1.1 Single Variable Domains

RANKL008a (SEQ ID NO: 1; EVQLVES-GGGLVQPGGSLRLSCAASGFTFSSYPMGWFRQAPG-KGREFV SSITGSGGSTYYADSVKGRFTISRDNAKNT-LYLQMNSLRPEDTAWYCAAYIRPDTYLSRDYRKYD-YWGQGTLVTVS SGGGGSGGGSEVQLVES-GGGLVQPGNSLRLSCAASGFTFSSFGMSWVRQAPG-KGLEWVSSISGSGSDTLYADSV KGRFTISRDNAKT-TLYLQMNSLRPEDTAVYYCTIGGSLSRSSQGTLVTVS-SGGGGSGGGSEVQLVESGGGLVQPGG SLRLSCAAS-GFTFSSYPMGWFRQAPGKGREFVSSITGSGGSTYY-ADSVKGRFTISRDNAKNTLYLQMNSLRPEDTA VYY-CAAYIRPDTYLSRDYRKYDYWGQGTLVTVSS) has been described as SEQ ID NO: 759 in WO 2008/142164. RANKL008a is a trivalent bispecific Nanobody consisting of three humanized variable domains of a heavy-chain llama antibody, of which two identical subunits are specific for binding to RANKL while the remaining subunit binds to HSA. The subunits are fused head-to-tail with a G/S linker in the following format: RANKL13H5-9GS-Alb8-9GS-RANKL13H5.

RANKL008a was expressed in *Pichia pastoris* and purified on SP Sepharose as a capturing step and a Q filter as a polishing step or on SP Sepharose as a capturing step and Capto MMC as a polishing step (GE Healthcare Life Sciences). Concentration of the Nanobody and buffer switch to PBS, 10 mM phosphate+100 mM NaCl or 10 mM phosphate+5% mannitol was done via UF/DF (Sartorius Hydrosart Sartocon Slice 200, 10 kDa). A final filtration was carried out at 0.22 μm. An overview of the different batches is given in Table 1.

Either batch P#270308nr1 or unstressed samples of the different batches given in Table 1 were used as reference material throughout the different experiments.

1.2 Other Critical Reagents

Reagents used in the study are given in Table 2.

1.3 Equipment for Measurements and Analytical Testing

HPLC experiments were carried out on an Agilent 1200 series instrument from Agilent Technologies (Palo Alto, USA). The columns used were:

RP-HPLC: Zorbax 300SB-C3 5-micron, 4.6×150 mm (Agilent, Cat. No. 883995-909, serial no. USKD001612)

SE-HPLC: TSKgel G2000SW$_{XL}$ (Tosoh Bioscience, Japan); guard column TSKgel (SWXL no. SWXN0676)

IEX-HPLC: Dionex ProPac WCX-10 column; guard column ProPac WCX 10G

Quantity measurements of RANKL008a were done with a Uvikon 943 Spectrophotometer (Kontron instruments) at A278 nm.

Particle size distribution was measured on a PAMAS SVSS-C particle counter (PArtikelMess-und AnalyseSysteme GMBH).

For measurement of HSA and RANKL binding activity Biacore 3000 (GE Healthcare) was used. Potency was determined using two ELISA-based assays.

For lyophilization use was made of the freeze dryer Epsilon 2-4 from Martin Christ (Osterode am Harz, Germany).

Osmolality measurement was done with an osmometer Model 3320 from Advanced instruments.

Analytical ultracentrifugation and dynamic light scattering were carried out by Nanolytics GmbH (Potsdam, Germany) as described further.

1.4 Inhibition ELISA for RANKL Potency Measurement

RANKL008a interacts with human (soluble) receptor activator of nuclear factor-kappaB ligand (RANKL) and blocks the interaction of this ligand with its human receptor activator of nuclear factor-kappaB (RANK), thereby preventing signalization through this receptor. The potency of RANKL008a was measured by an ELISA-based inhibition assay that allowed to assess the relative potency of the RANKL binding moieties of an unknown batch of RANKL008a relative to a reference batch.

For the reference, the control and the test samples, different dilutions of Nanobodies were prepared. These dilutions were pre-incubated with a constant amount of 5 ng/ml soluble RANKL and a constant amount of 200 ng/ml RANK-Fc. Subsequently, this mixture was transferred to a microtiter plate coated with a non-blocking anti-Fc Nanobody PMP02. After washing, residual bound RANKL was detected with biotinylated anti-human RANKL antibody, followed by hors radish peroxidase (HRP)-labeled streptavidin detection.

The relative potency of the test samples compared to the reference samples was analysed by use of PLA 2.0 Software (Stegmann Systems).

1.5 ELISA for HSA Binding

The relative potency of the HSA binding moiety in RANKL008a was measured by an ELISA. In short, HSA was coated onto a plastic multiwell Maxisorp ELISA plate by adsorption. After blocking excess binding sites on the plates with Superblock T20, a dilution series of references, control and test samples was applied on the plate. Duplicates were measured and each replicate was assessed on a different plate. Bound Nanobody was subsequently detected using a bivalent anti-Nanobody Nanobody, directly conjugated to horseradish peroxidase (HRP). In the presence of $H_2O_2$, this peroxidase catalyzes a chemical reaction with the substrate Tetramethylbenzidine (TMB) which results in the formation of a color. The reaction was stopped by adding 1N HCl. The optical density of the color formed was measured at a wavelength of 450 nm in a plate spectrophotometer.

The relative potency of the test samples compared to the reference samples was analysed by use of PLA 2.0 Software (Stegmann Systems).

1.6 Purity Assay of RANKL008a by Size Exclusion High Performance Liquid Chromatography (SE-HPLC)

The SE-HPLC assay consisted of a pre-packed silica gel TSKgel G2000SW$_{XL}$ column equipped with a guard column pre-column filter, a mobile phase consisting of KCl, NaCl and phosphate buffer pH7.2 (D-PBS) and UV detection at A280 nm. The relative amount of specific protein impurity was expressed as area %, and was calculated by dividing the peak area corresponding to the specific protein or protein impurity by the total integrated area.

1.7 Purity Assay of RANKL008a by Reversed Phase High Performance Liquid Chromatography (RP-HPLC)

In the RP-HPLC assay a Zorbax 300SB-C3 column (Agilent Technologies, Palo Alto, US) was used. The relative amount of a specific protein impurity was determined by measuring the light absorbance of the components eluting from the RP-HPLC column. The identity of the RANKL008a Nanobody was confirmed by comparing the relative elution time from the RP-HPLC column. The relative amount of a specific protein impurity, expressed as area %, was calculated by dividing the peak area corresponding to the impurity by the total integrated area.

1.8 Purity Assay of RANKL008a by Ion Exchange High Performance Liquid Chromatography (IEX-HPLC)

The IEX-HPLC assay combined the use of a pre-packed Dionex ProPac WCX-10 weak cation exchange column, a mobile phase consisting of citrate buffer pH5.5 and UV detection at A280 nm. After loading the protein(s) on the column, bound materials were eluted by a sodium chloride gradient. The relative amount of the specific protein, variant, or impurities expressed as area %, was calculated by dividing the peak area corresponding to the specific protein or to any protein impurity by the total area of all integrated peaks.

1.9 Affinity Measurement on Biacore

A chip was first immobilized with RANKL or HSA (amine coupling using the Biacore amine coupling kit). After a preconditioning step of 5 injections of RANKL008a, all samples were diluted to 2.5 nM in triplicate and analyzed on the chip. Quality control of the chips using the reference sample was included in the experiment to detect any loss of activity or decrease in response (deterioration of the chip). Slopes were determined using the general fit method and the linear fit model (BIAevaluation software). To determine the initial binding rate (IBR), the slope between 5 s and 30 s was selected. The values of these slopes were transferred in excel and the percentage activity compared to the RANKL008a reference was determined.

1.10 Measurement of Particle Size Distribution (Subvisible Particle Counting)

The different samples were analyzed using a particle size distribution analyzer, the PAMAS Small Volume Syringe System (SVSS)-C instrument. It uses the principle of light obscuration to detect sub-visible particles in the size range 1 μm-200 μm.

The measurements on the PAMAS SVSS-C particle counter were performed as follows: 100 μl sample was diluted 1/10 in 1 ml MilliQ water and 10 consecutive measurements were performed in all 16 channels (diameter set 1, 2, 3, 4, 5, 6, 7, 8, 9, 10, 15, 25, 50, 100, 150 and 200 μm). For calculation of the average value, the first 2 measurements were excluded and the dilution factor was taken into account. The results are given as cumulative data (total particle counts>x μm) or differential data (total particle counts between diameter x and y μm). Only the cumulative data are presented.

Example 2: Effect of One Freeze/Thaw Cycle (F/T) on the Stability of the Nanobody RANKL008a P#110708 was formulated in different buffers (see overview in Table 3) at either 63 mg/ml, a concentration that is compatible with SC delivery at 3 mg/kg, or 30 mg/ml. The formulation was subjected to one freeze (−20° C.) and thaw (room temperature) cycle and analyzed by SE-HPLC and RP-HPLC.

There was no apparent effect of one F/T cycle on the stability of RANKL008a in the different buffer conditions: one F/T did not cause any difference in retention time, peak height, peak area and peak shape in the SE-HPLC and RP-HPLC chromatograms (data not shown).

Example 3: Stability Study at 5° C.

RANKL008a was formulated in the same buffers as summarized in Table 3 and several aliquots were stored at 5°

C. to compare the long-term stability of the different liquid formulations. Samples that were incubated for 2 weeks and 3 months (12 weeks) were analyzed by SE-HPLC, RP-HPLC and potency assay. Data after 3 months incubation are shown in FIG. 1 (SE-HPLC), FIG. 2 (RP-HPLC) and Table 4 (potency).

There were no significant changes in potency, SE-HPLC and RP-HPLC profiles between the reference material and all samples stored at 5° C. In the SE-HPLC analysis, a very small decrease of the main peak surface area was observed in all buffers, while there was a minor increase in the prepeak and postpeak 2 surface areas. The surface area of the prepeak in the RP-HPLC profile was slightly increased in all buffers except in acetate, while there was a small increase in the post-peak corresponding to the pyroglutamate variant in all buffer conditions.

Example 4: Stability Study at 37° C.

RANKL008a was formulated in the same buffers as summarized in Table 3 and several aliquots were stored at 37° C. for an accelerated stress study. Samples were analyzed at regular time intervals by SE-HPLC, RP-HPLC, IEX-HPLC, potency assays, Biacore and SDS-PAGE.

4.1 SE-HPLC Analysis

After 2 weeks of storage, analysis of the samples by SE-HPLC showed a shoulder appearing on the main peak in all buffer conditions. The shoulder was most apparent in PBS buffer and at higher protein concentration. After 3 weeks of incubation, the shoulder got resolved from the main peak into a prepeak. The prepeak most likely represented a dimeric/oligomeric form of RANKL008a that was being formed upon storage at elevated temperature. FIG. 3 shows an overlay with the gel filtration marker. The high molecular weight variant eluted at an approximate MW of 44 kDa. Taking the 'sticky' nature of native RANKL008a into account, these could correspond to a dimeric form of RANKL008a. This hypothesis was corroborated by the AUC data presented in Example 8.

The peak surface area of the prepeak increased with storage time (FIG. 4) and was accompanied by a concomitant decrease in surface area of the main peak. The formation of dimers was concentration-dependent and the surface area of the prepeak was higher for RANKL008a at 63 mg/ml compared to 30 mg/ml in all buffers (FIG. 5). The kinetics of dimer formation appeared to be similar in all buffer conditions. However, the propensity to form dimers was higher in PBS buffer than in phosphate or acetate buffer (FIGS. 6 and 7). Tween80 has no apparent effect in preventing dimerization (FIG. 7).

There were two minor postpeaks being formed, most likely representing RANKL008a degradation products. The surface area of these postpeaks increased somewhat over time and remained the lowest in acetate buffer, pH 5.5. Overall, there was only minimal degradation of RANKL008a after 8 weeks at 37° C. (see also SDS-PAGE analysis in section 4.6).

4.2 RP-HPLC Analysis

The RP-HPLC profiles at timepoint 0 weeks included a main peak and two postpeaks. The main peak had a shoulder which eluted before the main material and of which the surface area remained unchanged upon storage. Postpeak 1 corresponded to a pyroglutarnate-containing variant of RANKL008a and comprised about 2-3% of the total integrated area in unstressed RANKL008a. Postpeak 2 represented the variant with one missing disulphide bridge in the RANKL binding building block as further described in PCT application PCT/EP2010/055916 filed by Ablynx N.V. on 30 Apr. 2010 entitled "Method for the production of variable domains". This postpeak had completely disappeared in all buffer conditions after 2 weeks at 37° C. (oxidation proceeds faster at elevated temperature).

The peak surface area of the pyroglutamate peak increased with storage time (FIG. 8) and was accompanied by a concomitant decrease in surface area of the main peak. The total area remained unchanged.

After 2 weeks of storage, a prepeak of the main peak was formed in all buffer conditions. The identity of this variant is unknown at the moment. The surface area increased with prolonged incubation time, was highest in PBS and phosphate buffer and appeared to be concentration-independent.

There was also a time-dependent increase of some minor peaks at Rt 8-9 min, which represented the degradation fragments. The surface area of these peaks was the lowest in acetate buffer, pH 5.5 (cfr. SE-HPLC data in 4.1).

In general, the relative amounts of the prepeak and pyroglutamate peak was the lowest in acetate buffer, pH 5.5.

4.3 IEX-HPLC Analysis

The IEX-HPLC profile of RANKL008a in the different buffers at 0 weeks consisted of a single peak containing a shoulder (elution after the main peak). In some IEX-HPLC runs, the shoulder was not well-resolved and was then visible as tailing of the main peak. The surface area of the shoulder did not seem to vary upon storage at 37° C. (data not shown).

After 2 weeks of storage, a large postpeak appeared in all buffer conditions. The surface area of the postpeak was highest in PBS buffer and increased with storage time and protein concentration. The postpeak in IEX-HPLC might represent dimeric RANKL008a that is likely to be charged differently than the monomeric protein.

After 8 weeks storage, a small postpeak appears in the different buffers. The surface area was lowest in acetate buffer and somewhat higher at higher protein concentration. The identity of this peak is yet unknown (FIG. 9).

4.4 Potency Assays

The potency of the different samples was determined in the HSA binding assay and RANKL inhibition assay as described in Example 1. The relative potencies compared to the reference batch (P#270308) obtained for the different samples are shown in Table 5.

In all samples, a gradual decrease in HSA binding activity was observed in function of storage time. The activity loss was more pronounced at higher protein concentration. After 8 weeks of storage, there appeared to be a small loss of RANKL binding activity in the samples formulated at 63 mg/ml.

4.5 Biacore Assay

To confirm the results obtained by the potency assay, the functionality of the RANKL008a stability samples was determined using an IBR/functionality assay on HSA and RANKL (Biacore). The activity was calculated in relation to the unstressed samples (0 weeks). All analyses were performed in triplicate and the results are shown in FIG. 10.

The Biacore experiment confirmed the potency assay results with respect to the loss of HSA binding activity. The drop in activity appeared to be higher in PBS buffer and in the samples at the highest concentration (63 mg/ml). The RANKL potency on the other hand remained unchanged according to the Biacore data.

4.6 SDS-PAGE Analysis

Five μg of the different stressed samples at 63 mg/ml and of the samples subjected to one freeze thaw cycle were loaded on SDS-PAGE in reducing and non-reducing conditions. The gels were stained with the Krypton IR protein stain for 1 hour and scanned with the Odyssey Infrared Imaging system (Li-Cor Inc.).

The results are summarized in FIG. 11. In general, the amount of degradation products increased with incubation time and was the lowest in acetate buffer<phosphate<PBS. Potential dimers are visible in the gels from the samples in PBS.

Example 5: Stability Study at −20° C.

Samples formulated in the different buffers (Table 3) were stored for 3 months at −20° C. and analyzed by SE-HPLC and RP-HPLC. The HPLC profiles were identical between the reference batch and material stored for 3 months. There were no new peaks being formed (data not shown).

Example 6: Freeze-Thaw (F/T) Stability Study

A freeze-thaw stability study was performed to determine the effect of repetitive freeze and thawing on the recovery, physical stability and chemical stability of RANKL008a. Two different studies were performed using batch P#040908nr1, which was formulated at 60 mg/ml in four different buffers (FIG. 12). In the first study, the different samples were subjected to 5 F/T cycles at −20° C., followed by another 5 F/T cycles (10 F/T cycles in total). In the second study, the material was subjected to 2 cycles at −80° C. followed by 1 cycle at −20° C. and then 5 cycles at −20° C. (6 F/T cycles at −20° C. in total).

One freeze-thaw (F/T) cycle is defined by freezing the sample for 1 hour in a freezer (−20° C.) or ultrafreezer (−80° C.) followed by thawing at room temperature for 30 minutes. The stressed samples were compared with reference material (stored at 4° C.) using SE-HPLC, RP-HPLC, IEX-HPLC, Biacore and the potency assay (Table 6).

Subjecting RANKL008a to up to 10 F/T cycles had no visible effect on its stability and potency. There were no apparent differences in stability and potency between the different buffers.

The SE-HPLC, RP-HPLC- and IEX-HPLC profiles were identical between the reference batches and material subjected to multiple freeze-thaw cycles. There was no decrease in the total surface area and no new peaks were being formed (data not shown).

Analysis by Biacore and the potency assay indicated no loss of activity after repetitive freezing and thawing.

Example 7: Lyophilization of the Different Nanobody Formulations

Lyophilization experiments were performed with RANKL008a at ~60 mg/ml in 6 different formulations (Table 7). 300 µl of each sample were freeze/dried using the program as shown in Table 8. Uniform, solid lyophilization cakes were obtained in all buffer conditions. Lyophilized RANKL008a was reconstituted in 300 µl Milli® water and analyzed by A278 SE-HPLC (FIGS. 13 and 14), RP-HPLC (FIG. 15), Biacore (FIG. 16) and potency assay (Table 9). A 100 µl aliquot was also put on storage at 37° C. for stability testing of the lyophilized product and was analyzed by SE-HPLC and RP-HPLC at 2 and 4 weeks time points.

After 2 weeks of storage at 37° C., SE-HPLC analysis showed a prepeak which most likely represented dimeric RANKL008a. This peak was most apparent in acetate buffer (FIG. 13) and increased over time in all buffer conditions (FIG. 14). An additional prepeak was present at a retention time of 34.4 minutes, which could correspond to higher molecular weight aggregates of RANKL008a. These aggregates have not yet been observed in stressed samples of RANKL008a that were not lyophilized. There seems to be no apparent effect of Tween80 in preventing aggregate formation (FIG. 14).

There were two minor postpeaks being formed, most likely representing RANKL008a degradation products. The surface area of these postpeaks increased somewhat over time and remained the lowest in acetate buffer, pH 5.5. Overall, there was only minimal degradation of RANKL008a after 4 weeks at 37° C.

In the RP-HPLC analysis the peak surface area of the pyroglutamate peak increased with storage time and was higher in phosphate buffer than in acetate buffer (FIG. 15). After 2 weeks of storage at 37° C., a small prepeak of the main peak was formed in all buffer conditions (data not shown). The identity of this variant is unknown at the moment. At 4 weeks of storage at 37° C., there was a slight increase of some minor peaks at Rt 8-9 min, which represent degradation fragments.

The different samples of lyophilized RANKL008a dissolved very efficiently in the reconstitution buffer (MQ). No significant differences in protein concentration were observed after reconstitution. This was also confirmed by the recoveries in RP-HPLC and SE-HPLC. There were no or only very small modifications or changes in potency (FIG. 16, Table 9), even in the absence of Tween80.

There were no visible particles or precipitation in the reconstituted products. Storage at elevated temperature induced the formation of dimers, which was also observed for non-lyophilized RANKL008a, as well as very small amounts of higher molecular weight aggregates.

Example 8: Measurements of Aggregates Using Hydrodynamic and Thermodynamic Methods The presence of potential aggregates in unstressed and stressed (37° C.) samples at >60 mg/ml and in the absence of Tween80 was verified by analytical ultracentrifugation (AUC) and dynamic light scattering (MS). More specifically, the goal of the study was to detect the presence of any reversible self-association and/or irreversible aggregates.

The study was carried out by Nanolytics GmbH (Potsdam, Germany). The aggregation behavior of RANKL008a samples was examined by sedimentation velocity measurements. Initial experiments were performed with the undiluted samples (63 mg/ml). Due to the observed non-ideality at this concentration samples were diluted to 1 mg/ml in each formulation buffer that was compared (PBS, versus phosphate versus acetate buffer) and re-examined. At these concentrations the influence of non-ideality was small enough to be neglected. Experiments were performed at 20° C. in an Analytical Ultracentrifuge XL-I from Beckman coulter using the interference optics (high concentration samples; measurement at 675 nm) or the absorption optics (A278 nm) for the lower concentration samples. 400 µl samples were brought into centerpieces of (1.2 or 1.5) mm optical pathlengths and spun at 50 krpm. For the calculation of the Sedimentation Coefficient Distribution the frictional ratio was treated as a fitting parameter. Quantification of the aggregates was performed on the diluted samples. Additional sedimentation equilibrium experiments revealed that the dimer is irreversible.

Dynamic Light Scattering was performed with a red-light laser (641 nm) at scattering angles of 30° and 90° or with a blue-light laser (402 nm) at a scattering angle of 20°. The partial specific volume of the protein was assumed to be 0.72 ml/g.

The main conclusions of the study were that an unstressed purified preparation of RANKL008a is pure, monomeric and that the solution is monodisperse:

Sedimentation velocity experiments showed that no significant amounts of aggregates or degradation products were present in the sample. These results were in agreement with SE-HPLC data described in Example 4;

No evidence of reversible self-association and no indication for the presence of irreversible aggregates was found in sedimentation equilibrium experiments;

Dynamic light scattering demonstrated that the sample showed a monomodal distribution of the particle size. No signal was detected at particle radii >10 nm, confirming the absence of irreversible aggregates.

A follow-up study with temperature stressed samples (0, 2, 4 and 8 weeks at 37° C.) at 60 mg/ml in PBS, 10 mM Acetate, pH 5.5+50 mM NaCl and 10 mM Phosphate, pH 7+50 mM NaCl was performed.

Firstly, results from the sedimentation velocity experiments showed that all samples were qualitatively similar. At the first time point, a single component was observed, sedimenting at ca. 2.3 S. For the samples taken at 2, 4 and 8 weeks, a small signal at ca. 4.3 S was detectable. Based on hydrodynamic considerations, the second component at ca. 4.5 S could correspond to a dimer of the component at 2.9 S. Detailed results obtained with interference optics and the diluted samples are presented in Table 10. The differences in relative concentration of the RANKL008a dimer in the different buffers correlated well with the SE-HPLC data described in Example 4.

Secondly, Dynamic Light Scattering detected a single dominant peak between 3-5 nm for all samples. This signal will comprise both the monomer of RANKL008a and the putative dimer, due to the limited resolution of the method. For samples in acetate buffer and PBS, no other signals from protein were observed. In the case of phosphate buffer, two other components at ca. 40 nm and ca. 300 nm could be observed in the samples stressed for 2 and 4 weeks and were judged relevant. Due to their small weight concentration, these components will not be detectable by sedimentation velocity. For all samples examined, a second peak was observed at various particle diameters between 50-200 nm for the 8 weeks time point. This indicated a progression of the aggregation towards larger particles.

Example 9: Osmolality Measurement of the Different Formulations

Osmolality measurements were performed on the different formulations used in the stability studies:

P#040908nr1 in 10 mM phosphate buffer pH 7.0/50 mM NaCl at 61 mg/ml: 121 mOsm/kg
P#040908nr1 in 10 mM phosphate buffer pH 7.0/50 mM NaCl at 89 mg/ml: 123 mOsm/kg
P#040908nr1 in 10 mM acetate buffer pH 5.5/50 mM NaCl at 59 mg/ml: 116 mOsm/kg
P#040908nr1 in 10 mM acetate buffer pH 5.5/50 mM NaCl at 91 mg/ml: 123 mOsm/kg Because the tested formulations were hypotonic, additional amounts of the tonicity agent NaCl were added to determine at which concentration an isotonic solution is obtained:

P#040908nr1 in 10 mM phosphate buffer pH 7.0/129 mM NaCl at 61 mg/ml: 351 mOsm/kg
P#040908nr1 in 10 mM acetate buffer pH 5.5/100 mM NaCl at 59 mg/ml: 272 mOsm/kg These results indicate that the final formulation buffer should contain at least 100 mM NaCl as tonicity agent.

Finally the osmolality of a phosphate buffer with Tween80 was determined:

NBJ0539-08-08 SB2 in 10 mM phosphate pH 7.0/0.01% Tween80 (v:v)/100 mM NaCl at 65.2 mg/ml: 227 mOsm/kg
NBJ0539-08-08 SB2 in 10 mM phosphate pH 7.0/0.01% Tween80 (v:v)/114.4 mM NaCl at 65.2 mg/ml: 244 mOsm/kg

Example 10: Lyophilization of the Nanobody Formulation

Lyophilization of RANKL008a P#151008nr1 (84.3 mg/ml) formulated in 10 mM phosphate/100 mM NaCl and P#151008nr2 (70 mg/ml) in 10 mM phosphate/5% mannitol was performed. Mannitol is a widely used bulking agent for lyophilization. After reconstitution in sterile water of lyophilized RANKL008a, the RP-HPLC and SE-HPLC profiles were compared before and after lyophilization. In addition, the stability of reconstituted, lyophilized RANKL008a was verified in an accelerated stress study at 37° C. Storage samples were analyzed via SE-HPLC and RP-HPLC after 1, 3 and 5 weeks of storage. The 5 weeks samples were also analyzed using IEX-HPLC and Biacore.

300 µl of each sample was freeze/dried using the program of Table 8. Lyophilization resulted in uniform (solid) lyophilization cakes for both samples. The sample in phosphate/100 mM NaCl readily dissolved in reconstitution buffer (300 µl MilliQ H$_2$O). The sample in phosphate/5% mannitol only dissolved after 3-4 hours at 4° C. There were no apparent differences in the SE-HPLC and RP-HPLC profiles before and after lyophilization in either 10 mM phosphate+100 mM NaCl or 10 mM phosphate+5% mannitol (data not shown). No significant differences in protein concentration were observed after reconstitution of lyophilized RANKL008a. This was also confirmed by the identical recoveries in RP-HPLC and SE-HPLC. There were no visible particles, precipitation or any detectable modifications in the reconstituted products.

An aliquot was also put on storage at 37° C. for stability testing of the lyophilized product. SE-HPLC and RP-HPLC data of the 5 week time point are shown in FIGS. 17-18 and FIG. 19 respectively. After 1 week of storage, a prepeak was being formed on SE-HPLC which represented the dimeric form of RANKL008a (FIG. 17). This peak increased over time and was most apparent in the formulation without 5% mannitol (FIG. 18).

In RP-HPLC, the peak surface area of the pyroglutamate peak increased with storage time. In addition, a small prepeak in front of the main peak was being formed in both buffers. The identity of this variant is unknown at the moment (FIG. 19). During storage, there was also an increase of some minor peaks at Rt 8-9 min, which most likely correspond to degradation fragments of RANKL008a.

In IEX-HPLC, in addition to the main peak observed of the control samples, two new peaks were present in the stability samples (FIG. 20). The surface area of both post-peaks was lower in the mannitol-containing samples.

The RANKL and HSA binding of RANKL008a in the stability samples stored for 5 weeks was compared with the activity of the unstressed reference batch using Biacore analysis. The relative potencies are given in Table 11 and are expressed as % activity compared to reference batch P#040908nr1. As observed for all other RANKL008a stability samples, the HSA binding activity had significantly decreased after prolonged storage at 37° C. Also, the addition of mannitol was beneficial for maintaining a higher HSA binding activity under stressed conditions.

RANKL008a lyophilized in 10 mM Phosphate, pH 7+100 mM NaCl dissolved more readily in the reconstitution buffer (MilliQ) than RANKL008a in 10 mM Phosphate, pH 7+5% mannitol. There were no visible particles or precipitation in the reconstituted products.

Storage at elevated temperature induced the formation of dimers, which was also observed for non-lyophilized RANKL008a. No higher molecular weight aggregates could be detected in the storage samples. The degree of dimer formation was significantly reduced in the presence of mannitol.

Example 11: Melting Point Determination of the Nanobodies in the Different Buffers Melting point determination of RANKL008a (P#110708nr1) was carried out by the thermal shift assay as to i) determine the pH at which the highest Tm values are observed (pH 4.0 to 5.5: 10 mM acetate-buffer and pH 6.0 to 7.5: 10 mM phosphate-buffer) for both 0.1 and 0.2 mg/ml protein concentrations, and ii) assess the influence of adding NaCl to the formulation/assay mixture. The final assay mixtures contain 10× Sypro Orange (fluorescent dye). A typical example of a TSA fluorescence curve is given in FIG. 21 and the overall results of the assay are provided in Table 12.

In general, the melting temperatures of RANKL008a were situated around 64° C. for the Alb8 subunit and 71° C. for the R13h5 moiety. In the absence of NaCl the most suitable pH was 6.5 to 7.0, whereas this was lowered by one pH unit in the presence of salt. As to distinguish between the two applied buffers, phosphate buffer with 150 mM NaCl would be most suitable for formulation at pH values between 6.0 and 7.0, whereas at pH 5.5 acetate buffer with an equal amount of NaCl should be preferred.

Example 12: Stability of the Nanobodies During Mechanical Stress

Mechanical stress experiments were performed on RANKL008a batch NBJ0539-08-08 SB2 (62.2 mg/ml). The RANKL008a sample was diluted or undiluted with and without 0.01% Tween80 (v:v). The samples were shaken, stirred, rotated and pushed through a needle with a syringe (the syringe used can be any commercially available syringe, such as e.g. a 1 ml, 2 ml, 3 ml, 4 ml, 5 ml, 10 ml, 20 ml, 30 ml, 40 ml up to 50 ml syringe) as follows:
  Diluted to 5 mg/ml or undiluted and shaken (10 s-1 min);
  Pushed through a syringe (3 ml) with needle 25 G (undiluted) (10×);
  Rotated (10 rpm) 2 days at room temperature (undiluted);
  Stirred 1 hour at room temperature and for 2 days at 5° C. (diluted to 5 mg/ml).
The different samples were compared visually for any differences in appearance.

Strong shaking for a short time (10 s) caused strong foaming of the samples without Tween80. Even the diluted sample got very opaque (FIG. 22). Sample nr 1 got very opaque even after shaking the vial for only 10 s.

The undiluted RANKL008a sample with and without 0.01% Tween80 (v:v) was pushed 10 times through a needle (25 G) with a 3 ml syringe. The visual observations are described in Table 13. The sample without Tween80 got more opaque, there was also formation of foam and tiny air bubbles were visible when tapping the vial.

The undiluted RANKL008a sample with or without 0.01% Tween80 (1 ml in 1.5 ml Eppendorf tube) was rotated for 2 days at 10 rpm. Both samples stayed clear.

The diluted (to 5 mg/ml) RANKL008a sample with or without 0.01% Tween80 (v:v) was stirred for 1 hour at room temperature and further for 2 days at 5° C. The visual observations are described in Table 14. After stirring 1 hour at room temperature, the sample without Tween80 was slightly opaque while the sample with Tween80 stayed clear. After 2 days stirring at 5° C., both sample were opaque but the opacity in the sample without Tween80 was higher (Table 14).

With the addition of 0.01% Tween80 (v:v), the RANKL008a sample was less or not opaque after mechanical stress and there was less foam formation. This indicates that the sample is less susceptible to denaturation if Tween80 is added.

Example 13: Syringeability of the Different Nanobody Formulations

The effect of using different diluents—i.e. saline solution, phosphate buffer without Tween80 or phosphate buffer with Tween80—on content, visual appearance and functionality of RANKL008a (NBJ0607-02) at low concentration (0.28 mg/mL) was determined after passage through syringe. RANKL008a was diluted in different diluents followed by passage or 24 h storage in syringes (FIG. 23). The FIG. 23 contains the legends to the different samples generated during this experiment where the following codes are applied:
  S25/0: storage at 25° C. for 0 minute
  S25/24: storage at 25° C. for 24 h
  −TW: buffer minus Tween 80
  +TW: buffer+Tween 80
  PLACEBO refers to the following buffer: 10 mM $Na_2HPO_4$ pH 7.0+115 mM NaCl
  TUB: sample stored in a polystyrene tube
Visual inspection and content determination of RANKL008a after dilution in different diluents and passage/storage in syringes is given in Table 15. Data on turbidity measurement are given in FIG. 24. Relative HSA and RANKL functionality of RANKL008a after dilution in different diluents and passage/storage in syringes is shown in FIG. 25.

Passage through a syringe slightly increased turbidity when using 10 mM $Na_2HPO_4$, 115 mM NaCl (pH 7.0). Dilution in saline solution caused a drop in RANKL/HSA binding activity of 18-34.0%. A similar effect was observed using 10 mM $Na_2HPO_4$, 115 mM NaCl (pH 7.0) without Tween80, i.e. a drop of 15-27%. In contrast, dilution in 10 mM $Na_2HPO_4$, 115 mM NaCl (pH 7.0) with Tween80 did not appear to have a dramatic effect confirming the beneficial role of Tween80 in the buffer.

Example 14: Stability of Nanobody Formulation after Single or Stepwise Dilutions RANKL008a (NBJ0607-02) was diluted in different diluents in a single step or by means of a serial dilution (FIG. 26) in order to determine whether the latter method reduces sample turbidity.

Visual inspection of RANKL008A after single and stepwise dilution in different diluents is shown in Table 16, increased sample turbidity and aggregate formation was observed when using 0.9% NaCl as diluent.

Both single step and stepwise dilution of RANKL008a to 0.28 mg/mL using 0.9% NaCl resulted in sample turbidity and precipitation. At 16 mg/ml the first aggregates were observed. In contrast, single step or stepwise dilution in 10 mM $Na_2HPO_4$, 115 mM NaCl, 0.01% Tween80 (v:v), (pH 7.0) did not result in the formation of precipitates.

Example 15: Stability of Nanobody Formulations During Syringe Passage with Different Needle Size The effect of syringe passage on visual appearance of the RANKL008a using different needle sizes and needle size combinations was evaluated. RANKL008a was diluted in an Eppendorf tube (TUB) in 10 mM $Na_2HPO_4$, 115 mM NaCl, 0.01% Tween80 (v:v), (pH 7.0) to a final concentration of 0.28 mg/ml followed by single passage through a 1 ml BD syringe equipped with different needles (i.e. Terumo 18 G, 23 G, 27 G and 30 G) (FIG. 27). In this Figure and Table 17 the following codes apply:
+TW: buffer+Tween 80
PLACEBO refers to the following buffer: 10 mM $Na_2HPO_4$ pH 7.0+115 mM NaCl
TUB: sample stored in a polystyrene tube
18 G/18 G: sample drawn up with a 18 G needle and expelled through a 18 G needle
18 G/27 G: drawn up with a 18 G needle and expelled through a 27 G needle
All other coding is similar to the two examples given above.

Turbidity was determined by visual inspection and by measurement of the absorption at wavelengths of 320 nm, 340 nm, 350 nm and/or 500 nm, and determining the ratio of the obtained value over the absorption at A278 nm (mostly 320/278 and 350/278). A ratio of >0.05 was considered significant. Visual inspection, content and turbidity of RANKL008a before (TUB) and after passage through syringes with different needle size is shown in Table 17.

In a further experiment, RANKL008a was subjected to single passage through a 1 ml syringe equipped with different needle sizes (i.e. 27 G and 29 G) both undiluted (65 mg/mL) and diluted in 10 mM $Na_2HPO_4$, 115 mM NaCl, 0.01% Tween80 (v:v), (pH 7.0) to a final concentration of 0.28 mg/ml (FIG. 28). In order to reduce protein use, 29 G and 30 G needles were not included for testing undiluted DP. Visual inspection, content and turbidity of RANKL008a before (TUB) and after passage through syringes with different needle size is shown in Table 18. In Table 18 and FIG. 28 the following codes are used:
+TW: buffer+Tween 80
PLACEBO refers to the following buffer: 10 mM $Na_2HPO_4$ pH 7.0+115 mM NaCl
TUB: sample stored in a polystyrene tube
27 G/27 G: sample drawn up with a 27 G needle and expelled through a 27 G needle
29 G/29 G: drawn up with a 29 G needle and expelled through a 29 G needle
T: Terumo needle, B Becton Dickinson needle
0028 refers to concentration at 0.28 mg/mL, 6500 to about 65 mg/mL Different combinations of needle sizes did not have a significant effect on RANKL008a recovery or sample turbidity both at low (0.28 mg/mL) and high (62.8 mg/mL) concentration (up to gauge sizes 29 and 27 respectively). In both experiments turbidity values were low (<0.05).

Example 16: Solubility of RANKL008a at Increased Concentrations

A study was performed with RANKL008a batch B2#170608nr1 at a concentration of 156 mg/ml and formulated in the following buffers:
PBS
PBS+0.02% Tween80 (v:v)
PBS+0.05% Tween80 (v:v)
PBS+0.1% Tween80 (v:v)

The samples were stored at 25° C. and analyses were performed at regular time intervals. An overview is given in Table 19. The different samples were also subjected to one freeze/thaw cycle (−20° C.).

16.1 Analysis by SE-HPLC

SE-HPLC profiles of the different samples are shown in FIGS. 29, 30 and 31. Prolonged storage at 25° C. resulted in the formation of a prepeak and postpeak (FIG. 30). The peak area of the pre peak increased significantly over time. The prepeak most likely represented a dimeric form of RANKL008a.

FIG. 31 shows an overlay of the SE-HPLC profiles of the gel filtration marker and the sample stored for 6 weeks at 25° C. in PBS. The theoretical MW of RANKL008a is 40.994 Da, yet the calculated MW based on the elution time is only 26 kDa. This is most likely due to interaction of RANKL008a with the matrix of the column ('stickiness' of the RANKL008a molecule). The prepeak observed in the stressed samples had approximately the same elution time as the 44 kDa component of the gel filtration maker and could thus correspond to a dimeric form of RANKL008a.

The postpeak probably corresponded to degradation products (due to remaining proteolytic activity in sample). The relative area (%) of this peak in the 3 and 6 weeks samples was identical, implying that degradation was not progressing over time.

One freeze/thaw cycle had no effect on the SE-HPLC profile of RANKL008a (data not shown).

16.2 Analysis by RP-HPLC

RP-HPLC profiles of the different samples are shown in FIGS. 32 and 33.

The RP-HPLC profiles of RANKL008a at 156 mg/ml and the reference batch RANKL008aPic P#270308 (15% postpeak) were comparable. There were also no differences in the RP-HPLC profiles of the samples without or with Tween80.

There were only minor differences between the RP-HPLC profiles upon increased incubation time, i.e. a slight increase of the pyroglutamate peak and a small decrease of the postpeak, i.e. the variant with one missing S—S bridge. Both peaks were already present in the unstressed samples, with a peak surface area of 2.6% and 17.1%, respectively.

One freeze/thaw cycle had no effect on the RP-HPLC profile of RANKL008a.

16.3 Determination of Subvisible Particles (PAMAS)

The different samples were analyzed using the PAMAS instrument. The total number of particles >10 μm and >25 μm are shown in FIG. 34. There seems to be a time-dependent increase in the particle counts and particle size.

16.4 Determination of Potency

The relative potencies compared to the reference batch (B11#140208) obtained for the different samples are shown in Table 20.

The ultrafiltration process and the concentration to >150 mg/ml appeared not to have an effect on the activity of RANKL008a. Freeze/thawing did not seem to affect the relative potency of both the HSA binding moiety and the RANKL binding moieties.

Example 17: Stability of the Formulations for 11 Months at −20° C. and at 5° C.

RANKL008a P#110708, 67 mg/ml, 1% postpeak (unpaired cysteines) was dialyzed into 3 different buffers (D-PBS, phosphate and acetate containing 50 mM NaCl) with or without 0.02% Tween80 (Table 3). The samples were put on storage (5 and −20° C.) at 2 different concentrations (30 and 63 mg/ml) for 11 months.

The SE-HPLC profiles are shown in FIG. 35. Storage at −20° C. or 5° C. for 11 months did not have a significant effect on the physical stability of the RANKL008a Nanobody. Samples formulated in PBS and phosphate at 5° C. showed a minor pre-peak, most likely corresponding to the RANKL008a dimer, which was not seen in the phosphate 63 mg/ml with Tween80 en phosphate 30 mg/ml with Tween80 samples. Adding Tween80 to the phosphate buffer (63 mg/ml) appeared to prevent formation of the dimer. At 53-58 min an additional peak was detected in 30 mg/ml samples which originated from the different formulation buffers. Compared to the measurement after storage during 3 months, storage during 11 months at 5° C. resulted in a slight increase in post peak, suggesting protein degradation. This effect was most obvious in samples formulated in PBS.

The RP-HPLC profiles are shown in FIG. 36. Storage at −20° C. and 5° C. for 11 months did not have a significant effect on the chemical stability of the RANKL008a Nanobody. Compared to the measurement after storage during 3 months:

a slight increase in pre-peak was observed in samples at 5° C. and most pronounced in PBS buffer;
the pyroglutamate peak was relatively stable in all buffers (surface areas and area % was comparable);
an increase in post peak was detected in some conditions.

Based on the results obtained for content, SE-HPLC and RP-HPLC analysis, it can be concluded that the RANKL008a Nanobody remains stable at 5° C. and −20° C. for 11 months. Small changes were observed in some of the 5° C. samples (i.e. pre/post peak in SE-HPLC and post peak in RP-HPLC analysis).

Example 18: Melting Point Determination by Differential Scanning Calorimetry (DSC)

DSC experiments were performed in a MicroCal Automated Capillary VP-DSC instrument. Sample concentration during the assay was set at 1 mg/mL in D-PBS. To check for melting temperature ($T_m$), samples were scanned at 200° C./h using a temperature range of 20° C. to 100° C., except otherwise noted.

The DSC unfolding curve for RANKL008a (FIG. 37) indicates that there are two unfolding domains in RANKL008a, one having a $T_m$ of 64.1° C. (Alb8) and the other a $T_m$ of 70.4° C. (R13h5). RANKL008a is composed of two R13h5 domains linked to each other by one Alb8 unit, a feature that can be deduced to a certain degree from the thermogram, i.e. the Alb8 surface corresponds to approximately half of the R13h5 portion.

The DSC analysis of Alb8 (FIG. 38) revealed a $T_m$ value of 62.8° C. After the scan the sample was reheated, however, peak repeatability was not observed. Most likely, the rate constant of the complete irreversible step is high at high temperatures and therefore renders repeatability of the experiment impossible.

The melting temperature of 62.8° C. for Alb8 as measured by differential scanning calorimetry was confirmed to a certain degree in the RANKL008a analysis. R13h5, in the RANKL008a format, was found to have a Tm of 70.4° C. These results corroborate those obtained by the fluorescence-based thermal shift assay (see Example 11).

Example 19: Long-Term Stability Study at −20° C. and +5° C.

RANKL008a batch NBJ0607-04, formulated in 10 mM $Na_2HPO_4$, 115 mM NaCl, 0.01% Tween80 (v:v) (pH7.0) at 62.5 mg/mL, was stored for 12 months at −20° C. and +5° C. Samples were analysed after 1, 2, 3, 6, 9 and 12 months of storage by visual inspection (appearance), A278 (content), SE-HPLC, IEX-HPLC, RP-HPLC and potency assays (RANKL inhibition assay and HSA binding assay). The results are summarized in Table 21 and Table 22 for storage at −20° C. and +5° C., respectively.

There were no significant changes in appearance, content, potency, and HPLC profiles between the control sample (timepoint 0 months) and all test samples indicating that RANKL008a is stable for at least 12 months at −20° C. or 5° C. Small differences with the control sample were observed in the sample stored for 12 months at +5° C. The percentage main peak observed during IEX-HPLC analysis was lower compared to the control sample suggesting a somewhat lower purity. During SE-HPLC analysis, a minor postpeak appeared which could indicate the presence of degradation fragments.

Tables

TABLE 1

Overview of the RANKL008a batches used in the stability studies described in the Example section.

| Batch no. | Buffer | Concentration | Remark | Applied stress condition |
|---|---|---|---|---|
| P#270308nr1 | D-PBS | 3.3 mg/ml | 15% Postpeak* in RP-HPLC | Reference material |
| B2#170608nr1 | D-PBS | 156 mg/ml | 15% Postpeak* in RP-HPLC | Storage at 25° C. |
| P#110708nr1 | D-PBS | 67 mg/ml | 1.3% Postpeak* in RP-HPLC | Storage at −20° C., 5° C. and 37° C. |
| P#040908nr1 | D-PBS | 143 mg/ml | No Postpeak in RP-HPLC | F/T study Lyophilization experiments Storage at 37° C. (for AUC and DLS analysis only) Reference material |

TABLE 1-continued

Overview of the RANKL008a batches used in the stability studies described in the Example section.

| Batch no. | Buffer | Concentration | Remark | Applied stress condition |
|---|---|---|---|---|
| P#151008nr1 | 10 mM phosphate + 100 mM NaCl | 84.3 mg/ml | No Postpeak in RP-HPLC | Lyophilization experiments |
| P#151008nr2 | 10 mM phosphate + 5% mannitol | 70 mg/ml | No Postpeak in RP-HPLC | Lyophilization experiments |
| NBJ0539-08-08 SB2 | 10 mM phosphate + 100 mM NaCl | 65.2 mg/ml | No Postpeak in RP-HPLC | Osmolality determination |
| NBJ0607-02 | 10 mM $Na_2HPO_4$, 115 mM NaCl, 0.01% Tween80 (v:v) (pH7.0) | 62.8 mg/ml | No Postpeak in RP-HPLC | Syringeability experiment Dilution experiment |

*Corresponding to the variant having an unpaired cysteine bridge in one of the RANKL13H5 building blocks (which elutes approximately 2 minutes later than the main peak in RP-HPLC analysis) as described in PCT application PCT/EP2010/055916 filed by Ablynx N. V. entitled "Method for the production of variable domains."

TABLE 2

Reagents used in the Examples section.

| Reagent | Provider | Cat No. |
|---|---|---|
| ACN, HPLC grade | Biosolve | Cat. No. 012007 |
| TFA | Biosolve | Cat. No. 20234131 |
| Isopropanol, HPLC grade | Biosolve | Cat. No. 162606 |
| D-PBS | Gibco | Cat. No. 14190-094 |
| Citric acid monohydrate | Merck | Cat. No. 1.00244.0500 |
| NaCl | Merck | Cat. No. 1.06404.1000 |
| Gel filtration standard | Bio-Rad | Cat. No. 151-1901 |
| Tween80 | Merck | Cat. No. 8.17061.1000 |
| Sodium acetate | Merck | Cat. No. 1.06268.1000 |
| Sodium dihydrogenphosphate | Merck | Cat. No. 1.06345.1000 |
| Disodium hydrogenphosphate | Merck | Cat. No. 1.06576.1000 |
| RANKL | Peprotech | Cat. No. 310-01 |
| HSA | Sigma | Cat. No. A3782 |
| Krypton IR protein stain | Pierce | Cat. No. 53071 |
| MW marker (Precision Plus Protein Dual Color Standard) | Bio-Rad | Cat. No. 161-0374 |
| D-Mannitol | Fluka | Cat. No. 17311 |
| 0.9% NaCl | B. Braun | Cat. No. 394496 (lot 7372A231) |
| 0.22 µm filter Millex ®-GV | Millipore | Cat. No. SLGV004SL |
| 1 mL syringe (29G × ½") | Becton-Dickinson | Cat. No. 328411 |
| 1 mL syringe (29G × ½") | Terumo | Cat. No. 14.BS-N1H2913 |
| 1 mL syringe | Becton-Dickinson | Cat. No. 300013 |
| 2 mL syringe, Luer Lock | Becton-Dickinson | Cat. No. 300185 |
| Microlance needle (30G × ½") | Becton-Dickinson | Cat. No. 304000 |
| 2 mL syringe, Luer Lock | Terumo | Cat. No. SS02LZ1 |
| Neolus ® needle (18G × 2") | Terumo | Cat. No. NN-1850R |
| Neolus ® needle (23G × 1¼") | Terumo | Cat. No. NN-2332R |
| Neolus ® needle (27G × ¾") | Terumo | Cat. No. NN-2719R |
| SurGuard ® needle (30G × ½") | Terumo | Cat. No. SG2-3013 |
| Borosilicate glass 1-2 mL | Thüringer Pharmaglass | Cat. No. 2R |
| Safe-Lock 2 mL | Eppendorf | Cat. No. 0030 121.597 |
| Polystyrene Tube 15 mL | Greiner Bio-One | Cat. No. 186161 |

TABLE 3

Overview of the different formulations of RANKL008a used in stability testing.

| Concentration RANKL008a | Buffer | Additional [NaCl] | % Tween80 (v:v) |
|---|---|---|---|
| 63 mg/ml | PBS | 0 | 0 |
| 63 mg/ml | PBS | 0 | 0.02 |
| 30 mg/ml | PBS | 0 | 0 |
| 30 mg/ml | PBS | 0 | 0.02 |
| 63 mg/ml | 10 mM $NaH_2PO_4 \cdot 2H_2O$, pH 7 | 50 mM | 0 |
| 63 mg/ml | 10 mM $NaH_2PO_4 \cdot 2H_2O$, pH 7 | 50 mM | 0.02 |
| 30 mg/ml | 10 mM $NaH_2PO_4 \cdot 2H_2O$, pH 7 | 50 mM | 0 |
| 30 mg/ml | 10 mM $NaH_2PO_4 \cdot 2H_2O$, pH 7 | 50 mM | 0.02 |
| 63 mg/ml | 10 mM Na-acetate, pH 5.5 | 50 mM | 0 |
| 63 mg/ml | 10 mM Na-acetate, pH 5.5 | 50 mM | 0.02 |
| 30 mg/ml | 10 mM Na-acetate, pH 5.5 | 50 mM | 0 |
| 30 mg/ml | 10 mM Na-acetate, pH 5.5 | 50 mM | 0.02 |

TABLE 4

Relative potency with regard to reference standard) of RANKL008a after storage at 5° C. as described in Example 3.

| | 63 mg/ml | | | | 30 mg/ml | | | |
|---|---|---|---|---|---|---|---|---|
| | 0 weeks | | 2 weeks | | 0 weeks | | 2 weeks | |
| Sample | HSA | RANKL | HSA | RANKL | HSA | RANKL | HSA | RANKL |
| PBS | 0.842 | 1.149 | 0.714 | 1.111 | 0.825 | 1.096; 1.096 | 0.96; 0.857 | 1.169 |
| PBS + Tw80 | 0.901 | 1.114 | 0.701 | 1.063 | 0.796 | 1.049; 1.136 | 1.017; 0.933 | 1.173 |

TABLE 4-continued

Relative potency with regard to reference standard) of RANKL008a after storage at 5° C. as described in Example 3.

| | 63 mg/ml | | | | 30 mg/ml | | | |
|---|---|---|---|---|---|---|---|---|
| | 0 weeks | | 2 weeks | | 0 weeks | | 2 weeks | |
| Sample | HSA | RANKL | HSA | RANKL | HSA | RANKL | HSA | RANKL |
| Phosphate | 0.794 | 0.862 | 0.65 | 0.981 | 0.836 | 1.073; 0.99 | 0.859; 0.934 | 0.996 |
| Phosphate + Tw80 | 0.837 | 1.035 | 0.661 | 0.979 | 0.899 | 1.19; 1.085 | 0.917; 1.011 | 1.057 |
| Acetate | 0.818 | 1.057 | 0.643 | 0.992 | 0.836 | 1.202; 1.096 | 0.882; 0.935 | 1.079 |
| Acetate + Tw80 | 0.904 | 1.046 | 0.71 | 1.048 | 0.899 | 1.155; 1.100 | 1.002; 1.034 | 1.084 |

TABLE 5

The relative potencies (with regard to reference standard) of HSA and RANKL binding moieties of temperature stressed samples of RANKL008a.

| | 0 w | 1 w | 2 w | 3 w | 4 w | 6 w | 8 w | 0 w | 1 w | 2 w | 3 w | 4 w | 6 w | 8 w |
|---|---|---|---|---|---|---|---|---|---|---|---|---|---|---|
| | 63 mg/ml HSA | | | | | | | 30 mg/ml HSA | | | | | | |
| PBS | 0.842 | 0.968 | 0.889 | 0.742 | 0.756 | 0.693 | 0.62 | 0.825 | 0.954 | 0.96 | 0.961 | 0.999 | 0.784 | 0.772 |
| PBS + Tw80 | 0.901 | 1.049 | 0.882 | 0.765 | 0.859 | 0.673 | 0.629 | 0.796 | 0.99 | 0.984 | 0.954 | 1.097 | 0.821 | 0.822 |
| Phosphate | 0.794 | 0.891 | 0.774 | 0.754 | 0.724 | 0.611 | 0.583 | 0.836 | 0.908 | 0.837 | 0.837 | 0.943 | 0.722 | 0.688 |
| Phosphate + Tw80 | 0.837 | 0.893 | 0.919 | 0.747 | 0.739 | 0.629 | 0.581 | 0.899 | 0.984 | 0.916 | 0.948 | 0.936 | 0.79 | 0.719 |
| Acetate | 0.818 | 0.89 | 0.791 | 0.758 | 0.72 | 0.645 | 0.631 | 0.836 | 0.949 | 0.905 | 0.869 | 0.992 | 0.778 | 0.798 |
| Acetate + Tw80 | 0.904 | 1.107 | 0.884 | 0.773 | 0.822 | 0.714 | 0.598 | 0.899 | 1.053 | 1.013 | 0.941 | 1.051 | 0.773 | 0.81 |
| | 63 mg/ml RANKL | | | | | | | 30 mg/ml RANKL | | | | | | |
| PBS | 1.149 | 1.112 | 1.06 | 0.939 | 1.008 | 1.064 | 0.687 | 1.096 1.096 | 0.96 1.042 | 1.015 | 0.976 | 1.17 | 0.941 | 0.887 |
| PBS + Tw80 | 1.114 | 1.069 | 1.063 | 0.979 | 1.11 | 0.924 | 0.9 | 1.049 1.136 | 1.009 1.151 | 1.09 | 1.115 | 1.216 | 0.836 | 0.898 |
| Phosphate | 0.862 | 1.012 | 0.95 | 0.917 | 0.99 | 0.848 | 0.799 | 1.073 0.99 | 0.763 0.971 | 0.852 | 0.931 | 1.035 | 0.786 | 0.805 |
| Phosphate + Tw80 | 1.035 | 1.012 | 0.968 | 0.853 | 0.927 | 0.897 | 0.755 | 1.19 1.085 | 0.913 0.916 | 0.98 | 0.932 | 0.946 | 0.779 | 0.762 |
| Acetate | 1.057 | 0.985 | 1.023 | 0.948 | 1.049 | 1.011 | 0.801 | 1.202 1.096 | 0.857 0.935 | 0.969 | 1.021 | 1.158 | 0.967 | 0.936 |
| Acetate + Tw80 | 1.046 | 1.148 | 1.078 | 0.863 | 1.123 | 0.875 | 0.897 | 1.155 1.100 | 0.814 0.954 | 0.867 | 1.039 | 1.14 | 0.803 | 0.829 |

TABLE 6

The relative potencies (with regard to reference standard) of HSA and RANKL binding moieties of samples of RANKL008a after various freeze-thaw cycles.

| | | Relative potency | |
|---|---|---|---|
| | Number of | | |
| Buffer | Freeze/Thaw cycles | RANKL | HSA |
| Phosphate | 10 FT −20° C. | 0.967 | 0.918 |
| Phosphate | 2 FT −80° C. + 6 FT −20° C. | 0.866 | 0.900 |
| Phosphate + 0.02% Tween80 (v:v) | 10 FT −20° C. | 0.845 | 0.817 |
| Phosphate + 0.02% Tween80 (v:v) | 2 FT −80° C. + 6 FT −20° C. | 0.804 | 0.810 |
| Acetate | 10 FT −20° C. | 0.921 | 0.890 |
| Acetate | 2 FT −80° C. + 6 FT −20° C. | 0.827 | 0.893 |
| Acetate + 0.02% Tween80 (v:v) | 10 FT −20° C. | 0.736 | 1.023 |
| Acetate + 0.02% Tween80 (v:v) | 2 FT −80° C. + 6 FT −20° C. | 0.908 | 1.123 |

TABLE 7

Samples used in the lyophilization experiment.

| RANKL008a | | % Tween80 (v:v) | |
|---|---|---|---|
| 10 mM Phosphate, pH 7 + 50 mM NaCl 56 mg/ml | 0 | 0.05 | 0.1 |
| 10 mM Acetate, pH 5.5 + 50 mM NaCl 60 mg/ml | 0 | 0.05 | 0.1 |

TABLE 8

Program used for the lyophilisation of the RANKL008a samples.

| | Phase | | | | | | |
|---|---|---|---|---|---|---|---|
| | 1 | 2 | 3 | 4 | 5 | 6 | 7 |
| Section | Load | Freeze | | | Main dry | | |
| Section time | / | 1 h 30 | 1 h | 4 h | 10 h | 3 h | 3 h |
| Shelf temp. (° C.) | 20 | −45 | −40 | −35 | −20 | −10 | 0 |
| Vacuum (mbar) | / | / | / | 1.030 | 1.030 | 1.030 | 3.380 |
| Safety pressure | off | off | off | off | 1.650 | 6.110 | 6.110 |
| dT freeze/drying | off | off | off | off | off | off | off |

TABLE 9

The relative potencies (with regard to reference standard) of HSA and RANKL binding moieties of samples of RANKL008a after lyophilisation.

| | RANKL | HSA |
|---|---|---|
| Phosphate | 0.642; 1.127; 0.762* | 0.626 |
| Phosphate + 0.05% Tween80 (v:v) | 1.190 | 0.970 |
| Phosphate + 0.1% Tween80 (v:v) | 1.030 | 0.925 |
| Acetate | 1.191 | 0.978 |
| Acetate + 0.05% Tween80 (v:v) | 0.761 | 0.672 |
| Acetate + 0.1% Tween80 (v:v) | 0.970 | 0.981 |

*Three measurements were done.

TABLE 10

Summary of the results from sedimentation velocity experiments using stressed and unstressed samples of RANKL008a at high protein concentration.

| Sample | | $s^*_1$ [S] | $c_1$ [rel. conc.] | $s^*_2$ [S] | $c_2$ [rel. conc.] |
|---|---|---|---|---|---|
| PBS | 0 w | 2.91 | 0.99 | NA | NA |
| | 2 w | 2.90 | 0.82 | 4.17 | 0.18 |
| | 4 w | 2.96 | 0.73 | 4.51 | 0.27 |
| | 8 w | 2.90 | 0.60 | 4.23 | 0.32 |
| 10 mM Phosphate + 50 mM NaCl | 0 w | 2.92 | 0.99 | NA | NA |
| | 2 w | 2.98 | 0.86 | 4.39 | 0.14 |
| | 4 w | 2.98 | 0.76 | 4.37 | 0.23 |
| | 8 w | 2.90 | 0.69 | 4.25 | 0.26 |
| 10 mM Acetate + 50 mM NaCl | 0 w | 2.94 | 0.96 | 4.71 | 0.04 |
| | 2 w | 2.96 | 0.87 | 4.47 | 0.12 |
| | 4 w | 2.97 | 0.79 | 4.38 | 0.21 |
| | 8 w | 2.94 | 0.70 | 4.27 | 0.27 |

$S^*_1$: sedimentation coefficient for monomer RANKL008a $S^*_2$: sedimentation coefficient for dimer RANKL008a

[S]: Svedberg unit

TABLE 11

Relative potencies (with regard to reference standard) of the HSA and RANKL binding moieties of reconstituted, lyophilized RANKL008a after 5 weeks at 37° C.

| | Relative potency | |
|---|---|---|
| Buffer | RANKL | HSA |
| Phosphate + 100 mM NaCl, pH | 93.7 | 67.0 |
| Phosphate + 5% Mannitol, pH | 90.3 | 80.9 |

TABLE 12

Melting temperature (° C.) for RANKL008a in acetate (pH 4.0 to 5.5) and in phosphate (pH 6.0 to 8.0).

| | | pH 4 | pH 4.5 | pH 5 | pH 5.5 | pH 6 | pH 6.5 | pH 7 | pH 7.5 | pH 8 |
|---|---|---|---|---|---|---|---|---|---|---|
| Buffer without NaCl | Tm1 | — | — | — | — | — | 64.43 | 64.50 | 64.37 | — |
| | Tm2 | 70.01 | 70.74 | 71.53 | 70.34 | 70.67 | 71.80 | 71.20 | 70.47 | 69.01 |
| Buffer + 50 mM NaCl | Tm1 | 61.05 | — | — | — | — | — | — | — | — |
| | Tm2 | 67.62 | 69.67 | 70.47 | 70.67 | 72.26 | 71.66 | 71.07 | 70.2 | |
| Buffer + 150 mM NaCl | Tm1 | 58.01 | — | 64.51 | 64.37 | 64.17 | 64.44 | 64.77 | — | |
| | Tm2 | 65.96 | 69.61 | 70.60 | 71.13 | 70.99 | 70.79 | 70.26 | 69.81 | |
| Buffer + 500 mM NaCl | Tm1 | 54.81 | 59.26 | 61.36 | 62.43 | 63.10 | 63.04 | 63.10 | 62.77 | |
| | Tm2 | 63.11 | 65.43 | 68.68 | 69.61 | 69.87 | 69.87 | 69.74 | 69.14 | |

TABLE 13

Visual observation after Syringe/needle experiment described in Example 12.

| Without Tween80 | 0.01% Tween80 (v:v) |
|---|---|
| More opaque | Opaque |
| Air bubbles | / |
| Foam | / |

TABLE 14

Visual observation after stirring experiment described in Example 12.

| | Without Tween80 | 0.01% Tween80 (v:v) |
|---|---|---|
| 1 hour at room temperature | Slightly opaque | Clear |
| 2 days at 5° C. | More opaque | Opaque |

TABLE 15

Visual inspection and content determination of RANKL008a after dilution in different diluents and passage/storage in syringes.

| sample | visual inspection | content (mg/mL) |
|---|---|---|
| 0028 SALINE TUB | small precipitates | 0.265 (0.261-0.270) |
| 0028 SALINE SYR S25/0 | small precipitates | 0.263 (0.261-0.265) |
| 0028 SALINE SYR S25/24 | small precipitates | 0.259 (0.256-0.262) |
| 0028 PLACEBO − TW TUB | small precipitates | 0.272 (0.271-0.273) |
| 0028 PLACEBO − TW SYR S25/0 | small precipitates | 0.268 (0.267-0.269) |
| 0028 PLACEBO − TW SYR S25/24 | small precipitates | 0.268 (0.259-0.276) |
| 0028 PLACEBO + TW TUB | clear | 0.281 (0.281-0.281) |
| 0028 PLACEBO + TW SYR S25/0 | slightly turbid | 0.280 (0.278-0.282) |
| 0028 PLACEBO + TW SYR S25/24 | slightly turbid | 0.279 (0.277-0.281) |

TABLE 16

Visual inspection of RANKL008a after single and stepwise dilution in different diluents.

| sample | dilution | visual inspection | estimated concentration (mg/mL) |
|---|---|---|---|
| 6500 DP ref | 1/1 | clear | 65.0 |
| 6500 DP PL + TW 1STEP 256X | 1/256 | clear | 0.25 |
| 6500 DP PL + TW 1STEP 2X | 1/2 | clear | 32.5 |
| 6500 DP PL + TW 2STEP 4X | 1/4 | clear | 16.3 |
| 6500 DP PL + TW 3STEP 8X | 1/8 | clear | 8.13 |
| 6500 DP PL + TW 4STEP 16X | 1/16 | clear | 4.06 |
| 6500 DP PL + TW 5STEP 32X | 1/32 | clear | 2.03 |
| 6500 DP PL + TW 6STEP 64X | 1/64 | clear | 1.02 |
| 6500 DP PL + TW 7STEP 128X | 1/128 | clear | 0.51 |
| 6500 DP PL + TW 8STEP 256X | 1/256 | clear | 0.25 |
| 6500 DP SAL 1STEP 256X | 1/256 | heavy precipitation + turbid | 0.25 |
| 6500 DP SAL 1STEP 2X | 1/2 | clear | 32.5 |
| 6500 DP SAL 2STEP 4X | 1/4 | precipitation | 16.3 |
| 6500 DP SAL 3STEP 8X | 1/8 | precipitation | 8.13 |
| 6500 DP SAL 4STEP 16X | 1/16 | precipitation | 4.06 |
| 6500 DP SAL 5STEP 32X | 1/32 | heavier precipitation | 2.03 |
| 6500 DP SAL 6STEP 64X | 1/64 | heavy precipitation + slightly turbid | 1.02 |
| 6500 DP SAL 7STEP 128X | 1/128 | heavy precipitation + slightly turbid | 0.51 |
| 6500 DP SAL 8STEP 256X | 1/256 | heavy precipitation + turbid | 0.25 |

TABLE 17

Visual inspection, content and turbidity of RANKL008a before (TUB) and after passage through syringes with different needle size as described in Example 15.

| sample | visual inspection | content (mg/mL) | 320/278 ratio | 350/278 ratio |
|---|---|---|---|---|
| 0028 PLACEBO + TW TUB | clear | 0.288 (0.275-0.301) | 0.0010 | 0.0019 |
| 0028 PLACEBO + TW 18G/18G | clear | 0.285 (0.284-0.286) | 0.0003 | 0.0000 |
| 0028 PLACEBO + TW 18G/23G | clear | 0.288 (0.271-0.307) | 0.0000 | 0.0000 |
| 0028 PLACEBO + TW 18G/27G | clear | 0.285 (0.279-0.290) | 0.0000 | 0.0002 |
| 0028 PLACEBO + TW 18G/30G | clear | 0.286 (0.285-0.287) | 0.0005 | 0.0002 |
| 0028 PLACEBO + TW 23G/23G | clear | 0.287 (0.285-0.289) | 0.0005 | 0.0007 |
| 0028 PLACEBO + TW 27G/27G | clear | 0.285 (0.284-0.286) | 0.0001 | 0.0005 |
| 0028 PLACEBO + TW 30G/30G | clear | 0.287 (0.280-0.294) | 0.0007 | 0.0019 |

TABLE 18

Visual inspection, content and turbidity of RANKL008a before (TUB) and after passage through syringes with different needle size as described in Example 15.

| sample | visual inspection | content (mg/mL) | 320/278 ratio | 350/278 ratio |
|---|---|---|---|---|
| 0028 PLACEBO + TW TUB | clear | 0.284 (0.283-0.285) | 0.0014 | 0.0010 |
| 0028 PLACEBO + TW 27G/27G (3x) | clear | 0.284 (0.283-0.285) | 0.0031 | 0.0021 |
| 0028 PLACEBO + TW 29G/29G B | clear | 0.282 (0.280-0.284) | 0.0024 | 0.0010 |
| 0028 PLACEBO + TW 29G/29G T | clear | 0.283 (0.282-0.284) | 0.0041 | 0.0033 |
| 6500 PLACEBO + TW TUB | clear | 63.5 (62.4-64.6) | 0.0019 | 0.0006 |
| 6500 PLACEBO + TW 27G/27G (3x) | clear | 62.9 (62.7-63.1) | 0.0015 | 0.0008 |

TABLE 19

Overview of the analyses performed using the different stressed samples of RANKL008a at 156 mg/ml (B2#170608nr1).

| | PBS | PBS 0.02% Tween80 (v:v) | PBS 0.05% Tween80 (v:v) | PBS 0.1% Tween80 (v:v) |
|---|---|---|---|---|
| Control | SE-HPLC RP-HPLC PAMAS Potency assay | SE-HPLC RP-HPLC PAMAS Potency assay | SE-HPLC RP-HPLC PAMAS Potency assay | SE-HPLC RP-HPLC PAMAS Potency assay |
| 11 days at 25° C. | SE-HPLC RP-HPLC PAMAS | SE-HPLC RP-HPLC PAMAS | SE-HPLC RP-HPLC PAMAS | SE-HPLC RP-HPLC PAMAS |
| 3 weeks at 25° C. | SE-HPLC RP-HPLC PAMAS | SE-HPLC RP-HPLC PAMAS | SE-HPLC RP-HPLC PAMAS | SE-HPLC RP-HPLC PAMAS |
| 6 weeks at 25° C. | SE-HPLC RP-HPLC PAMAS | SE-HPLC RP-HPLC PAMAS | SE-HPLC RP-HPLC PAMAS | SE-HPLC RP-HPLC PAMAS |
| F/T cycle (−20° C.) | SE-HPLC RP-HPLC PAMAS Potency assay | / | / | SE-HPLC RP-HPLC PAMAS Potency assay |

TABLE 20

Relative potencies (with regard to reference standard) of HSA and RANKL binding moieties of RANKL008a at 156 mg/ml.

| | PBS | PBS 0.02% Tween80 (v:v) | PBS 0.05% Tween80 (v:v) | PBS 0.1% Tween80 (v:v) |
|---|---|---|---|---|
| Control | | | | |
| RANKL | 0.856 | 0.87 | 0.962 | 0.84 |
| HSA | 0.896 | 0.965 | 0.932 | 1.023 |
| F/T cycle (−20° C.) | | | | |
| RANKL | 1.141 | / | / | 1.061 |
| HSA | 1.066 | / | / | 1.116 |

TABLE 21

Stability data of RANKL008a batch NBJ0607-04, stored at −20° C.

| Test Method | Initial (0) | 1 | 2 | 3 |
|---|---|---|---|---|
| Appearance | Clear, slightly yellow solution | Clear, slightly yellow solution | Clear, slightly yellow solution | Clear, slightly yellow solution |
| A278 | 62.5 ± 1.1 mg/mL | 63.0 ± 0.4 mg/mL | 65.4 ± 0.1 mg/mL | 64.8 ± 0.7 mg/mL |
| SEC-HPLC | Purity = 99.8% Pre peaks = 0.2% Post peaks = 0.0% | Purity = 99.7% Pre peaks = 0.3% Post peaks = 0.0% | Purity = 99.6% Pre peaks = 0.4% Post peaks = 0.0% | Purity = 99.7% Pre peaks = 0.3% Post peaks = 0.0% |
| IEX-HPLC | Purity = 95.0% Pre peak 1 = 0.0% Pre peak 2 = 1.0% Pre peak 3 = 1.7% Post peaks = 2.3% | Purity = 95.9% Pre peak 1 = 0.0% Pre peak 2 = 0.8% Pre peak 3 = 1.7% Post peaks = 1.6% | Purity = 95.1% Pre peak 1 = 0.2% Pre peak 2 = 1.0% Pre peak 3 = 2.0% Post peaks = 1.7% | Purity = 95.3% Pre peak 1 = 0.3% Pre peak 2 = 1.0% Pre peak 3 = 2.0% Post peaks = 1.4% |
| RP-HPLC | Purity = 87.8% Pre peaks = 7.8% Post peak 1 = 2.7% Post peak 2 = 1.7% | Purity = 87.8% Pre peaks = 7.7% Post peak 1 = 3.0% Post peak 2 = 1.5% | Purity = 87.8% Pre peaks = 7.9% Post peak 1 = 3.0% Post peak 2 = 1.3% | Purity = 87.5% Pre peaks = 8.2% Post peak 1 = 2.8% Post peak 2 = 1.5% |
| Potency (RANKL inhibition) | 1.098 ± 0.100 | 1.175 ± 0.099 | 0.920 ± 0.065 | 0.980 ± 0.092 |
| Potency (HSA binding) | 0.966 ± 0.065 | 1.021 ± 0.135 | 0.812 ± 0.033 | 0.922 ± 0.038 |

TABLE 21-continued

Stability data of RANKL008a batch NBJ0607-04, stored at −20° C.

| Test Method | Initial (0) | 6 | 9 | 12 |
|---|---|---|---|---|
| Appearance | Clear, slightly yellow solution | Clear, slightly yellow solution | Clear, slightly yellow solution | Clear, slightly yellow solution |
| A278 | 62.5 ± 1.1 mg/mL | 66.4 ± 0.4 mg/mL | 65.7 ± 0.3 mg/mL | 64.7 ± 0.4 mg/mL |
| SEC-HPLC | Purity = 99.8%<br>Pre peaks = 0.2%<br>Post peaks = 0.0% | Purity = 99.8%<br>Pre peaks = 0.2%<br>Post peaks = 0.0% | Purity = 99.8%<br>Pre peaks = 0.2%<br>Post peaks = 0.0% | Purity = 99.7%<br>Pre peaks = 0.1%<br>Post peaks = 0.2% |
| IEX-HPLC | Purity = 95.0%<br>Pre peak 1 = 0.0%<br>Pre peak 2 = 1.0%<br>Pre peak 3 = 1.7%<br>Post peaks = 2.3% | Purity = 95.0%<br>Pre peak 1 = 0.2%<br>Pre peak 2 = 1.1%<br>Pre peak 3 = 2.0%<br>Post peaks = 1.7% | Purity = 95.2%<br>Pre peak 1 = 0.2%<br>Pre peak 2 = 1.1%<br>Pre peak 3 = 2.0%<br>Post peaks = 1.5% | Purity = 94.1%<br>Pre peak 1 = 0.4%<br>Pre peak 2 = 1.2%<br>Pre peak 3 = 2.0%<br>Post peaks = 2.3% |
| RP-HPLC | Purity = 87.8%<br>Pre peaks = 7.8%<br>Post peak 1 = 2.7%<br>Post peak 2 = 1.7% | Purity = 89.7%<br>Pre peaks = 5.5%<br>Post peak 1 = 3.0%<br>Post peak 2 = 1.8% | Purity = 88.7%<br>Pre peaks = 4.4%<br>Post peak 1 = 3.8%<br>Post peak 2 = 3.1% | Purity = 89.2%<br>Pre peaks = 5.1%<br>Post peak 1 = 3.1%<br>Post peak 2 = 2.6% |
| Potency (RANKL inhibition) | 1.098 ± 0.100 | 0.769 ± 0.055 | 0.808 ± 0.047 | 1.201 ± 0.048 |
| Potency (HSA binding) | 0.966 ± 0.065 | 0.889 ± 0.069 | 0.939 ± 0.080 | 0.948 ± 0.061 |

TABLE 22

Stability data of RANKL008a batch NBJ0607-04, stored at +5° C.

| Test Method | Initial (0) | 1 | 2 | 3 |
|---|---|---|---|---|
| Appearance | Clear, slightly yellow solution | Clear, slightly yellow solution | Clear, slightly yellow solution | Clear, slightly yellow solution |
| A278 | 62.5 ± 1.1 mg/mL | 61.3 ± 2.0 mg/mL | 65.3 ± 0.4 mg/mL | 65.1 ± 0.6 mg/mL |
| SEC-HPLC | Purity = 99.8%<br>Pre peaks = 0.2%<br>Post peaks = 0.0% | Purity = 99.6%<br>Pre peaks = 0.4%<br>Post peaks = 0.0% | Purity = 99.4%<br>Pre peaks = 0.6%<br>Post peaks = 0.0% | Purity = 99.7%<br>Pre peaks = 0.3%<br>Post peaks = 0.0% |
| IEX-HPLC | Purity = 95.0%<br>Pre peak 1 = 0.0%<br>Pre peak 2 = 1.0%<br>Pre peak 3 = 1.7%<br>Post peaks = 2.3% | Purity = 95.7%<br>Pre peak 1 = 0.0%<br>Pre peak 2 = 1.0%<br>Pre peak 3 = 1.8%<br>Post peaks = 1.5% | Purity = 95.3%<br>Pre peak 1 = 0.2%<br>Pre peak 2 = 1.0%<br>Pre peak 3 = 2.0%<br>Post peaks = 1.5% | Purity = 95.5%<br>Pre peak 1 = 0.2%<br>Pre peak 1 = 1.0%<br>Pre peak 2 = 1.9%<br>Post peaks = 1.4% |
| RP-HPLC | Purity = 87.8%<br>Pre peaks = 7.8%<br>Post peak 1 = 2.7%<br>Post peak 2 = 1.7% | Purity = 88.1%<br>Pre peaks = 7.3%<br>Post peak 1 = 3.0%<br>Post peak 2 = 1.6% | Purity = 87.9%<br>Pre peaks = 7.6%<br>Post peak 1 = 3.0%<br>Post peak 2 = 1.5% | Purity = 87.5%<br>Pre peaks = 8.2%<br>Post peak 1 = 2.8%<br>Post peak 2 = 1.5% |
| Potency (RANKL inhibition) | 1.098 ± 0.100 | 1.094 ± 0.090 | 1.026 ± 0.064 | 0.937 ± 0.079 |
| Potency (HSA binding) | 0.966 ± 0.065 | 1.132 ± 0.127 | 0.917 ± 0.045 | 0.860 ± 0.042 |

| Test Method | Initial (0) | 6 | 9 | 12 |
|---|---|---|---|---|
| Appearance | Clear, slightly yellow solution | Clear, slightly yellow solution | Clear, slightly yellow solution | Clear, slightly yellow solution |
| A278 | 62.5 ± 1.1 mg/mL | 66.8 ± 0.6 mg/mL | 65.0 ± 0.4 mg/mL | 64.7 ± 0.9 mg/mL |
| SEC-HPLC | Purity = 99.8%<br>Pre peaks = 0.2%<br>Post peaks = 0.0% | Purity = 99.6%<br>Pre peaks = 0.2%<br>Post peaks = 0.2% | Purity = 99.3%<br>Pre peaks = 0.3%<br>Post peaks = 0.4% | Purity = 99.1%<br>Pre peaks = 0.2%<br>Post peaks = 0.7% |
| IEX-HPLC | Purity = 95.0%<br>Pre peak 1 = 0.0%<br>Pre peak 2 = 1.0%<br>Pre peak 3 = 1.7%<br>Post peaks = 2.3% | Purity = 95.2%<br>Pre peak 1 = 0.3%<br>Pre peak 2 = 1.0%<br>Pre peak 3 = 2.0%<br>Post peaks = 1.5% | Purity = 94.7%<br>Pre peak 1 = 0.3%<br>Pre peak 2 = 1.0%<br>Pre peak 3 = 2.1%<br>Post peaks = 1.9% | Purity = 92.0%<br>Early peaks = 0.2%<br>Pre peak 1 = 0.3%<br>Pre peak 2 = 1.3%<br>Pre peak 3 = 2.2%<br>Post peaks = 4.0% |

TABLE 22-continued

Stability data of RANKL008a batch NBJ0607-04, stored at +5° C.

| RP-HPLC | Purity = 87.8% | Purity = 90.0% | Purity = 88.0% | Purity = 89.6% |
|---|---|---|---|---|
| | Pre peaks = 7.8% | Pre peaks = 5.2% | Pre peaks = 5.1% | Pre peaks = 4.7% |
| | Post peak 1 = 2.7% | Post peak 1 = 3.0% | Post peak 1 = 4.0% | Post peak 1 = 3.3% |
| | Post peak 2 = 1.7% | Post peak 2 = 1.8% | Post peak 2 = 2.9% | Post peak 2 = 2.4% |
| Potency (RANKL inhibition) | 1.098 ± 0.100 | 0.911 ± 0.045 | 0.891 ± 0.032 | 1.106 ± 0.047 |
| Potency (HSA binding) | 0.966 ± 0.065 | 0.851 ± 0.066 | 1.062 ± 0.065 | 1.023 ± 0.082 |

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All references disclosed herein are incorporated by reference, in particular for the teaching that is referenced hereinabove.

The invention claimed is:

1. A formulation comprising
a polypeptide with SEQ ID NO: 1,
10 mM disodium hydrogen phosphate (Na2HPO4) pH 7.0;
115 mM sodium chloride (NaCl); and
0.01% Tween80 (v:v),
said formulation being formulated for administration to a human subject, wherein the polypeptide has a concentration of at least 30 mg/ml, and wherein less than 25% of the polypeptides form dimers during storage at 37° C. up to 2 weeks, the % of dimers as measured by SE-HPLC.

2. The formulation of claim 1, wherein the polypeptide has a concentration of at least 60 mg/ml.

3. The formulation of claim 2, wherein the polypeptide has a concentration of at least 80 mg/ml.

4. The formulation of claim 1, wherein the polypeptide has a biphasic melting temperature profile wherein one Tm1 is at least 60° C. and Tm2 is at least 65° C., as measured by the thermal shift assay and/or differential scanning calorimetry (DSC).

5. The formulation claim 1, wherein the polypeptide:
is stable after multiple freeze/thaw cycles, said stability as determined by SE-HPLC, IEX-HPLC, RP-HPLC, Biacore analysis and/or potency assay;
is stable during storage at a temperature of −20±5° C. up to at least 3 months, said stability as determined by SE-HPLC and/or RP-HPLC;
is stable during storage at a temperature of 2-8° C. up to at least 3 months, said stability as determined by SE-HPLC, RP-HPLC and/or potency assay;
is stable during storage at a temperature of 25±5° C. up to at least 2 weeks, said stability as determined by SE-HPLC, RP-HPLC, potency assay and/or SDS-PAGE;
is stable during storage at a temperature of 37±5° C. up to at least 2 weeks, said stability as determined by SE-HPLC, RP-HPLC, potency assay and/or SDS-PAGE; and/or
is stable under mechanical stress.

6. The formulation of claim 1, wherein
less than 10% of the polypeptides forms pyroglutamate at the N-terminal glutamic acid during storage, the % of pyroglutamate as measured by RP-HPLC;
less than 10% of the polypeptides forms pyroglutamate at the N-terminal glutamic acid during storage at a temperature of 37±5° C., the % of pyroglutamate as measured by RP-HPLC; and/or
less than 25% of the polypeptides forms dimers during storage, the % of dimers as measured by SE-HPLC.

7. The formulation of claim 1, that does not show the formation of aggregates as measured by SE-HPLC, subvisible particle counting, analytical ultracentrifugation and/or dynamic light scattering.

8. The formulation of claim 1, wherein
at least 80% of the polypeptides retain their binding activity to RANKL after storage compared to the binding activity prior to storage, said binding activity as measured by ELISA and/or Biacore; and/or
at least 80% of the polypeptides retain their binding activity to HSA after storage compared to the binding activity prior to storage, said binding activity as measured by ELISA and/or Biacore.

9. The formulation of claim 8, wherein
at least 80% of the polypeptides retain their binding activity to RANKL after storage at 37±5° C. compared to the binding activity prior to storage, said binding activity as measured by ELISA and/or Biacore; and/or
at least 80% of the polypeptides retain their binding activity to HSA after storage at 37±5° C. compared to the binding activity prior to storage, said binding activity as measured by ELISA and/or Biacore.

10. The formulation of claim 1, wherein the single variable domain is stable under mechanical stress.

11. The formulation of claim 10, wherein the mechanical stress is selected from shaking during 10 s to 1 min, pushing through a needle with a syringe, rotation for two days at 10 rpm, and stirring for 1 hour at room temperature and 2 days at 4° C. at least 10 rpm.

12. The formulation according to claim 1, which has an osmolality of 290±60 mOsm/kg.

13. A method for the preparation of the formulation of claim 1, comprising the step of concentrating the polypeptide with SEQ ID NO: 1 and exchanging it with a buffer.

14. A formulation which is produced by lyophilizing or spray drying the formulation according to claim 1.

15. A method for the preparation of a lyophilized or spray dried formulation comprising the step of freeze-drying or spray drying the formulation of claim 1.

16. A sealed container containing a formulation according to claim 1.

17. A kit comprising one or more of the sealed containers according to claim 16, and instructions for use of the formulation.

18. A pharmaceutical unit dosage form suitable for parenteral administration to a human, comprising a formulation according to claim 1 in a suitable container.

19. The pharmaceutical unit dosage form of claim 18, which is suitable for subcutaneous administration.

20. A kit comprising one or more unit dosage forms according to claim 18, and instructions for use of the formulation.

21. The formulation of claim 1, for use in therapy.

22. The formulation of claim 1, wherein less than 15% of the polypeptides form dimers during storage at 37° C. up to 2 weeks, the % of dimers as measured by SE-HPLC.

* * * * *

```
                       SEQUENCE LISTING

<160> NUMBER OF SEQ ID NOS: 1

<210> SEQ ID NO 1
   <211> LENGTH: 385
   <212> TYPE: PRT
   <213> ORGANISM: Artificial Sequence
   <220> FEATURE:
   <223> OTHER INFORMATION: Nanobody sequence

<400> SEQUENCE: 1

Glu Val Gln Leu Val Glu Ser Gly Gly Gly Leu Val Gln Pro Gly Gly
   1               5                   10                  15

Ser Leu Arg Leu Ser Cys Ala Ala Ser Gly Phe Thr Phe Ser Ser Tyr
                   20                  25                  30

Pro Met Gly Trp Phe Arg Gln Ala Pro Gly Lys Gly Arg Glu Phe Val
               35                  40                  45

Ser Ser Ile Thr Gly Ser Gly Gly Ser Thr Tyr Tyr Ala Asp Ser Val
       50                  55                  60

Lys Gly Arg Phe Thr Ile Ser Arg Asp Asn Ala Lys Asn Thr Leu Tyr
   65                  70                  75                  80

Leu Gln Met Asn Ser Leu Arg Pro Glu Asp Thr Ala Val Tyr Tyr Cys
                   85                  90                  95

Ala Ala Tyr Ile Arg Pro Asp Thr Tyr Leu Ser Arg Asp Tyr Arg Lys
               100                 105                 110

Tyr Asp Tyr Trp Gly Gln Gly Thr Leu Val Thr Val Ser Ser Gly Gly
               115                 120                 125

Gly Gly Ser Gly Gly Gly Ser Glu Val Gln Leu Val Glu Ser Gly Gly
       130                 135                 140

Gly Leu Val Gln Pro Gly Asn Ser Leu Arg Leu Ser Cys Ala Ala Ser
   145                 150                 155                 160

Gly Phe Thr Phe Ser Ser Phe Gly Met Ser Trp Val Arg Gln Ala Pro
                   165                 170                 175

Gly Lys Gly Leu Glu Trp Val Ser Ser Ile Ser Gly Ser Gly Ser Asp
               180                 185                 190

Thr Leu Tyr Ala Asp Ser Val Lys Gly Arg Phe Thr Ile Ser Arg Asp
               195                 200                 205

Asn Ala Lys Thr Thr Leu Tyr Leu Gln Met Asn Ser Leu Arg Pro Glu
       210                 215                 220
```

```
Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Gly Ser Thr Tyr Tyr Ala
305                 310                 315                 320

Asp Ser Val Lys Gly Arg Phe Thr Ile Ser Arg Asp Asn Ala Lys Asn
                325                 330                 335

Thr Leu Tyr Leu Gln Met Asn Ser Leu Arg Pro Glu Asp Thr Ala Val
                340                 345                 350

Tyr Tyr Cys Ala Ala Tyr Ile Arg Pro Asp Thr Tyr Leu Ser Arg Asp
            355                 360                 365

Tyr Arg Lys Tyr Asp Tyr Trp Gly Gln Gly Thr Leu Val Thr Val Ser
    370                 375                 380

Ser
385
```